(12) United States Patent
Abazeed

(10) Patent No.: US 10,391,173 B2
(45) Date of Patent: Aug. 27, 2019

(54) ANTI-AR AGENT AND RADIATION THERAPY FOR ANDROGEN RECEPTOR POSITIVE CANCER

(71) Applicant: The Cleveland Clinic Foundation, Cleveland, OH (US)

(72) Inventor: Mohamed Abazeed, Cleveland, OH (US)

(73) Assignee: THE CLEVELAND CLINIC FOUNDATION, Cleveland, OH (US)

(*) Notice: Subject to any disclaimer, the term of this patent is extended or adjusted under 35 U.S.C. 154(b) by 0 days.

(21) Appl. No.: 15/493,901

(22) Filed: Apr. 21, 2017

(65) Prior Publication Data
US 2017/0319692 A1    Nov. 9, 2017

Related U.S. Application Data

(60) Provisional application No. 62/326,203, filed on Apr. 22, 2016.

(51) Int. Cl.
| | | |
|---|---|---|
| *A61K 41/00* | (2006.01) | |
| *A61N 5/10* | (2006.01) | |
| *A61K 51/00* | (2006.01) | |
| *A61K 31/545* | (2006.01) | |
| *A61K 45/06* | (2006.01) | |
| *A61K 31/167* | (2006.01) | |
| *A61K 31/277* | (2006.01) | |
| *A61K 31/402* | (2006.01) | |
| *A61K 31/4164* | (2006.01) | |
| *A61K 31/4166* | (2006.01) | |
| *A61K 31/496* | (2006.01) | |
| *A61K 31/57* | (2006.01) | |
| *A61K 31/585* | (2006.01) | |
| *A61N 5/00* | (2006.01) | |

(52) U.S. Cl.
CPC ........ *A61K 41/0038* (2013.01); *A61K 31/167* (2013.01); *A61K 31/277* (2013.01); *A61K 31/402* (2013.01); *A61K 31/4164* (2013.01); *A61K 31/4166* (2013.01); *A61K 31/496* (2013.01); *A61K 31/545* (2013.01); *A61K 31/57* (2013.01); *A61K 31/585* (2013.01); *A61K 41/0019* (2013.01); *A61K 45/06* (2013.01); *A61K 51/00* (2013.01); *A61N 5/00* (2013.01); *A61N 5/10* (2013.01); *A61N 2005/1098* (2013.01)

(58) Field of Classification Search
None
See application file for complete search history.

(56) References Cited

PUBLICATIONS

Dana-Farber/Harvard Cancer Center news, published online Jan. 27, 2015 (http://www.dfhcc.harvard.edu/news/detail/story/enzalutamide-plus-ebrt-as-a-novel-treatment-approach-in-intermediate-risk-prostate-cancer/).*
Williams et al (Annals of Oncology, 2014, 25 (Suppl 4):iv255-iv279) Poster.*
Williams et al (Annals of Oncology, 2014, 25 (Suppl 4):iv255-iv279) Abstract for poster.*
Farooqi et al (Cancer Cell International, 2015, 15:7, pp. 1-9).*
Schalken et al (BJU Int, 2016, 117:215-225; published online Jun. 26, 2015).*
Barton et al (Molecular Cancer Therapeutics, 2015, 14:769-778).*
Gucalp et al (Clinical Cancer Research, 2013, 19:5505-5512).*
Abazeed et al., Integrative radiogenomic profiling of squamous cell lung cancer. Cancer Res. Oct. 15, 2013;73(20):6289-9.
Akiyama et al., The transforming potential of the c-erbB-2 protein is regulated by its autophosphorylation at the carboxyl-terminal domain. Mol Cell Biol. Feb. 1991;11(2):833-42.
Alhassani et al., The sources of the SGR "hole". N Engl J Med. Jan. 26, 2012;366(4):289-91.
Bao et al., RAN-binding protein 9 is involved in alternative splicing and is critical for male germ cell development and male fertility. PLoS Genet. Dec. 4, 2014;10(12):e1004825.
Barbie et al., Systematic RNA interference reveals that oncogenic KRAS-driven cancers require TBK1. Nature. Nov. 5, 2009;462(7269):108-12.
Barretina et al., The Cancer Cell Line Encyclopedia enables predictive modelling of anticancer drug sensitivity. Nature. Mar. 28, 2012;483(7391):603-7.
Barton et al., Multiple molecular subtypes of triple-negative breast cancer critically rely on androgen receptor and respond to enzalutamide in vivo. Mol Cancer Ther. Mar. 2015;14(3):769-78.
Beroukhim et al., The landscape of somatic copy-number alteration across human cancers. Nature. Feb. 18, 2010;463(7283):899-905.
Bolla et al., Long-term results with immediate androgen suppression and external irradiation in patients with locally advanced prostate cancer (an EORTC study): a phase III randomised trial. Lancet. Jul. 13, 2002;360(9327):103-6.
Brumbaugh et al., The mRNA surveillance protein hSMG-1 functions in genotoxic stress response pathways in mammalian cells. Mol Cell. Jun. 4, 2004;14(5):585-98.
Brys et al., Androgen receptor status in female breast cancer: RT-PCR and Western blot studies. J Cancer Res Clin Oncol. Feb. 2002;128(2):85-90.
Buchanan et al., Locoregional recurrence after mastectomy: incidence and outcomes. J Am Coll Surg. Oct. 2006;203(4):469-74.

(Continued)

Primary Examiner — Laura B Goddard
(74) Attorney, Agent, or Firm — Casimir Jones, S.C.; Jason Bond

(57) ABSTRACT

Provided herein are compositions, systems, kits, and methods for treating cancer in a subject with androgen receptor positive cancer cells by sensitizing such cancer cells with anti-androgen receptor therapy (e.g., Enzalutamide or anti-androgen antibody), and then treating with radiation therapy.

12 Claims, 51 Drawing Sheets

(56) References Cited

PUBLICATIONS

Cai et al., Optimized digital counting colonies of clonogenic assays using ImageJ software and customized macros: comparison with manual counting. Int J Radiat Biol. Nov. 2011;87(11):1135-46.

Cancer Genome Atlas Network. Comprehensive molecular characterization of human colon and rectal cancer. Nature. Jul. 18, 2012;487(7407):330-7.

Cancer Genome Atlas Research Network. Comprehensive genomic characterization defines human glioblastoma genes and core pathways. Nature. Oct. 23, 2008;455(7216):1061-8.

Cancer Genome Atlas Research Network. Comprehensive genomic characterization of squamous cell lung cancers. Nature. Sep. 27, 2012;489(7417):519-25.

Cancer Genome Atlas Research Network. Comprehensive molecular profiling of lung adenocarcinoma. Nature. Jul. 31, 2014;511(7511):543-50.

Cancer Genome Atlas Research Network. Integrated genomic characterization of endometrial carcinoma. Nature. May 2, 2013;497(7447):67-73.

Chapman et al. Improved survival with vemurafenib in melanoma with BRAF V600E mutation. N Engl J Med. Jun. 30, 2011;364(26):2507-16.

Cochrane et al., Role of the androgen receptor in breast cancer and preclinical analysis of enzalutamide. Breast Cancer Res. Jan. 22, 2014;16(1):R7.

Cowley et al., Parallel genome-scale loss of function screens in 216 cancer cell lines for the identification of context-specific genetic dependencies. Sci Data. Sep. 30, 2014;1:140035.

D'Amico et al., 6-month androgen suppression plus radiation therapy vs radiation therapy alone for patients with clinically localized prostate cancer: a randomized controlled trial. JAMA. Aug. 18, 2004;292(7):821-7.

Dinkova-Kostova et al., NAD(P)H:quinone acceptor oxidoreductase 1 (NQO1), a multifunctional antioxidant enzyme and exceptionally versatile cytoprotector. Arch Biochem Biophys. Sep. 1, 2010;501(1):116-23.

Druker et al., Efficacy and safety of a specific inhibitor of the BCR-ABL tyrosine kinase in chronic myeloid leukemia. N Engl J Med. Apr. 5, 2001;344(14):1031-7.

Early Breast Cancer Trialists' Collaborative Group. Effect of radiotherapy after breast-conserving surgery on 10-year recurrence and 15-year breast cancer death: meta-analysis of individual patient data for 10,801 women in 17 randomised trials. Lancet. Nov. 12, 2011;378(9804):1707-16.

Early Breast Cancer Trialists' Collaborative Group. Effect of radiotherapy after mastectomy and axillary surgery on 10-year recurrence and 20-year breast cancer mortality: meta-analysis of individual patient data for 8135 women in 22 randomised trials. Lancet 383, 2127-2135 (2014).

Engelman et al., MET amplification leads to gefitinib resistance in lung cancer by activating ERBB3 signaling. Science. May 18, 2007;316(5827):1039-43.

Franken et al., Clonogenic assay of cells in vitro. Nat Protoc. 2006;1(5):2315-9.

Galy et al., . Nuclear pore complexes in the organization of silent telomeric chromatin. Nature. Jan. 6, 2000;403(6765):108-12.

Gong et al., Role of the mammalian SWI/SNF chromatin remodeling complex in the cellular response to UV damage. Cell Cycle. Apr. 15, 2008;7(8):1067-74.

Goodwin et al., A hormone-DNA repair circuit governs the response to genotoxic insult. Cancer Discov. Nov. 2013;3(11):1254-71.

Gucalp et al., Phase II trial of bicalutamide in patients with androgen receptor-positive, estrogen receptor-negative metastatic Breast Cancer. Clin Cancer Res. Oct. 1, 2013;19(19):5505-12.

Harrington et al., VX-680, a potent and selective small-molecule inhibitor of the Aurora kinases, suppresses tumor growth in vivo. Nat Med. Mar. 2004;10(3):262-7.

Hast et al., Cancer-derived mutations in KEAP1 impair NRF2 degradation but not ubiquitination. Cancer Res. Feb. 1, 2014;74(3):808-17.

Hastings et al., Mechanisms of change in gene copy number. Nat Rev Genet. Aug. 2009;10(8):551-64.

Huston et al., Locally recurrent breast cancer after conservation therapy. Am J Surg. Feb. 2005;189(2):229-35.

Jiang et al., Phosphatase and tensin homologue deficiency in glioblastoma confers resistance to radiation and temozolomide that is reversed by the protease inhibitor nelfinavir. Cancer Res. May 1, 2007;67(9):4467-73.

JOE, Relative Entropy Measures of Multivariate Dependence. Journal of the American Statistical Association. 1989;84(405):157-64.

Joon et al., Supraadditive apoptotic response of R3327-G rat prostate tumors to androgen ablation and radiation. Int J Radiat Oncol Biol Phys. Jul. 15, 1997;38(5):1071-7.

Komatsu et al., The selective autophagy substrate p62 activates the stress responsive transcription factor Nrf2 through inactivation of Keap1. Nat Cell Biol. Mar. 2010;12(3):213-23.

Korn et al., Integrated genotype calling and association analysis of SNPs, common copy number polymorphisms and rare CNVs. Nat Genet. Oct. 2008;40(10):1253-60.

KRASILNIKOVet al., Contribution of phosphatidylinositol 3-kinase to radiation resistance in human melanoma cells. Mol Carcinog. Jan. 1999;24(1):64-9.

Lee et al., Phosphatidylinositol 3-kinase, not extracellular signal-regulated kinase, regulates activation of the antioxidant-responsive element in IMR-32 human neuroblastoma cells. J Biol Chem. Jun. 8, 2001;276(23):20011-6.

Lee et al., RAD21L, a novel cohesin subunit implicated in linking homologous chromosomes in mammalian meiosis. J Cell Biol. Jan. 24, 2011;192(2):263-76.

Lehmann et al., Identification of human triple-negative breast cancer subtypes and preclinical models for selection of targeted therapies. J Clin Invest. Jul. 2011;121(7):2750-67.

Li et al., RSEM: accurate transcript quantification from RNA-Seq data with or without a reference genome. BMC Bioinformatics. Aug. 4, 2011;12:323.

Liang et al., of breast cancer cells to radiation by trastuzumab. Mol Cancer Ther. Nov. 2003;2(11):1113-20.

LINFOOT, An informational measure of correlation. Information and Control. 1957;1(1):85-89.

Lynch et al., Activating mutations in the epidermal growth factor receptor underlying responsiveness of non-small-cell lung cancer to gefitinib. N Engl J Med. May 20, 2004;350(21):2129-39.

Malhotra et al., Global mapping of binding sites for Nrf2 identifies novel targets in cell survival response through ChIP-Seq profiling and network analysis. Nucleic Acids Res. Sep. 2010;38(17):5718-3.

MARIS, Recent advances in neuroblastoma. N Engl J Med. Jun. 10, 2010;362(23):2202-11.

Martini et al., PI3K/AKT signaling pathway and cancer: an updated review. Ann Med. Sep. 2014;46(6):372-83.

Mathew et al., Autophagy suppresses tumorigenesis through elimination of p62. Cell. Jun. 12, 2009;137(6):1062-75.

Mermel et al., GISTIC2.0 facilitates sensitive and confident localization of the targets of focal somatic copy-No. alteration in human cancers. Genome Biol. 2011;12(4):R41.

Mitsuishi et al., . Nrf2 redirects glucose and glutamine into anabolic pathways in metabolic reprogramming. Cancer Cell. Jul. 10, 2012;22(1):66-79.

Olshen et al., Circular binary segmentation for the analysis of array-based DNA copy number data. Biostatistics. Oct. 2004;5(4):557-72.

Pilepich et al., Phase III radiation therapy oncology group (RTOG) trial 86-10 of androgen deprivation adjuvant to definitive radiotherapy in locally advanced carcinoma of the prostate. Int J Radiat Oncol Biol Phys. Aug. 1, 2001;50(5):1243-52.

Ree et al., Personalized radiotherapy: concepts, biomarkers and trial design.Br J Radiol. Jul. 2015;88(1051):20150009.

Rosell et al., Erlotinib versus standard chemotherapy as first-line treatment for European patients with advanced EGFR mutation-

(56) References Cited

PUBLICATIONS positive non-small-cell lung cancer (EURTAC): a multicentre, open-label, randomised phase 3 trial. Lancet Oncol. Mar. 2012;13(3):239-46.

Schultz et al., p53 binding protein 1 (53BP1) is an early participant in the cellular response to DNA double-strand breaks. J Cell Biol. Dec. 25, 2000;151(7):1381-90.

Seashore-Ludlow et al., Harnessing Connectivity in a Large-Scale Small-Molecule Sensitivity Dataset. Cancer Discov. Nov. 2015;5(11):1210-23.

Shibata et al., Cancer related mutations in NRF2 impair its recognition by Keap1-Cul3 E3 ligase and promote malignancy. Proc Natl Acad Sci U S A. Sep. 9, 2008;105(36):13568-73.

Slamon et al., Use of chemotherapy plus a monoclonal antibody against HER2 for metastatic breast cancer that overexpresses HER2. N Engl J Med. Mar. 15, 2001;344(11):783-92.

Solis et al., Nrf2 and Keap1 abnormalities in non-small cell lung carcinoma and association with clinicopathologic features. Clin Cancer Res. Jul. 15, 2010;16(14):3743-53.

Taguchi et al., Molecular mechanisms of the Keap1-Nrf2 pathway in stress response and cancer evolution. Genes Cells. Feb. 2011;16(2):123-40.

Velkova et al., Monteiro AN. Identification of Filamin A as a BRCA1-interacting protein required for efficient DNA repair. Cell Cycle. Apr. 1, 2010;9(7):1421-33.

Yard et al., Radiotherapy in the Era of Precision Medicine. Semin Radiat Oncol. Oct. 2015;25(4):227-36.

Zack et al., Pan-cancer patterns of somatic copy No. alteration. Nat Genet. Oct. 2013;45(10):1134-40.

Zaidi et al., Novel targeted radiosensitisers in cancer treatment. Curr Drug Discov Technol. Jun. 2009;6(2):103-34.

Zhang et al., Loss of Kelch-like ECH-associated protein 1 function in prostate cancer cells causes chemoresistance and radioresistance and promotes tumor growth. Mol Cancer Ther. Feb. 2010;9(2):336-46.

\* cited by examiner

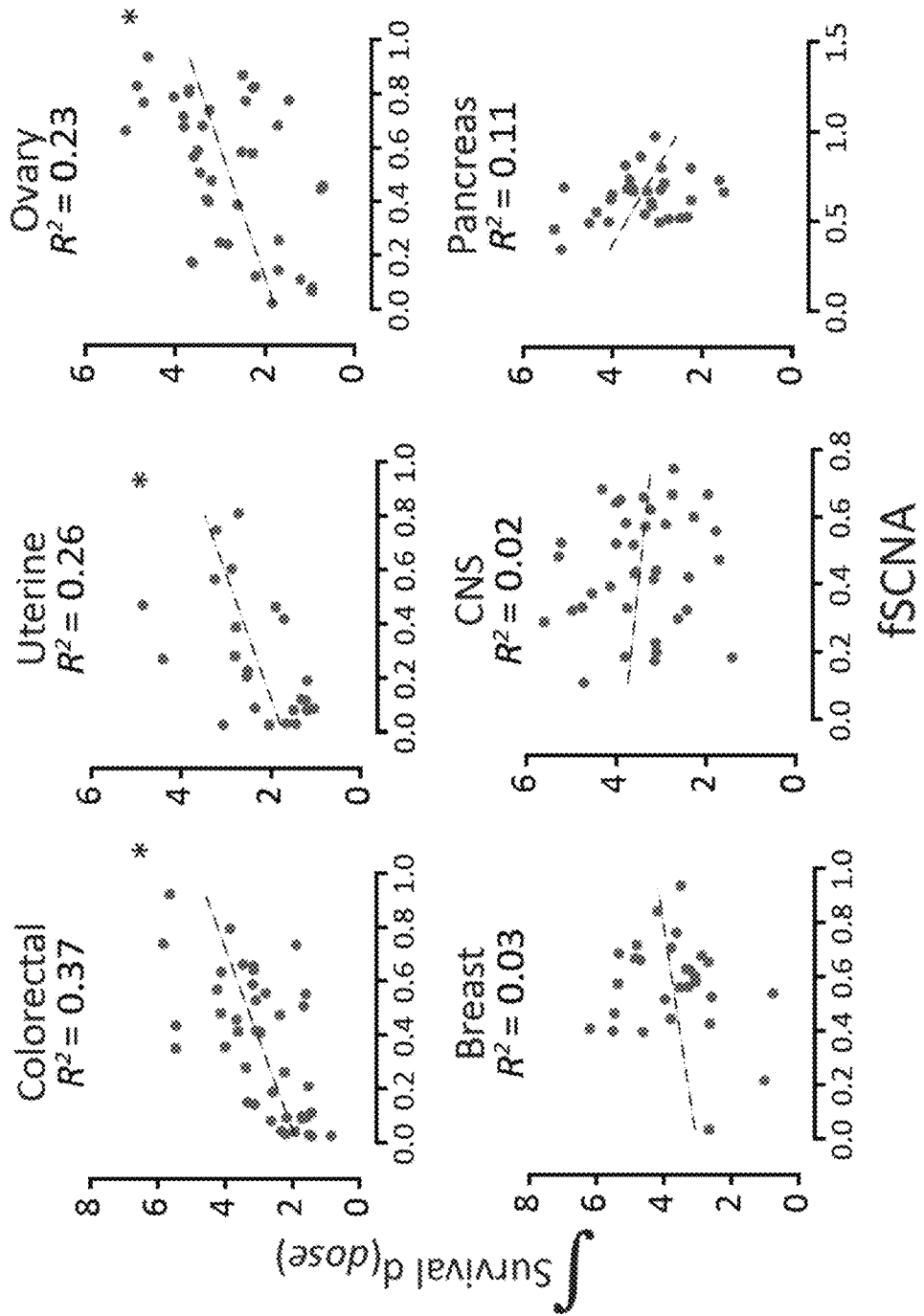

ANTI-AR AGENT AND RADIATION THERAPY FOR ANDROGEN RECEPTOR POSITIVE CANCER

The present application claims priority to U.S. Provisional application Ser. No. 62/326,203, filed Apr. 22, 2016 which is herein incorporated by reference in its entirety.

FIELD

Provided herein are compositions, systems, kits, and methods for treating cancer in a subject with androgen receptor positive cancer cells by sensitizing such cancer cells with anti-androgen receptor therapy (e.g., Enzalutamide or anti-androgen antibody), and then treating with radiation therapy.

BACKGROUND

Clinical radiotherapy has made significant advances since its inception, growing into a tertiary specialty with significant contributions to curative and palliative treatments of cancer and health care cost[1]. A major limitation to its appropriate application, however, has been the lack of measurable biological indicators, or biomarkers, that can reliably identify patients with cancers that are more or less likely to respond to these treatments[2, 3].

Advances in genomic technology have enabled a cataloguing of cancer genes that has resulted in the identification of genetic alterations that contribute to oncogenesis and/or tumor progression and in some cases has led to significant therapeutic advances[4, 5, 6, 7]. In contrast, X-rays and DNA-damaging drugs are delivered based on the site of anatomical origin of disease and do not currently take into account the genetic complexity that may regulate therapeutic response.

SUMMARY

Provided herein are compositions, systems, kits, and methods for treating cancer in a subject with androgen receptor positive cancer cells by sensitizing such cancer cells with anti-androgen receptor therapy (e.g., Enzalutamide or anti-androgen antibody), and then treating with radiation therapy.

In some embodiments, provided herein are methods of treating cancer comprising: a) determining that a subject has androgen receptor positive cancer cells (e.g., breast cancer cells); b) treating the subject with an anti-androgen receptor agent; and c) treating the subject with radiation therapy, wherein the radiation therapy is performed at least 30 minutes (e.g., at least 12 hours or 3 days) after the treating with the anti-androgen receptor agent, and wherein the treating causes at least a portion of the androgen receptor positive cancer cells to die. In certain embodiments, the treating with anti-androgen receptor agent is conduced for a day . . . a week . . . a month . . . or two months. In certain embodiments, the subject is a human subject (e.g., male or female). In other embodiments, the subject is an animal, such as a dog, cat, horse, cow, or other domesticated animal.

In certain embodiments, the anti-androgen receptor agent sensitizes the androgen positive cancer cells to the radiation therapy, such that a higher proportion of the cancer cells are killed by the radiation therapy than without the anti-androgen receptor agent. In other embodiments, the radiation therapy is performed at least 1 hour after the treating with the anti-androgen receptor agent. In further embodiments, the radiation therapy is performed at least 1-24 hours after the treating with the anti-androgen receptor agent (e.g., 1 . . . 4 . . . 8 . . . 12 . . . 16 . . . 20 . . . 24 . . . 28 hours). In certain embodiments, the treating with anti-androgen receptor agent is at least 1-2 months before the radiation therapy. In other embodiments, when radiation therapy is administered, additional anti-androgen receptor agent is administered at the same or about the same time. In further embodiments, after such radiation therapy is concluded, and additional 1 day . . . 1 week . . . 1 month . . . 2 months of anti-androgen receptor agent treatment is provided. In particular embodiments, the radiation therapy is performed at least 1.1-3 days after the treating with the anti-androgen receptor agent. In particular embodiments, the anti-androgen receptor agent is administered to the subject in a dosage between 1 mg/kg to 35 mg/kg (e.g., 1 . . . 5 . . . 10 . . . 23 . . . 30 . . . or 35 mg/kg). In other embodiments, the anti-androgen receptor agent is administered to the subject in a dosage of about 10-15 mg/kg. In certain embodiments, the present disclosure is employed before and/or after surgical removal of a subject's tumor.

In further embodiments, the determining comprises receiving or reviewing a report that the subject has androgen positive cancer cells. In additional embodiments, the determining comprises performing an in vitro assay on a sample from the subject. In some embodiments, the anti-androgen receptor agent is an androgen receptor antagonists selected from the group consisting of: flutamide, nilutamide, bicalutamide, enzalutamide, apalutamide, cyproterone acetate, megestrol acetate, chlormadinone acetate, spironolactone, canrenone, drospirenone, ketoconazole, topilutamide (fluridil), abiraterone, and cimetidine. In some embodiments, the anti-androgen receptor agent is a selective androgen receptor modulator (SARM) selected from the group consisting of: Enobosarm (Ostarine, MK-2866, GTx-024), BMS-564,929; LGD-4033 (Ligandrol), agent in U.S. Pat. No. 7,605,152 SARM (5-3/5-6); AC-262,356; JNJ-28330835; LGD-2226; LGD-3303; S-40503; and S-23. In additional embodiments, the anti-androgen is an antibody, or fragment thereof, to the androgen receptor.

In particular embodiments, the androgen receptor positive cancer cells are a type of cancer selected from the group consisting of: breast, prostate, colon, leukemia, brain, bone, skin, liver, pancreatic, stomach, and lung. In other embodiments, the radiation therapy comprises subjecting the subject to X-rays, gamma rays, and or charged particles. In certain embodiments, the cells are triple negative breast cancer cells (estrogen receptor-negative, progesterone receptor-negative and HER2-negative).

In further embodiments, provided herein are systems comprising: a) a radiation therapy device, and b) an anti-androgen receptor agent. In some embodiments, the radiation therapy device is configured to emit X-rays, gamma rays, or charged particles for cancer treatment. In other embodiments, the anti-androgen receptor agent is an androgen receptor antagonists selected from the group consisting of: flutamide, nilutamide, bicalutamide, enzalutamide, apalutamide, cyproterone acetate, megestrol acetate, chlormadinone acetate, spironolactone, canrenone, drospirenone, ketoconazole, topilutamide (fluridil), and cimetidine. In particular embodiments, the anti-androgen receptor agent is a selective androgen receptor modulator (SARM) selected from the group consisting of: Enobosarm (Ostarine, MK-2866, GTx-024), BMS-564,929; LGD-4033 (Ligandrol), agent in U.S. Pat. No. 7,605,152 SARM (5-3/5-6); AC-262,356; JNJ-28330835; LGD-2226; LGD-3303; S-40503; and S-23.

In certain embodiments, the systems further comprise: c) a report that a subject has androgen receptor cancer cells, or c) androgen receptor positive cancer cells. In some embodiments, the anti-androgen is an antibody, or fragment thereof, to the androgen receptor.

DESCRIPTION OF THE FIGURES

FIGS. 2A-2F. SCNA changes are associated with survival after radiation-induced damage. (a) Plots of fSCNA, integral survival, and number of mutations per sample. (b) The top 50 probes that correlate with radiation resistance (left) and sensitivity (right) are shown. Radii (single probe) or sectors (multiple probes) correspond to chromosome positions. Each radius represents a distinct probe that mapped to the designated chromosome position. (c) Individual SCNA can regulate the response to radiation directly. We correlated radiation survival with the expression of genes within the altered segments and compared the means of the coefficients by pair-wise analysis, resistant versus sensitive. Spearman means for alterations depicted in (b) were analyzed by ANOVA and Tukey Contrasts. 95% confidence level intervals for each pairwise comparison are shown. (d) Scatter plots, linear regression, and $R^2$ values of the integral survival and fSCNA by lineage. (e) Scatter plot and linear regression of integral survival, fSCNA, and the number of mutations (MUT) in uterine and colorectal carcinoma. (f) Heatmap of integral survival (left=resistant, right=sensitive) and gene mutations in uterine and colorectal carcinoma cells. Black bar represents a mutation in the corresponding gene.

DETAILED DESCRIPTION

Figure 1A:
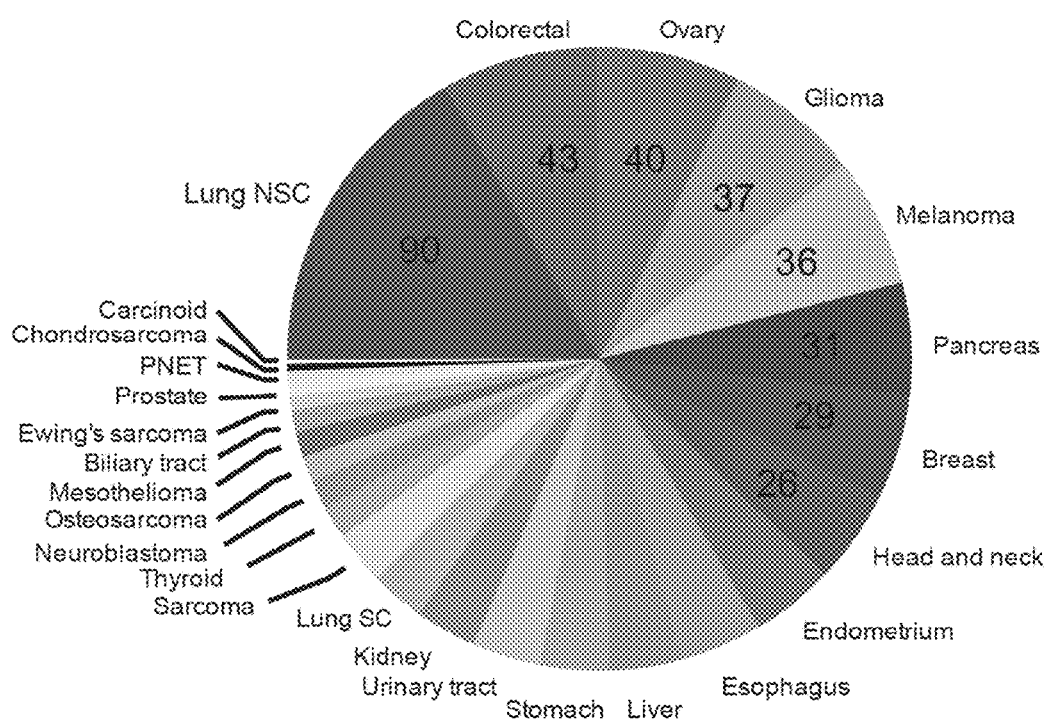
FIGS. 1A-1E. Variation in cancer cell line survival after radiation-induced damage. (a) Distribution of cancer types profiled by lineage. (b) The high-throughput platform accurately profiles cancer cell lines. Integral survival was calculated for each cell line profiled by the high-throughput platform [n=1 (top), n=2 (bottom)] and by clonogenic survival measurements (n≥2). Scatter plots, linear regression, and $R^2$ values were calculated comparing the integral survivals of the high-throughput platform to clonogenic survival. Data are expressed as the means±s.e.m. (c) Integral survival is displayed by column scatter plot separated by lineage and histology where appropriate. HGG, high-grade glioma. LUSC, lung squamous cancer, LULC, lung large cell, SCLC, small-cell lung cancer, PNET, primitive neuroectodermal tumors. (d) Histogram, probability density function, and Normal Q-Q plots analyses of calculated integral survival of 533 cell lines ("All"), 89 non-small cell lung cancer cell lines ("NSCLC"), and 39 lung adenocarcinoma cell lines ("LUAD"). (e) Correlation of response between radiation and compounds. Spearman correlation coefficient was calculated between integral survival values after exposure to radiation or 481 compounds. Correlation was then plotted relative to correlation rank. Some chemotherapeutic agents in clinical use are shown.

Provided herein are compositions, systems, kits, and methods for treating cancer in a subject with androgen receptor positive cancer cells by sensitizing such cancer cells with anti-androgen receptor therapy (e.g., Enzalutamide or anti-androgen antibody), and then treating with radiation therapy.

In certain embodiments, androgen receptor (AR) is tested in a subject's cells to determine if and/or what level of AR is expressed prior to any anti-AR treatment and radiation therapy. The present disclosure is not limited by the type of assay that is employed for such AR detection. In certain embodiments, the AQUA approach is used for measuring AR receptor levels in the nucleus of breast cancer test spots on a tissue microarray. AR clone Dako AR441 was used may be used as the antibody. In other embodiments, the MARS assay is employed (e.g., Dennis et al., Cytometry Part A, 73A: 390-399, 2008, herein incorporated by reference for such assays). In some embodiments, an ELISA type assay is employed to detected Androgen receptor level (e.g., Androgen Receptor ELISA Kit (ab128498) from ABCAM).

EXAMPLES

Example 1

A Genetic Basis for the Variation in the Vulnerability of Cancer to DNA Damage Radiotherapy is not currently informed by the genetic composition of an individual patient's tumor. To identify genetic features regulating survival after DNA damage, a large-scale profiling of cellular survival after exposure to radiation in a diverse collection of 533 genetically annotated human tumor cell lines was conducted in this Example. It was shown that sensitivity to radiation is characterized by significant variation across and within lineages. Results from this were combined with genomic features to identify parameters that predict radiation sensitivity. Identified were somatic copy number alterations, gene mutations, and the basal expression of individual genes and gene sets that correlate with radiation survival, revealing new insights into the genetic basis of tumor cellular response to DNA damage. These results demonstrate the diversity of tumor cellular response to ionizing radiation and establish multiple lines of evidence that new genetic features regulating cellular response after DNA damage can be identified.

Methods

Cell Line Validation.

Cell lines from the Broad Biological Samples Platform were thawed and tested for survival after irradiation between January 2012 and February 2013. Cells were grown in media (Supplementary Data 1) supplemented with 10% fetal bovine serum (ThermoFisher, MA) and 100 U mL$^{-1}$ Penicillin, 100 µg mL$^{-1}$ of Streptomycin, and 292 µg mL−1 L-Glutamine (Corning, N.Y.). When a reference SNP genotype was available for a cancer cell line through the CCLE project, SNP genotyping was conducted by Fluidigm.[60] 87.8% of the 533 cancer cell lines analyzed were positively matched in this Example to their reference genotype. For cellular validation studies, C4-2 cells were from the laboratory of Karen E. Knudsen (Thomas Jefferson University) and HEC59 cells were from the laboratory of Thomas Kunkel (NIES). The cell lines were cross referenced with the database of cross-contaminated or misidentified cell lines curated by the International Cell Line Authentication Committee and NCBI BioSample and identified six cell lines that could have been contaminated or misidentified: BT20, J82, JHH1, MDAMB435S, MKN7, and RT4. All six of these cell lines were SNP gentoyped and confirmed to match the references genotype.

Cell Culture and Irradiation.

All cultures were maintained at 37° C. in a humidified 5% $CO_2$ atmosphere and tested to ensure absence of Mycoplasma. Plates were treated with γ-radiation delivered at 0.91 Gy min$^{-1}$ with a $^{137}$Cs source using a GammaCell 40 Exactor (Best Theratronics; Ontario, Canada).

Antibody and Reagents.

Anti-AKT (clone C67E7, #4691P, 1:1000), anti-phospo-S473-AKT (clone D9E, #4060P, 1:1000), anti-AR (clone D6F11, #5153, 1:2000), anti-HDAC1 (clone 10E2, #5356, 1:2000), anti-γH2AX (clone 20E3, #9718, 1:2000), anti-actin (clone 8H10D10, #3700, 1:4000), anti-γErbB2 (clone Tyr1248, #2247, 1:1000), and anti-GAPDH (clone D16H11, #5174, 1:4000-7500) were from Cell Signaling Technology (Beverly, Mass.). Anti-HER2 (clone e2-4001, #MS730P0, 1:2000) and anti-ER (clone AB-17, #RB1521PO, 1:1500) were from ThermoFisher (Waltham, Mass.). Anti-γDNP-PKcs (clone S2056, #18192, 1:1000 was from Abcam (Cambridge, Mass.). Enzalutamide was from Selleck (Houston, Tex.). DHT was from Steraloids (Newport, R.I.).

High-Throughput Proliferation Assay.

Cells were plated using a Multidrop Combi liquid handler (Thermo Fisher) in at least quadruplicates for each time point at three cell densities (range 25-225 cells per well) in a white 384-well plate (Corning, N.Y.). Plates were irradiated and at 9 days post-irradiation, media was aspirated and 40 µL of CELLTITER-GLO reagent (50% solution in PBS) (Promega, WI) was added to each well. Relative luminescence units were measured using an Envision multilabel plate reader (Perkin Elmer) with a measurement time of 0.1 seconds. Luminescence signal is proportional to the amount of ATP present. For chemical radiosensitization measurements, drug was added 24 hours prior to irradiation. The luminescence signal was plotted as a function of cell density and a cell density within the linear range for luminescence (or growth) was selected to generate integral survival for each cell line.

Integral Survival.

The area under the curve was estimated by trapezoidal approximation. First, X-axis values representing radiation doses 1, 2, 3, 4, 5, 6, 8, and 10 Gy were log 2 transformed. The survival values for each trapezoid were multiplied by the dose interval, $[f(X_1)+f(X_2)/2]*\Delta X$, summed and re-scaled by multiplying by $(7 \div \log_2 10)$ so that integral survival is defined from 0 (completely sensitive) to 7 (completely resistant).

Clonogenic Survival.

Cells were plated at appropriate dilutions, irradiated, and incubated for 7-21 days for colony formation. For chemical radiosensitization measurements, drug was added 24 hours prior to irradiation. Colonies were fixed in a solution of acetic acid and methanol 1:3 (v/v) and stained with 0.5% (w/v) crystal violet as previously described[61]. A colony was defined to consist of 50 cells or greater. Colonies were counted digitally using ImageJ software as described[62].

Integration of survival as a function of dose, or area under the curve, was calculated using Prism, GraphPad Software (La Jolla, Calif.).

Information-Based Association Score.

The association between genomic alterations (e.g. mutations or SCNA) or ssGSEA profiles for each gene set and the radiation response profile was determined using the Information Coefficient (IC)[2, 63, 64].

Genetic Data.

Cancer cell lines were profiled at the genomic level. Briefly, mutation information was obtained both by using massively parallel sequencing of >1,600 genes and by mass spectrometric genotyping (OncoMap 3.0), which interrogated 381 specific mutations in 33 known oncogenes and tumor suppressors. Genotypes were transformed to categorical values (mutation=1, no mutation=0) and were used as input to compute the IC. Genotyping/copy-number analysis was performed using Affymetrix Genome-Wide Human SNP Array 6.0. Raw Affymetrix CEL files were converted to a single value for each probe set representing a SNP allele or a copy number probe using a GenePattern pipeline[66] and hg18 Affymetrix probe annotations. Copy numbers were then inferred based upon estimating probe set specific linear calibration curves, followed by normalization by the most similar HapMap normal samples. Segmentation of normalized log 2 ratios (specifically, log 2(CN/2)) was performed using the circular binary segmentation (CBS) algorithm[67], followed by median centering of the segment values to a value of zero in each sample. Next, quality checking of each array was performed, including visual inspection of the array pseudo-images, probe-to-probe noise variation between copy-number values, confidence levels of Birdseed[68] genotyping calls, and appropriate segmentation of the copy-number profiles. Finally, the Genomic Identification of Significant Targets in Cancer (GISTIC) algorithm[69] was used to identify focal regions of copy number alterations in individual samples. A gene-level copy number was also generated, defined as the maximum absolute segmented value between the gene's genomic coordinates, and calculated for all genes using the hg18 coordinates provided by the refFlat and wgRna databases from UCSC Genome Browser. Separate binary variables representing amplifications (above 0.7) and deletions (below −0.7) were generated based on the GISTIC gene-level copy number output described above. These binary amplification/deletion variables for each gene were used as input to compute the IC against the drug sensitivity phenotype. mRNA gene expression was measured by the GeneChip Human Genome U133 Plus 2.0 Array. Raw Affymetrix CEL files were converted to a single value for each probe set using Robust Multi-array Average (RMA) and normalized using quantile normalization. Either the original Affymetrix U133+2 CDF file or a redefined custom CDF file (ENTREZG-v15) was used for the summarization. ssGSEA enrichment scores were calculated based on the weighted difference of the Empirical Cumulative Distribution Functions of the genes in the set relative to the genes not included in an individual set[34]. The result is a single score per cell line per gene set, transforming the original dataset into a more interpretable higher-level description. Gene sets were obtained from the C2 sub-collection of the Molecular Signatures database (MSigDB)[70], an additional collection of oncogenic signatures, and other cancer-related gene sets curated from the literature, resulting in a dataset that has 4,628 pathway profiles for each sample. ssGSEA values were used as input to compute the IC The nominal p-values for the information based association metric scores between the genetic parameters (alterations or ssGSEA scores) and radiation response scores were estimated using an empirical permutation test.

NFE2L2 Pathway Signatures.

For the gene transcription signature of pathway NFE2L2 (or NRF2), the expression values from the CCLE dataset were extracted. For each gene, expression valued were normalized to standard deviations from the median across cell lines. The average normalized expression of the signature genes was computed within each cell line in which data was available. Across the cell lines, the gene signature scores were normalized to standard deviations from the median across CCLE, and a "summary score" for each pathway was computed as the average of the individual normalized signature scores.[71]

Comet Assays

Single-cell gel electrophoresis was conducted in alkaline or neutral buffer according to the manufacturer's instructions, Trevigen (Gaithersburg, Md.). Slides were blinded and enumerated by a single user.

Western Blot Analysis.

Whole cell lysates were prepared using M-PER lysis buffer and clarified by centrifugation. Proteins were separated by SDS-PAGE and transferred onto 0.45 µM nitrocellulose membranes (Maine Manufacturing; Sanford, Me.). After primary antibody incubation for 1-2 hours at room temperature, washings, and incubation with secondary antibodies, blots were developed with a chemoluminescence system (Amersham/GE Healthcare). For γH2AX measurements, proteins were transferred onto 0.2 µM nitrocellulose (Bio-Rad).

Mouse Xenograft Studies.

Female NSG mice, 6-8 weeks of age, were obtained from the Cleveland Clinic Biological Resources Unit facility. All mouse studies were conducted under a protocol approved by the Cleveland Clinic Institutional Animal Care and Use Committee MDAMB453 cells were resuspended in serum free media and injected into the inguinal mammary gland. Once tumors reached 200 mm$^3$, mice were block randomized and assigned to vehicle, enzalutamide, vehicle plus radiotherapy, or enzalutamide plus radiotherapy. Two cohorts consisting of these four arms underwent treatment. Vehicle consisted of a volume of 5 mL per kg of PEG-400 solution containing 1.5%/0 of DMSO for cohort 1 and 2.5% DMSO for cohort 2 via oral gavage daily. Cohort 1 received enzalutamide at 15 mg kg$^{-1}$ and cohort 2 received enzalutamide at 25 mg kg$^{-1}$. Radiotherapy was delivered to a dose of 1.5 Gy in three fractions once tumor size reached 250 mm$^3$. Treatment was not blinded to the investigator. Tumor volume was measured daily. Mice were sacrificed once their tumors reached an approximate size of 1,000 mm$^3$ or at treatment days 21-28. The significance of the difference between treatment groups was assessed by one-way and the interaction between drug and radiation was measured by two-way ANOVA.

Results

Variation in Survival after Irradiation

Figure 1B:
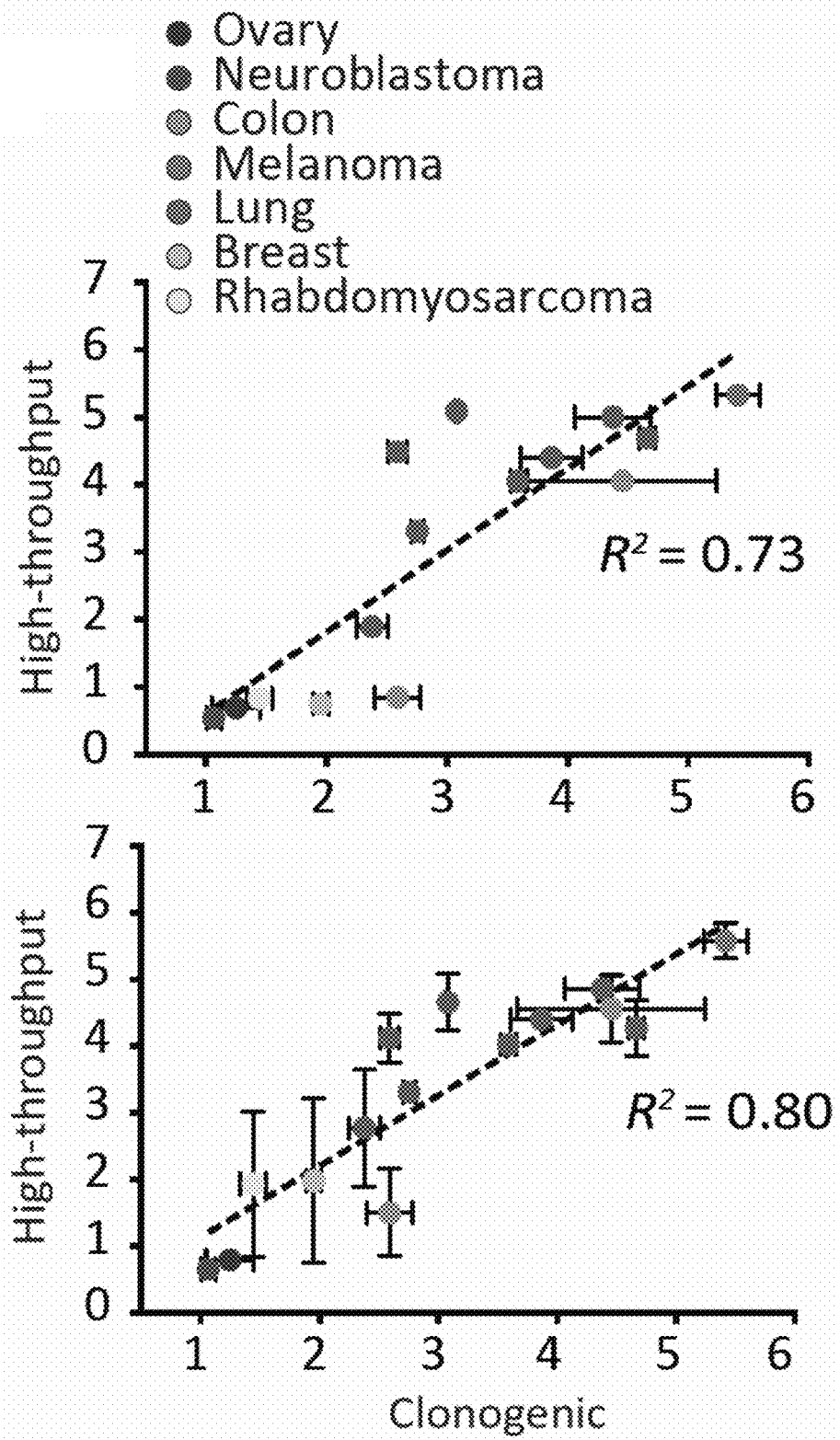
Figure 7:
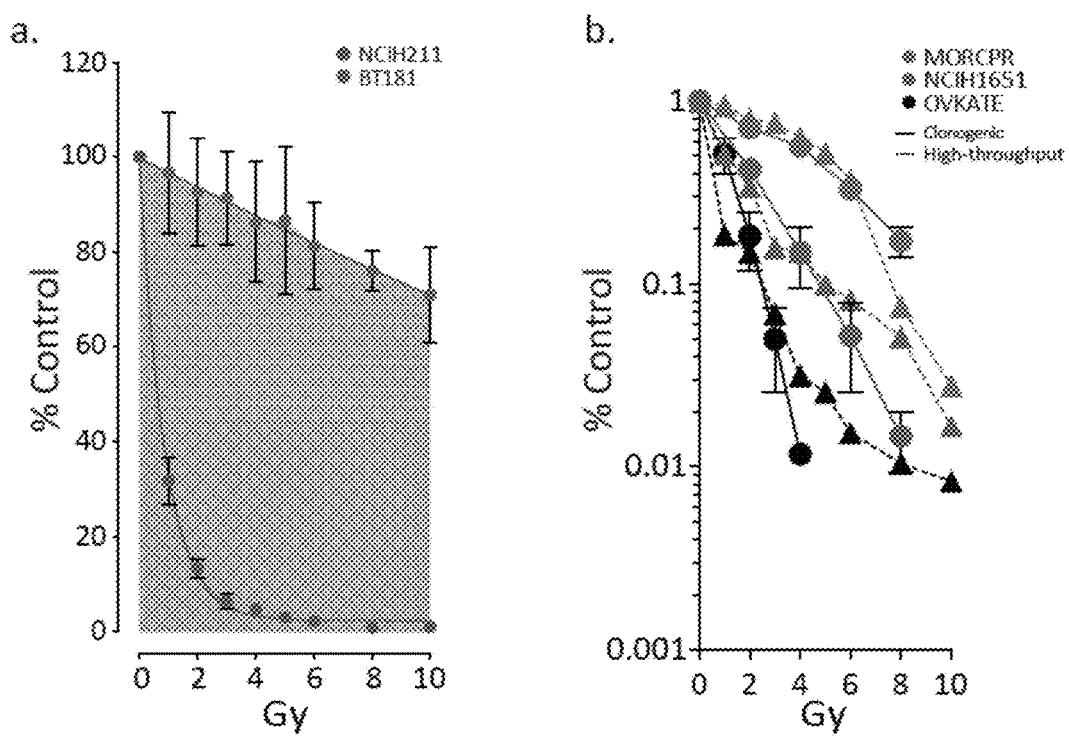
FIG. 7. High-throughput profiling of survival after exposure to γ-radiation. (Panel a) Cells were plated in at least 7 wells in a 384-well plate at cell densities ranging from 25-225 cells in 70 µL of media per well for 24 hours and then treated with IR: 0 (mock), 1, 2, 3, 4, 5, 6, 8, or 10 Gy. Luminescence-based detection of cellular ATP, a surrogate measure of cell number, was performed after 9 days after radiation treatment. Proliferation fraction as a function of dose for NCIH211 and BT181 after exposure to γ-rays is shown. Integral survival (shaded area) was estimated by the trapezoidal approximation of area under the curve. Data are expressed as the means±s.d of at least four replicates. (Panel b) Correlation between high-throughput platform (n=1) and clonogenic survival measurements (n>2) across individual doses. The proliferating fraction (single-run) and clonogenic survival (for each cell line, n>2) were plotted as function of dose. The proliferation index closely approximated clonogenic survival, especially within the $GI_{50}$ range. High-throughput platform data are expressed as the means of at least four replicates. Clonogenic survival data are expressed as the means±s.e.m of at least three experiments.

Radiation survival of 533 cancer cell lines comprising 26 cancer types was profiled using a recently developed high-throughput profiling platform (FIG. 1a)[8]. This platform was previously benchmarked against the clonogenic survival assay in lung squamous cancer cell lines. It was previously demonstrated that the high-throughput measurements closely approximated clonogenic survival by most radiation response parameters, with the greatest level of correlation observed with a longer time to readout, at doses within the GI$_{50}$ range of most cell lines profiled, and when comparing mean integral survival values. To assess the platform's validity beyond lung squamous lineages, clonogenic survival was measured in cell lines derived from multiple lineages and exhibiting a wide range of responses to radiation. Survival as a function of dose was integrated and this generated values for each cell line (FIG. 7 Panel a). Integral survival (single experiment) or mean integral survival values (average of duplicates) for 15 cell lines were calculated and compared to values from the clonogenic assay (for each cell line, n>2) (FIG. 1b). High-throughput and colony integral survival values were significantly correlated, with Pearson r=0.85, $R^2$=0.73 for single experimental profiling and Pearson r=0.89, $R^2$=0.80 with the average of two profiling experiments. It was shown that the proliferation index approximated clonogenic survival across individual doses, with the best approximations occurring within the $GI_{50}$ range (FIG. 7 Panel b).

Figure 1C:
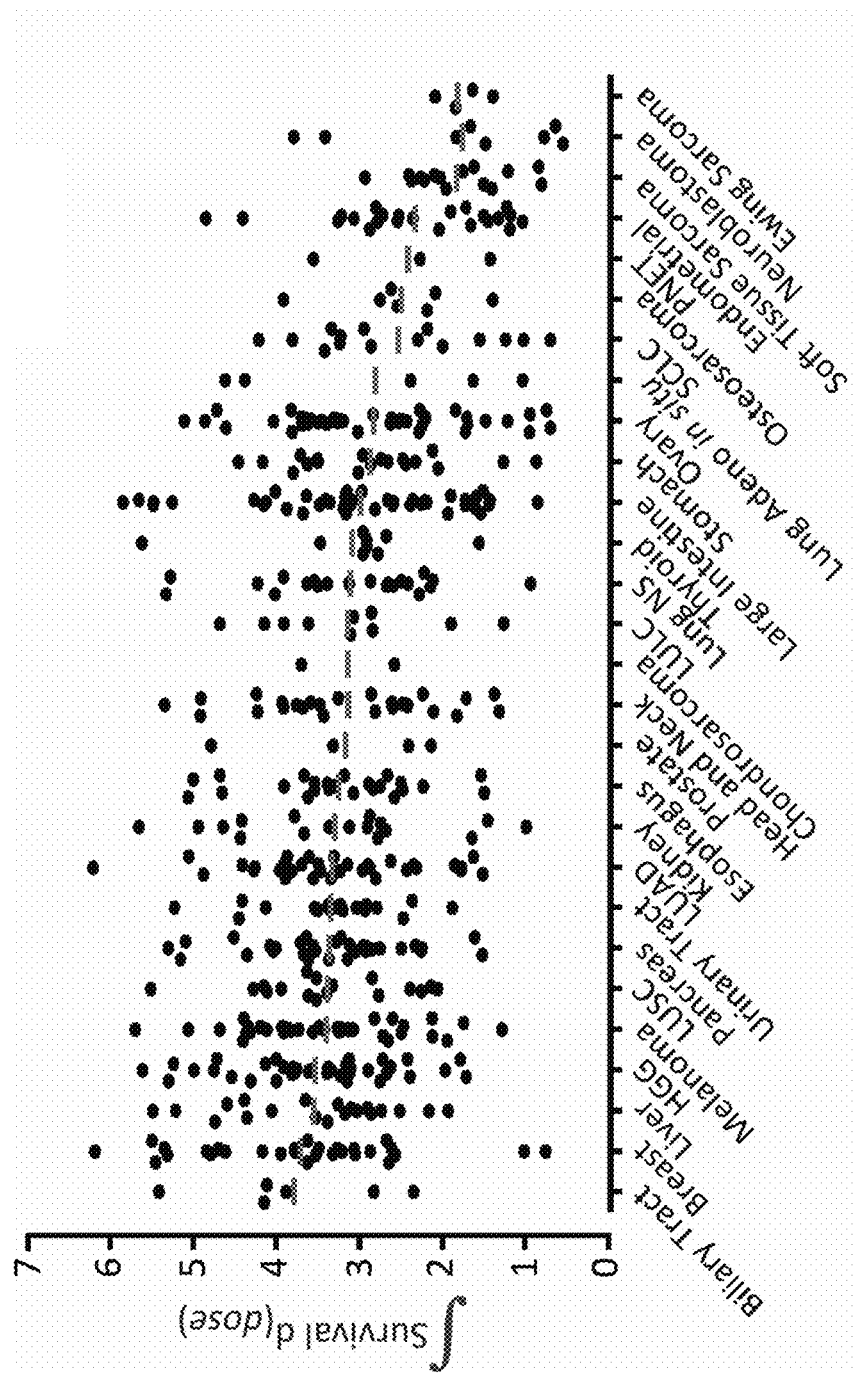
Figure 1D:
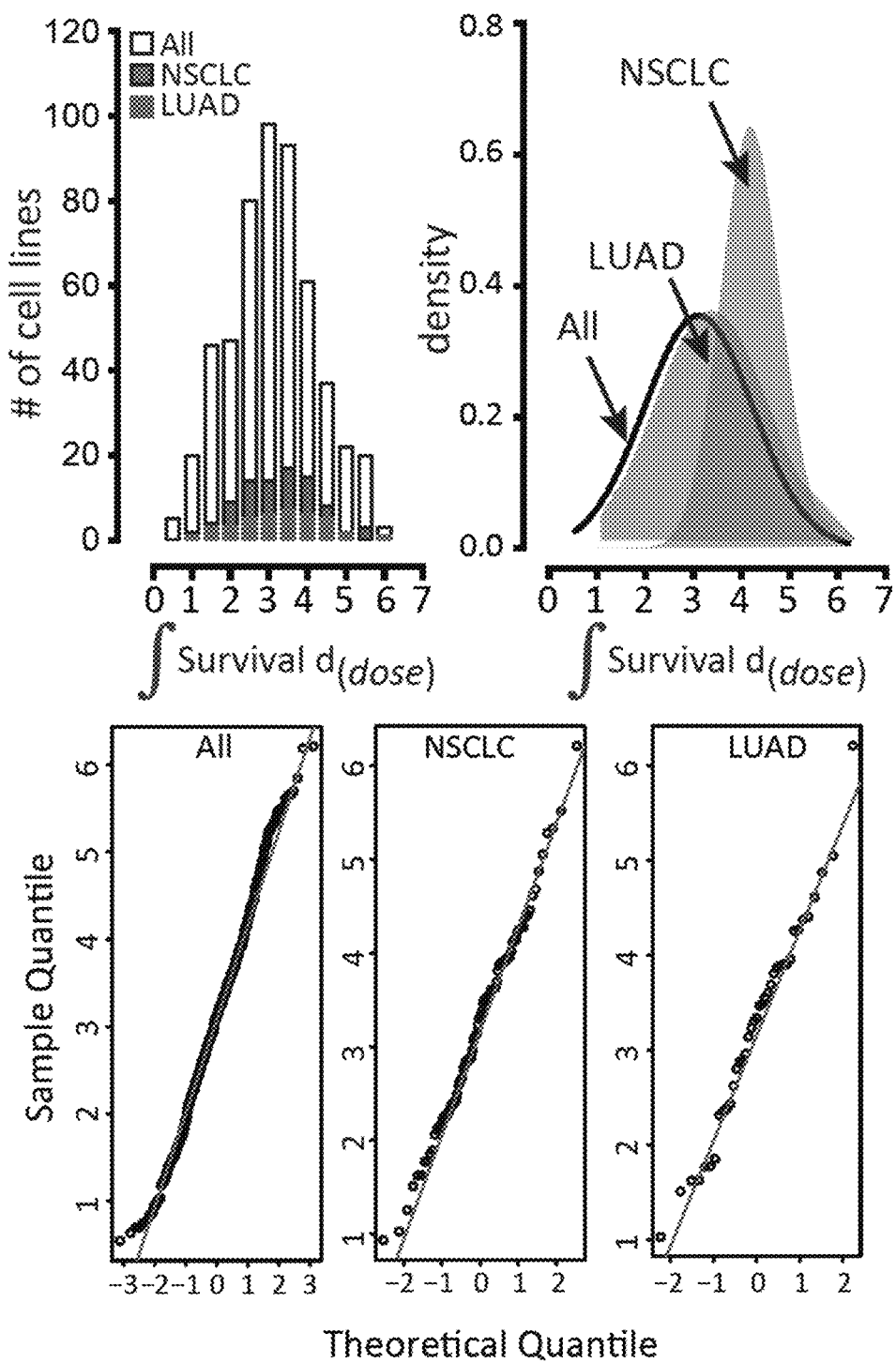
Figure 8:
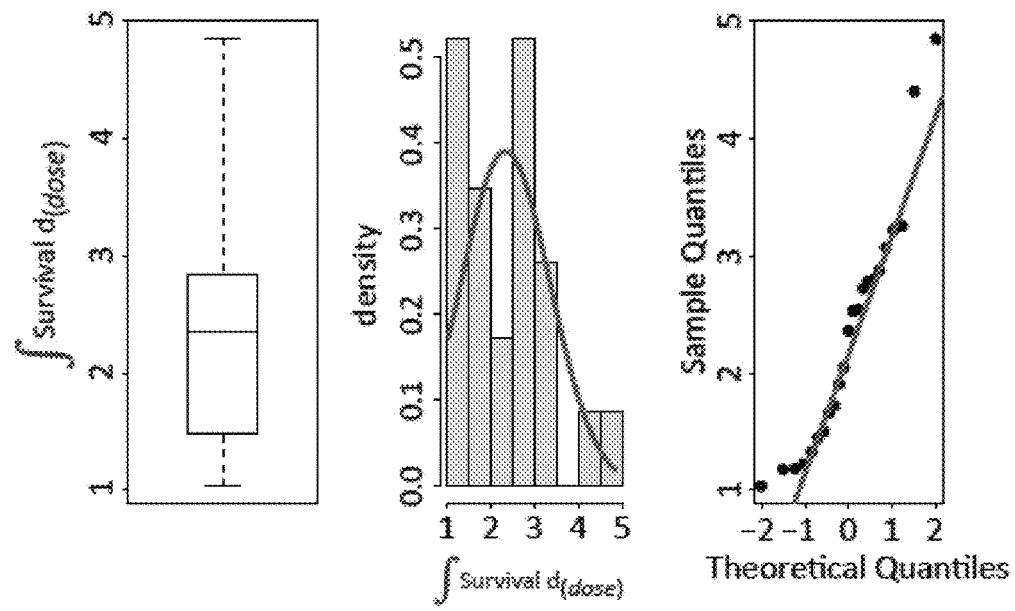
FIG. 8. Non-Gaussian variation in uterine and colorectal carcinoma cell line survival after radiation-induced damage. Box plot and whiskers plots, histogram, probability density function, and Normal Q-Q plots analyses of calculated integral survival for cell lines derived from the uterine and colorectal carcinomas. Whiskers represent minimum and maximum integral survival values in each distribution. The horizontal line in the boxplot represents the median. Histogram analysis of the uterine lineage suggests a bimodal distribution.
Figure 8:
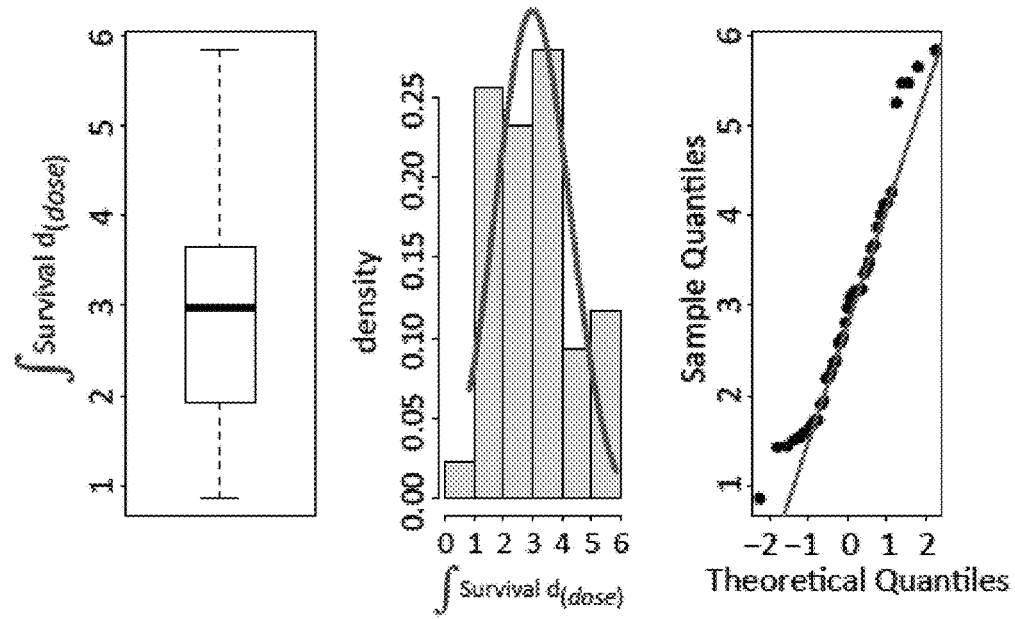
Figure 9A:
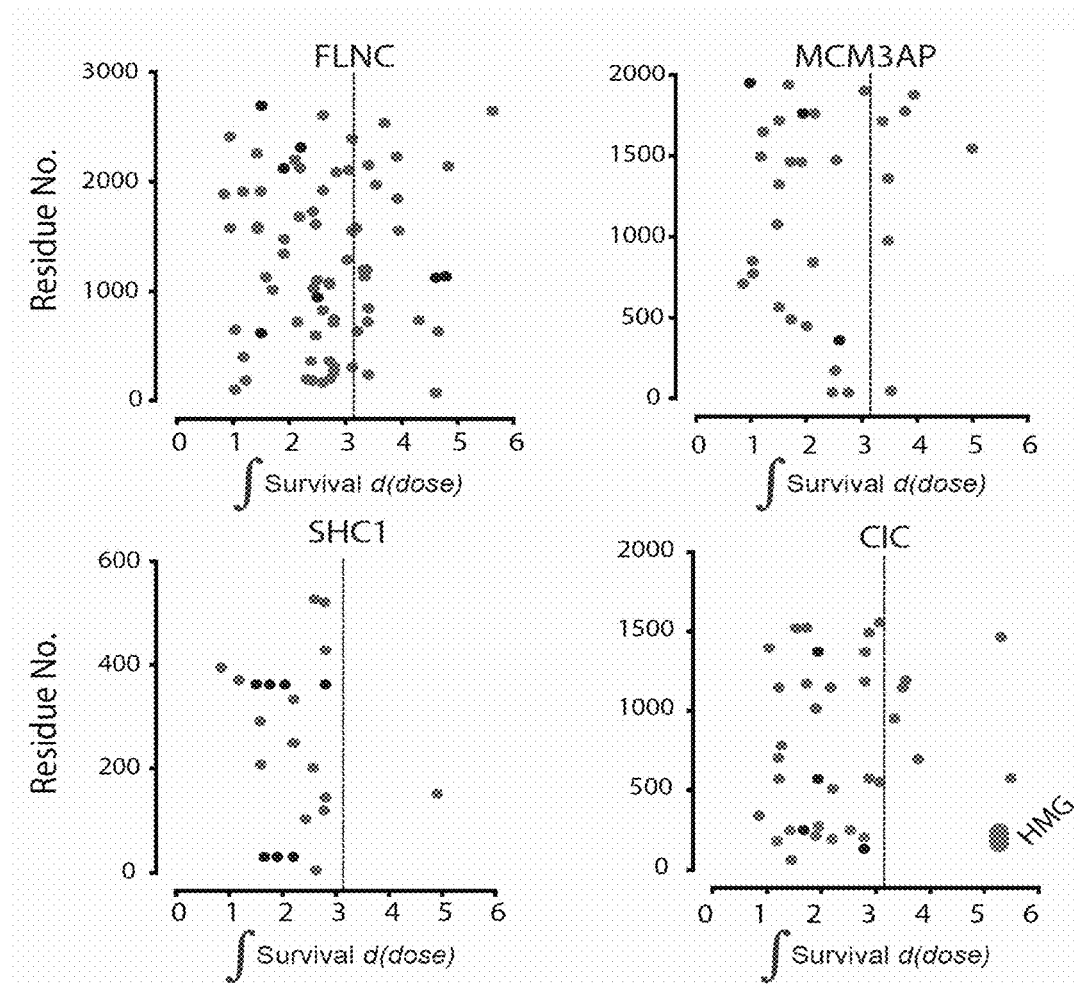
FIGS. 9A-9E. Mutations in a subset of genes associated with radiation sensitivity demonstrate domain-selectivity in conferring sensitivity. Scatter plot of integral survival and amino acid position for cell lines containing mutations in the designated genes. Protein domains predicted by InterPro and/or ExPasy are shown.
Figure 9B:
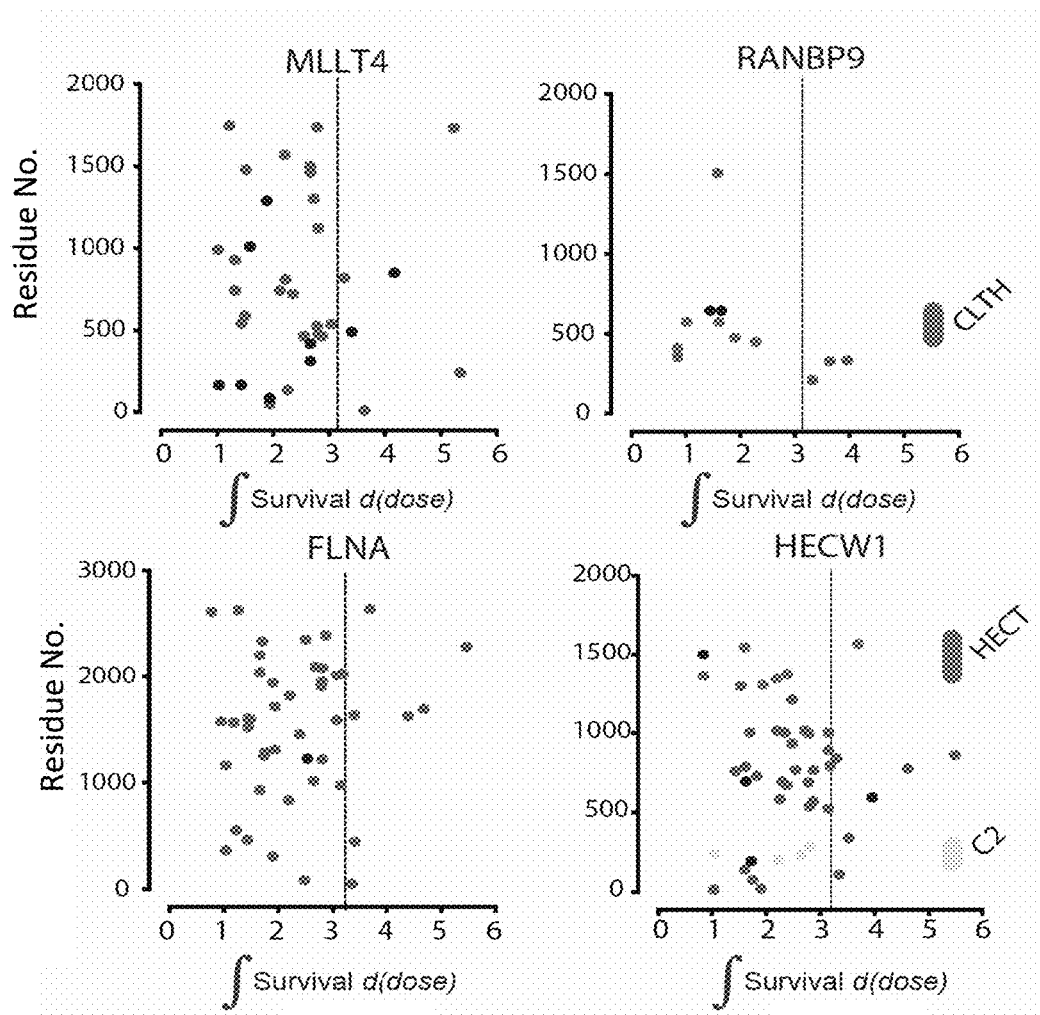
Figure 9C:
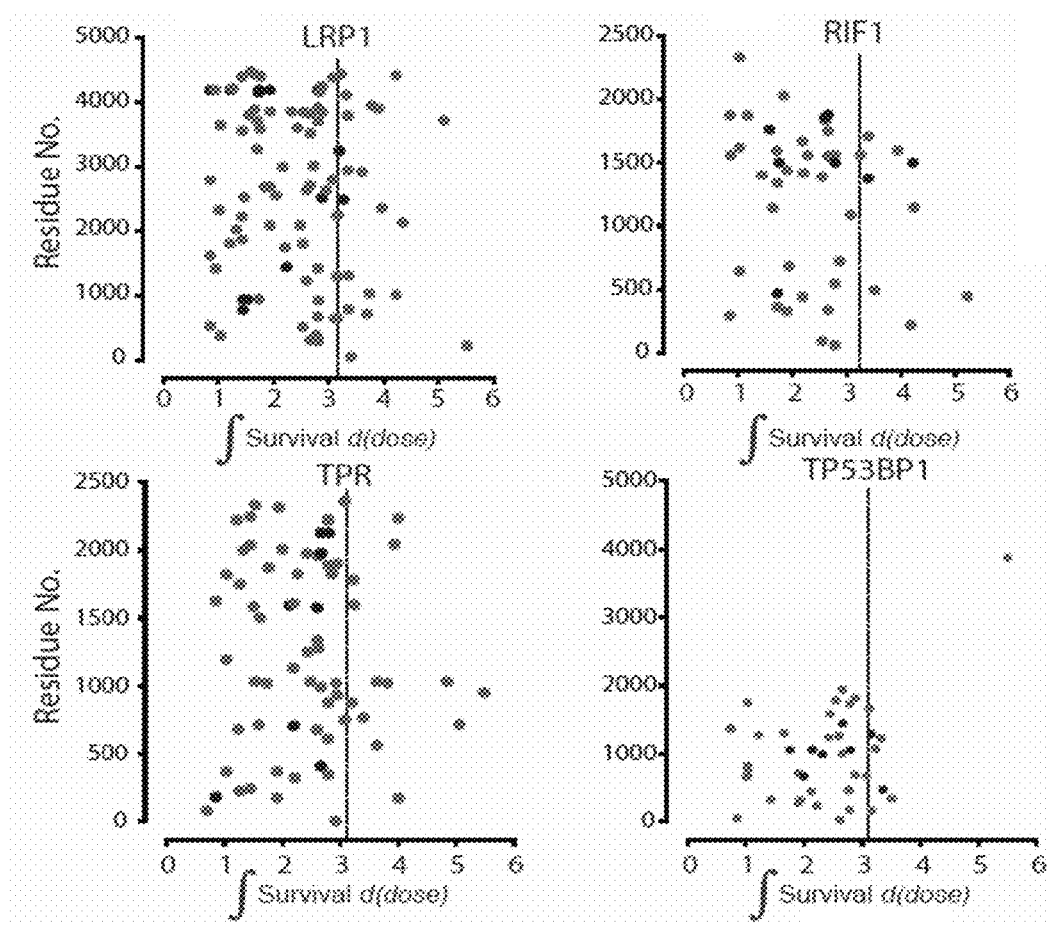
Figure 9D:
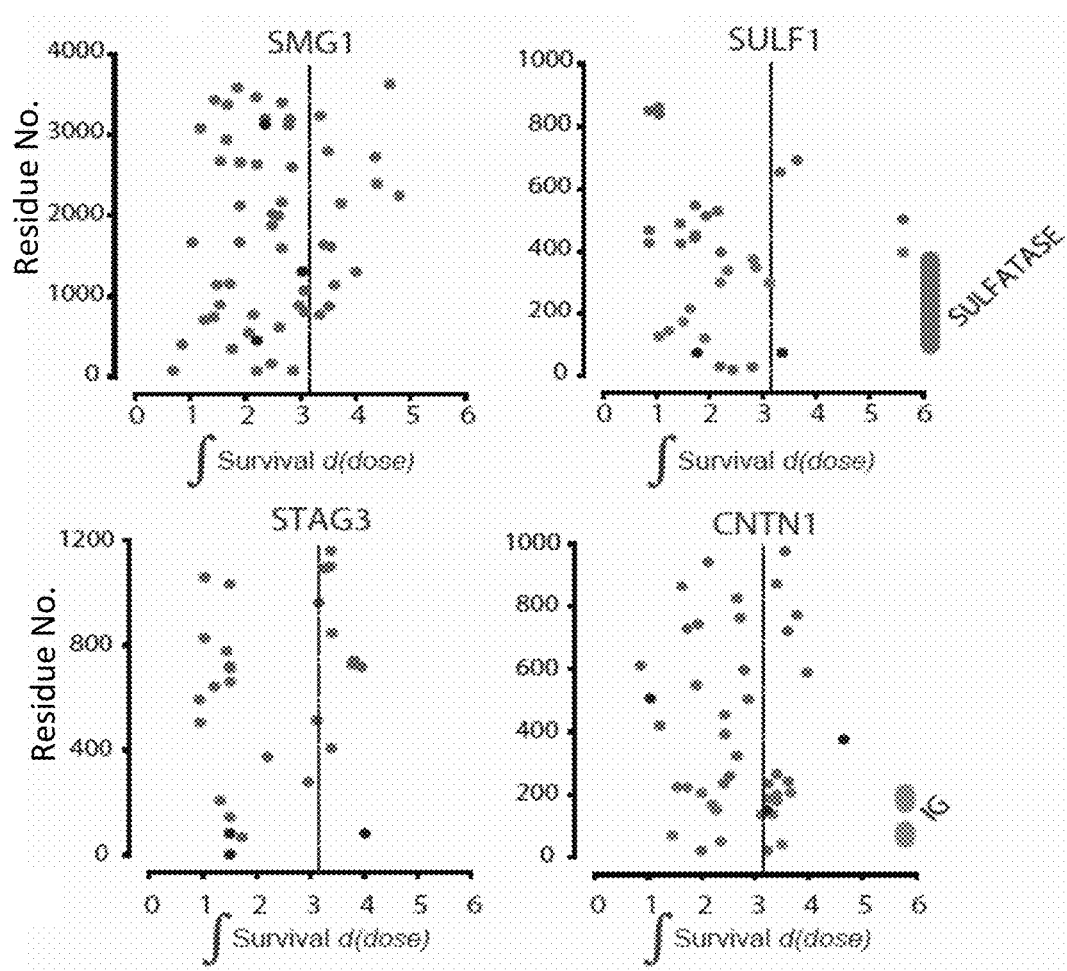
Figure 9E:
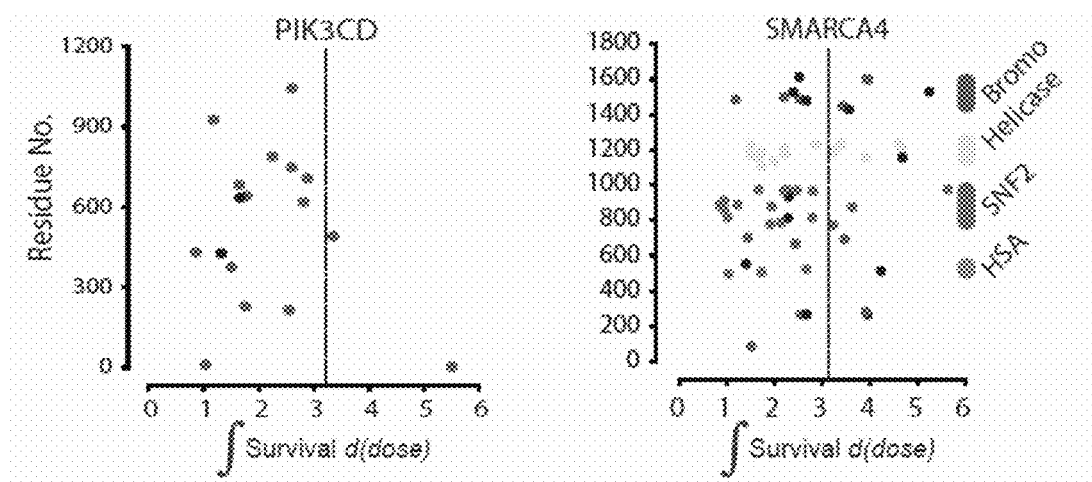

A column scatter plot of integral survival demonstrated significant variation in survival across and within lineages (FIG. 1c), the latter being on the order of 5-7 fold. To assess differences in the distribution of response across all profiled cancer types, in a category of cancers derived from single organ, and in a single lineage, the histogram and probability density distribution of integral survival was plotted for all profiled cell lines, those derived from non-small cell lung cancers, and those from lung adenocarcinoma (FIG. 1d). All three demonstrated a normal distribution. In fact, the majority of lineages (cut-off≥25 cell lines profiled), including lung adenocarcinoma, breast, glioma, ovary, pancreas, and melanoma, were normally distributed (D'Agostino-Pearson: $K^2$<0.65, P>0.5). Only two lineages, colorectal and uterine, demonstrated non-Gaussian distributions, mostly due to a higher proportion of resistant cell lines than predicted by a normal distribution (FIG. 8). This is attributed to cell lines with large values of copy number. Taken together, the high-throughput platform accurately profiles cell lines from multiple lineages for radiation response and reveals a mostly Gaussian distribution of radiation response within lineages.

X-Rays and DNA Damaging Drugs

Figure 1E:
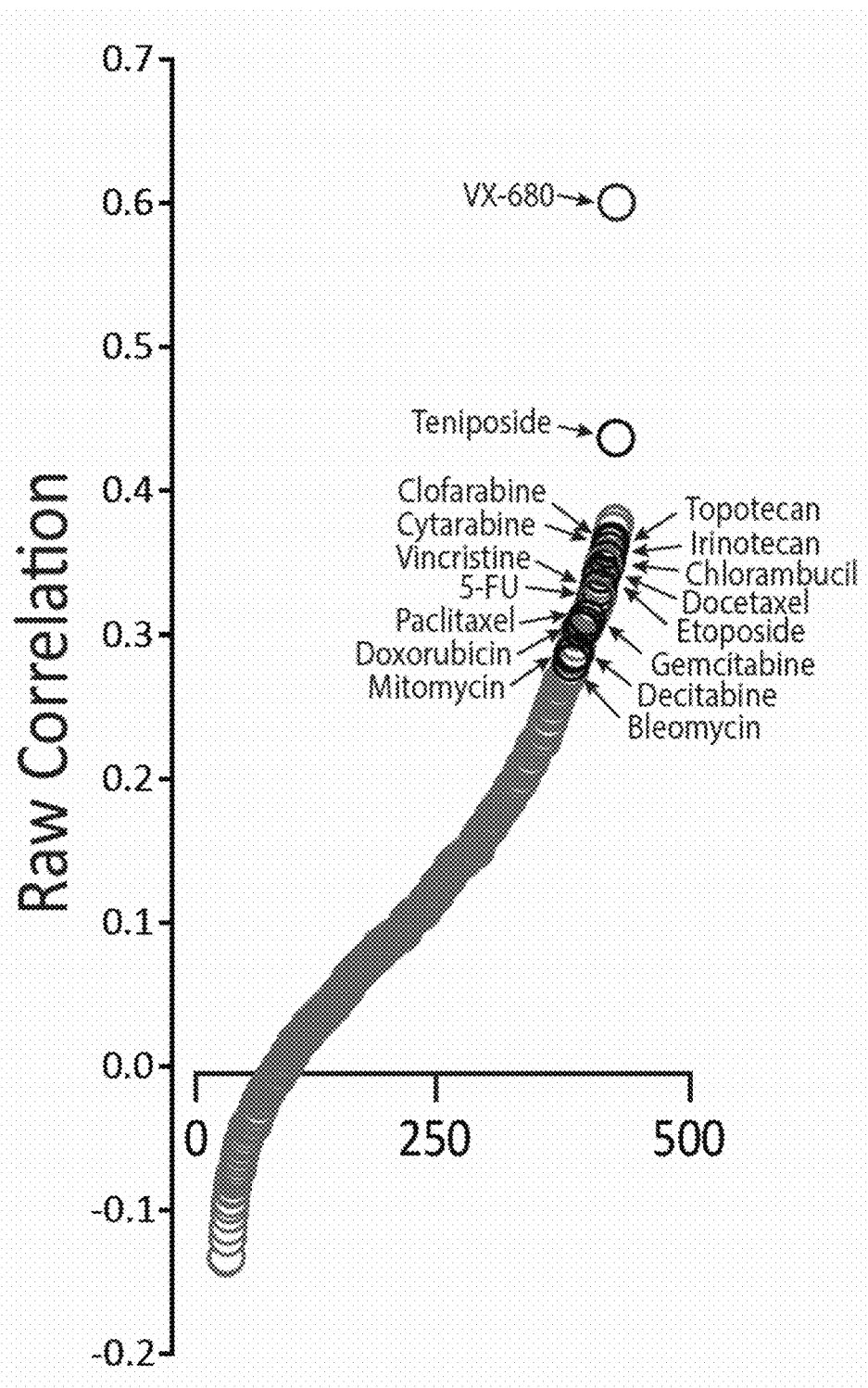

To assess the accuracy of the platform and probe similarities between radiation and drug therapy, the correlation of responses between radiation and 481 compound probes profiled by $CTD^2$ was calculated[9] (FIG. 1e). The most positively correlated compound, VX-680, is a pan-inhibitor of the Aurora kinases (Spearman r=0.60)[10]. Aurora kinases are essential for the regulation of chromosome segregation and cytokinesis during mitosis and their inhibition leads to cell death by mitotic catastrophe, a major mode of cell death after irradiation. In addition to VX-680, genotoxic chemotherapeutics such as etoposide, paclitaxel, doxorubicin, bleomycin, and others were likely to be correlated with radiation sensitivity. These correlations suggest similar genetic dependencies between genotoxic compounds and radiation.

SCNA Regulate Survival after Irradiation

Figure 2A:
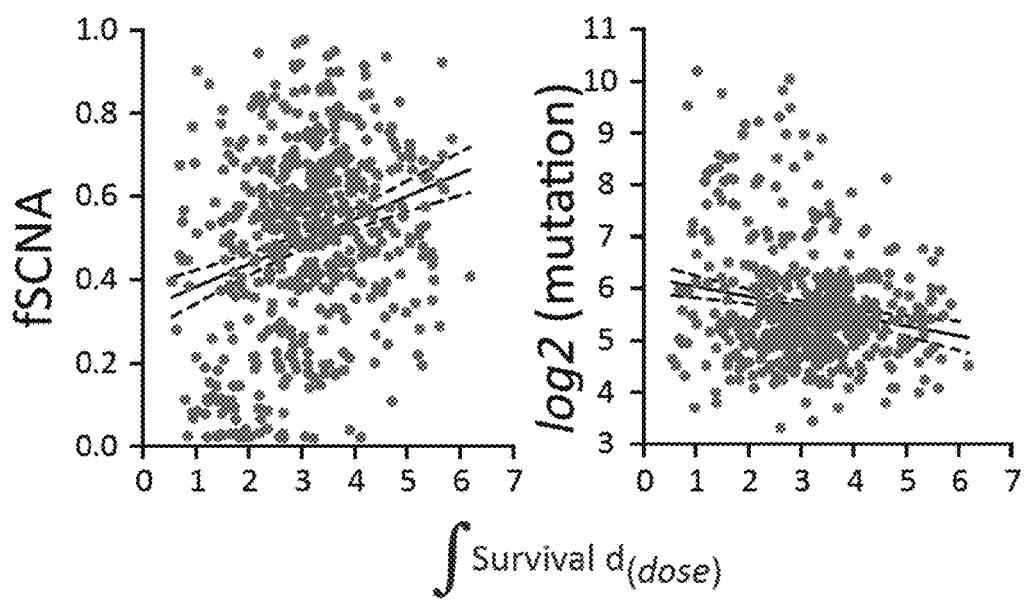

Somatic copy-number alteration(s) (SCNA) are common in cancer[11], have a critical role in promoting oncogenesis[12], and an understanding of their phenotypic effects has led to advances in cancer diagnostics and therapeutics[7, 13, 14]. The interaction between the SCNA landscape and the response to radiation remains poorly defined. The fraction of the genome that contains a SCNA or (fSCNA) was measured by measuring the length of segments with log 2 SCNA values larger than 0.2 from the GISTIC output, divided by the length of all segments measured. Therefore, the fSCNA represents a surrogate measure of genomic instability based on relative SCNA. A positive correlation (Pearson r=0.27) was observed between fSCNA and integral survival (FIG. 2a). The log 2 of the number of mutations was plotted per sample and integral survival and observed a modest negative correlation (Pearson r=−0.19).

Figure 2B:
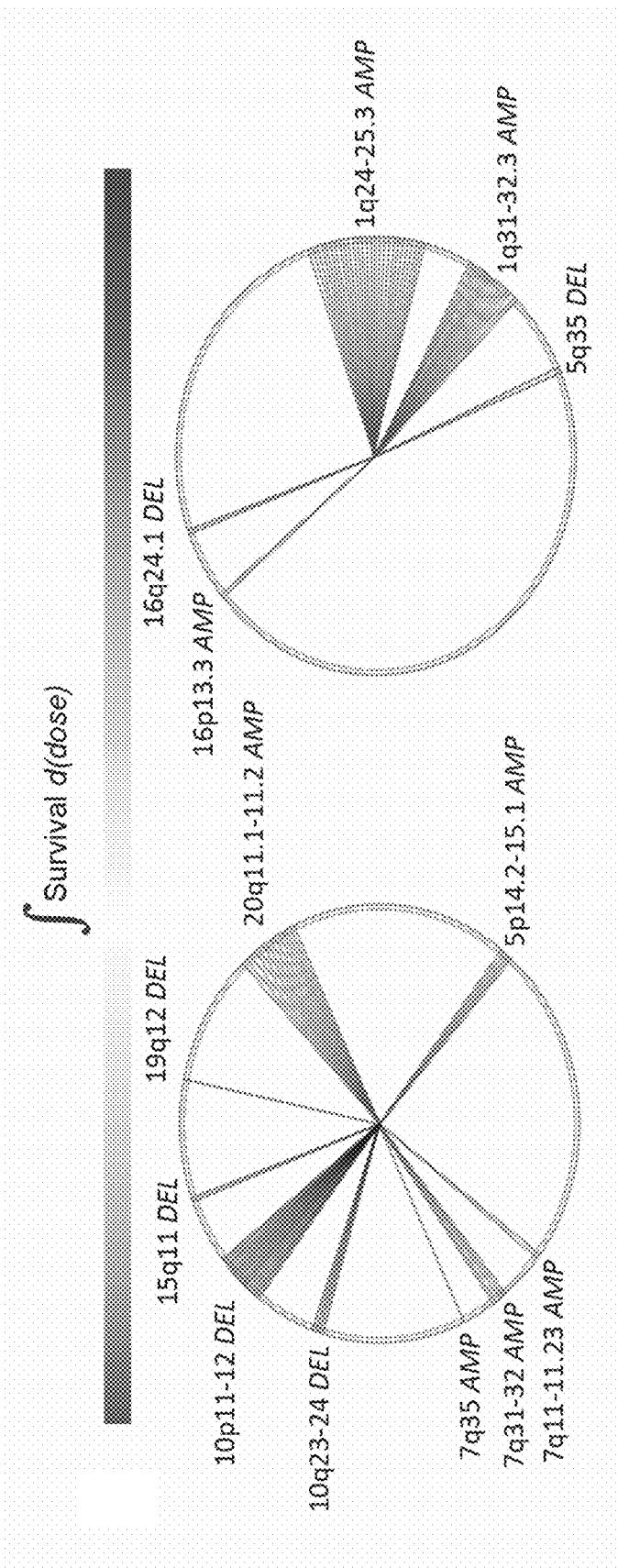
Figure 2C:
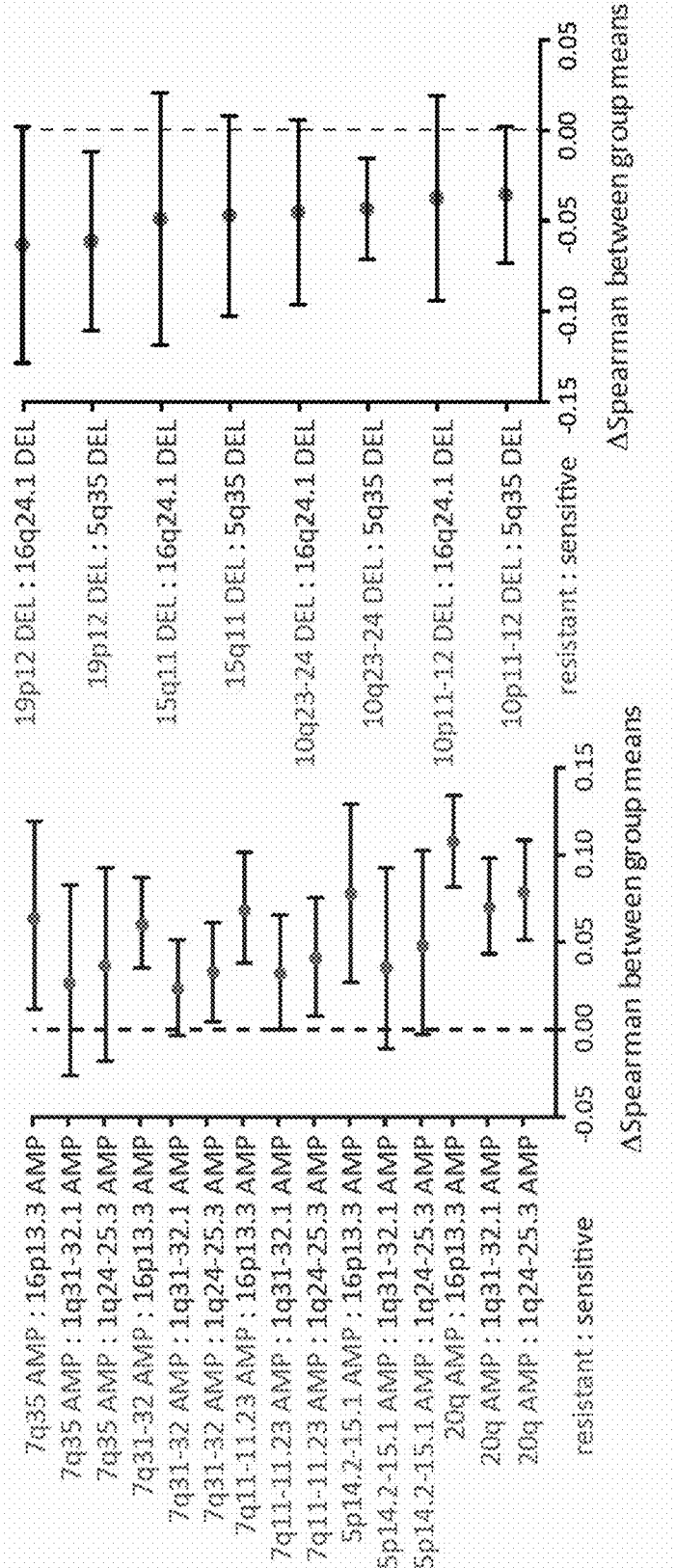

It was reasoned that the overall positive correlation of fSCNA with radiation survival could reflect an increased capability of tumor cells to repair DNA double-strand breaks after radiation, utilizing mechanisms that are also used in the creation of SCNA such as non-homologous or micro-homology mediated end-joining or other error-prone repair mechanisms (e.g. non-allelic homologous recombination)[15]. Alternatively, individual SCNA could regulate survival after radiation by changing the expression of specific genes within the structurally altered chromosomal segments. The former is predicted to create a stochastic order of individual SCNA correlated with survival, the latter would identify discrete SCNA on both sides of the survival spectrum. To assess the association of individual SCNA with radiation response, alterations were correlated with radiation survival using the Information Coefficient (IC). The top 50 gene level SCNA correlating with resistance and sensitivity were organized by chromosome position and the results were depicted using a wheel-plot (FIG. 2b). The relative enrichment for discrete chromosomal segments that correlated with resistance or sensitivity suggested that individual SCNA events were not randomly distributed across the radiation response range. To assess whether SCNA can contribute to radiation response directly, radiation survival was correlated with the expression of genes within the altered segments and compared the means of the coefficients by pair-wise analysis, resistant versus sensitive (FIG. 2c). The amplified regions that correlated with radiation resistance had a significantly higher mean correlation coefficient than amplifications that correlated with radiation sensitivity. The inverse was observed for deleted regions that correlated with radiation resistance. In some cases, changes in the expression of individual genes have previously been implicated in response to cytotoxic stress. For example, genes overexpressed as a consequence of focal amplicon 20q11.2 include functionally important genes in cell cycle regulation (E2F1), chromosome maintenance (KIF3B), glutathione synthesis (GSS), and apoptosis (BCL2L1). All of these genes were positively correlated with radiation resistance. Collectively, these results indicate that SCNA regulate the response of cells to radiation-induced damage in part through direct changes in gene expression.

Figure 2E:
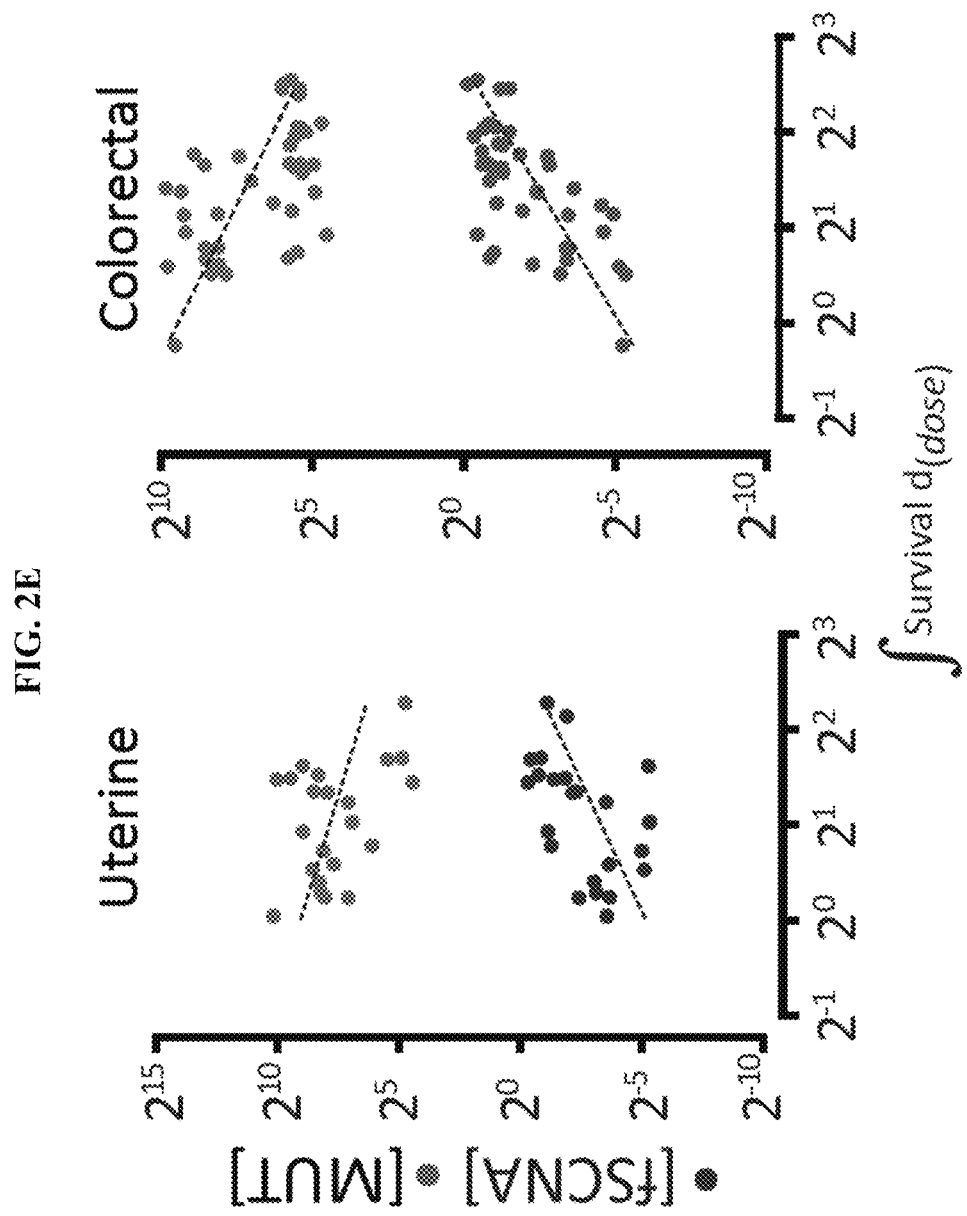
Figure 2F:
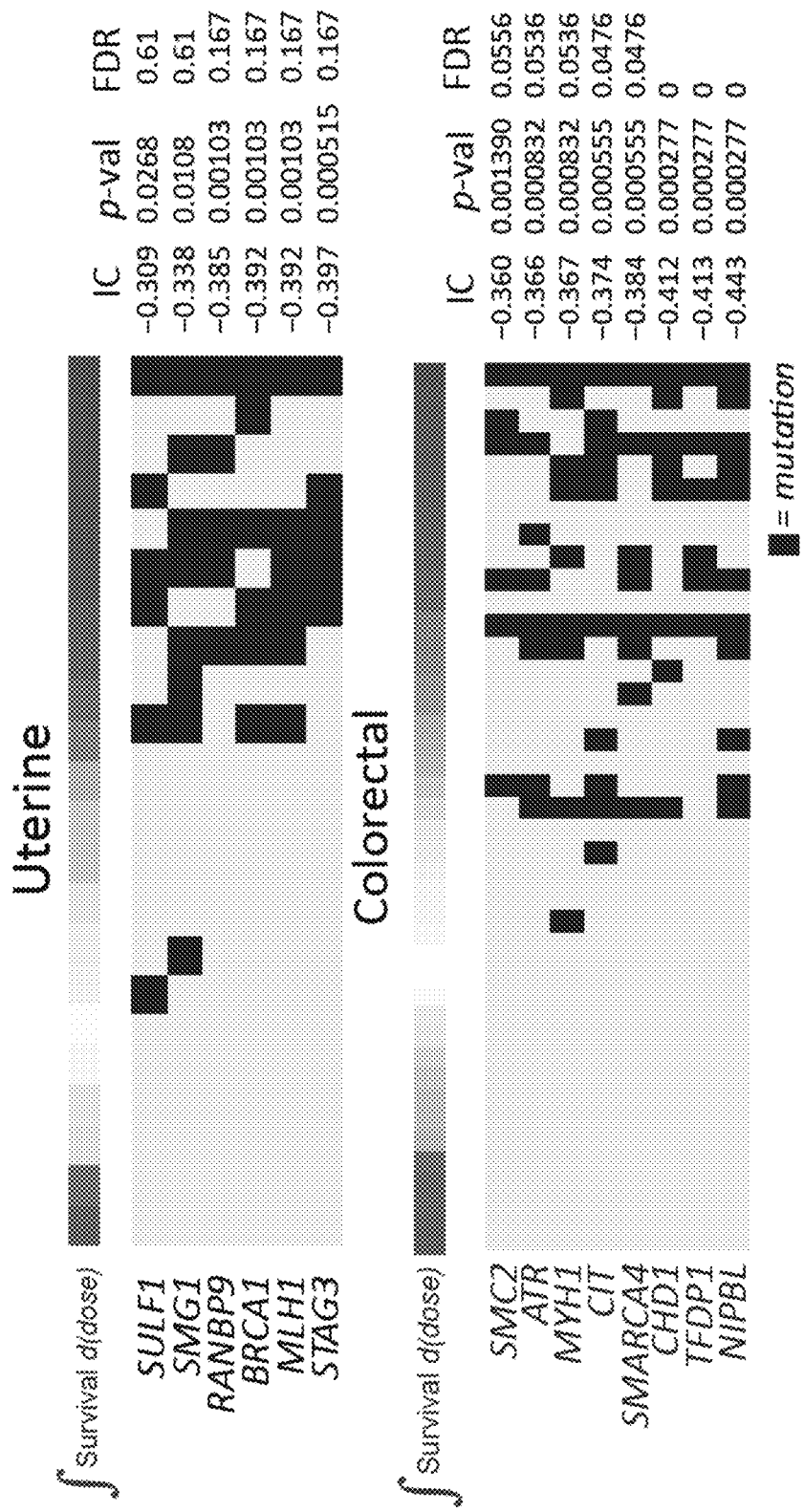

The frequency and distribution of SCNA vary across tumor lineages[12]. A scatterplot of fSCNA and integral survival revealed differences in the degree and direction of association across lineages. Colorectal, uterine and ovarian carcinomas showed a positive correlation between survival and fSCNA values (FIG. 2d). Colorectal and uterine carcinomas have been previously shown to contain tumors with extensive SCNA and low mutation frequency and a subset of tumors with low SCNA and high mutation frequency. The latter is attributed to either MLH1 silencing and/or DNA polymerase ε (POLE) mutations[16, 17]. Consistent with these findings, a correlation was observed between radiation survival and SCNA and an anti-correlation between radiation survival and mutation frequency in both lineages (FIG. 2e). Mutations were identified in individual genes that correlated with radiation sensitivity in both lineages using the IC (FIG. 2f). Of the top 20 genes that correlated with radiation sensitivity in uterine and colorectal cancers, six and eight, respectively, have previously been associated with DNA repair. These results suggest an association between low SCNA, high mutation frequency, DNA repair gene disruption, and radiation sensitivity in these lineages.

Gene Mutations Regulate Cellular Survival after Irradiation

Figure 3A:
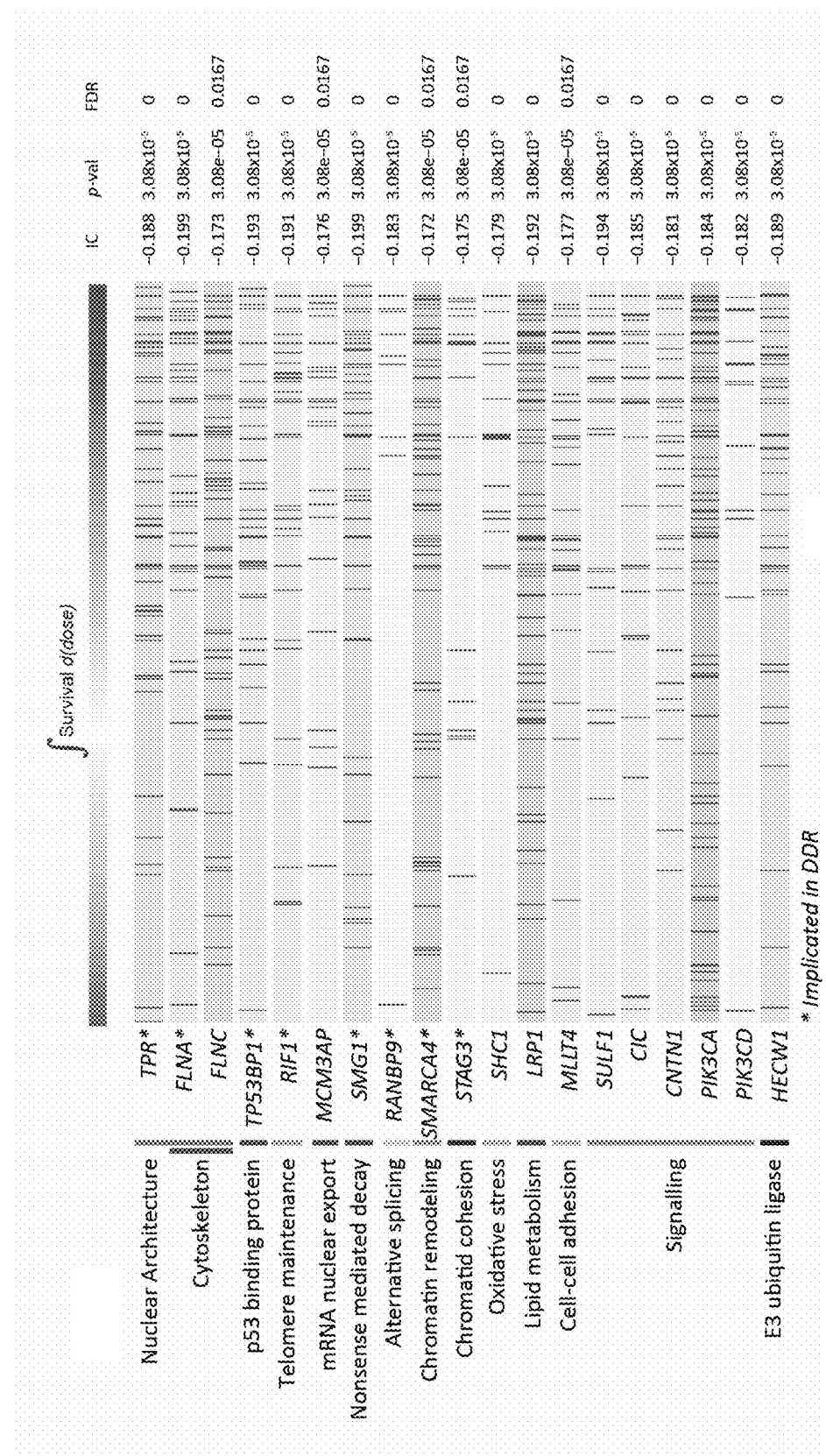
FIGS. 3A-3I. Mutations in genes associated with distinct cellular functions correlate with survival after radiation-induced damage. (a) Top 19 genes that when mutated are associated with radiation sensitivity are organized by biological functions. The bars represent samples with a mutation. (b) Scatter plot of integral survival and amino acid position for cell lines containing mutations in PIK3CA. (c) Association between radiation response and mutation in PIK3CA and PTEN in uterine carcinoma. (d) γAKT, AKT, and GAPDH levels in two uterine cancer cell lines with p85 BD mutations. (e) Frequency of PIK3CA and PIK3CA p85 BD mutations as annotated by TCGA; organized from left to right by frequency of mutations in p85 BD. (f), (i) Scatter plot of integral survival and amino acid position for cell lines containing mutations in KEAP1 and NFE2L2. (g) KEAP1 alteration frequency by lineage, and histology where appropriate, as annotated by TCGA. Organized from left to right by frequency of KEAP1 mutation. (h) Association between integral survival and genomic features in lung adenocarcinoma. Red bar represents a copy-number change or mutation in the corresponding gene.

Recent studies have identified recurrent gene mutations that are correlated with the likelihood of response to specific agents in cancer[4, 5]. Identifying gene mutations that correlate with radiation response have the potential to similarly inform clinical management. Gene mutations were identified that correlated with radiation sensitivity across all lineages using the IC. Higher IC values were observed for genes with mutations and radiation sensitivity compared to resistance. The top 19 genes that were associated with radiation sensitivity when mutated were organized by biological function (FIG. 3a). Seven of these genes have previously been implicated in the DNA damage response: TPR[18], FLNA[19], TP53BP1[20], SMG1[21], RANBP9[22], SMARCA4[23], and STAG3[24]. A subset of the 19 genes demonstrated domain-selectivity in conferring sensitivity (FIG. 9). Other top genes that correlated with radiation sensitivity have not previously been implicated in radiation-induced damage response.

Figure 3B:
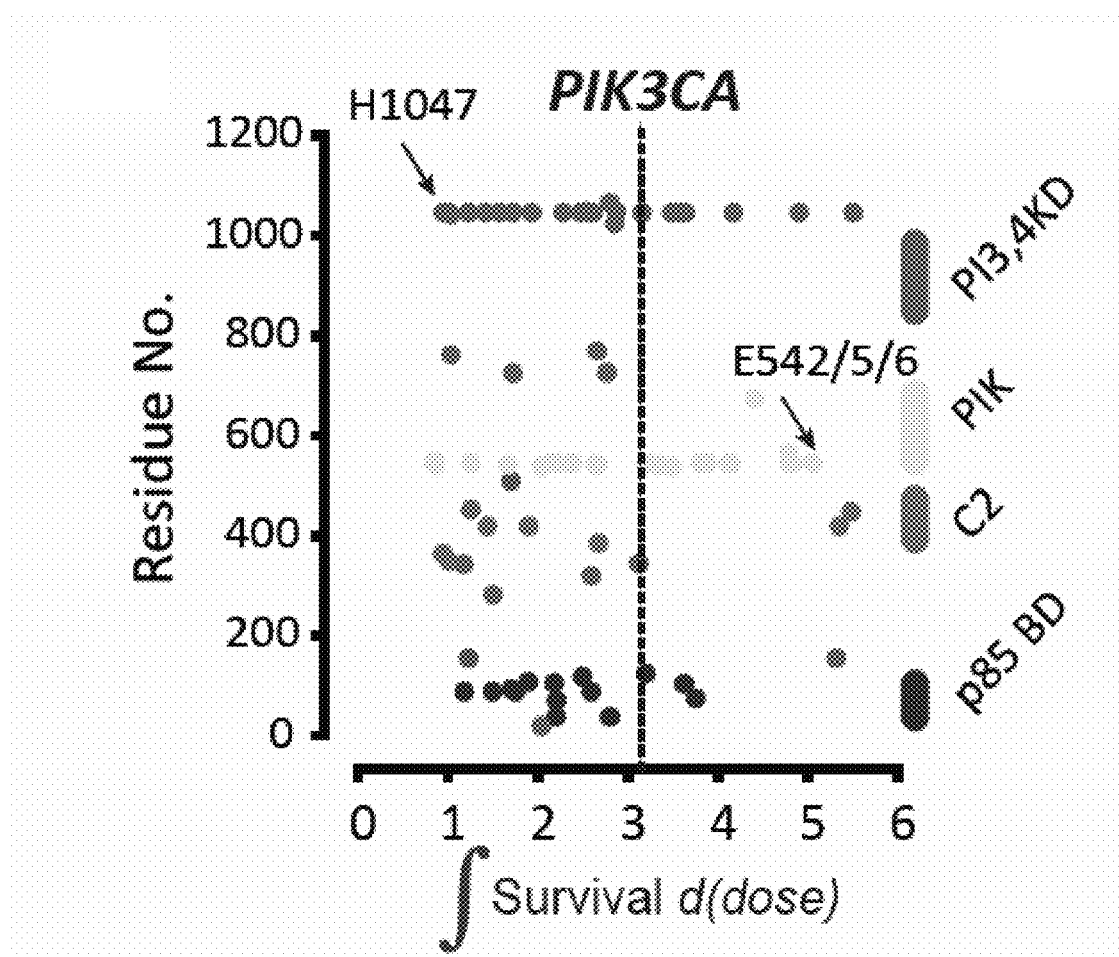
Figure 3C:
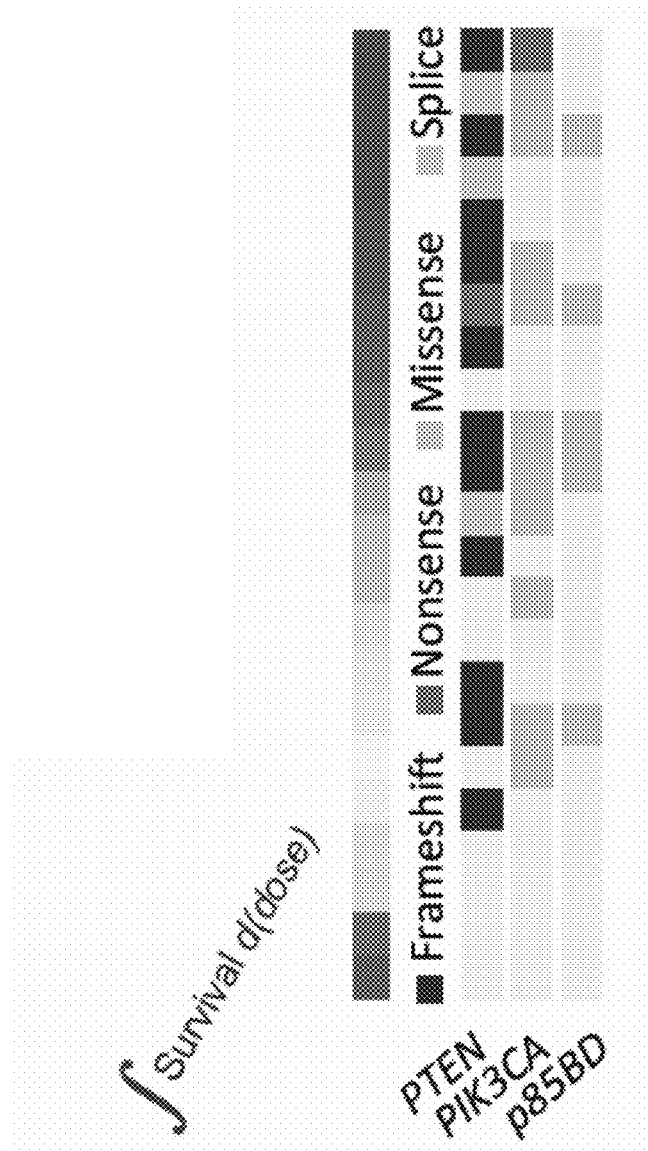
Figure 3D:
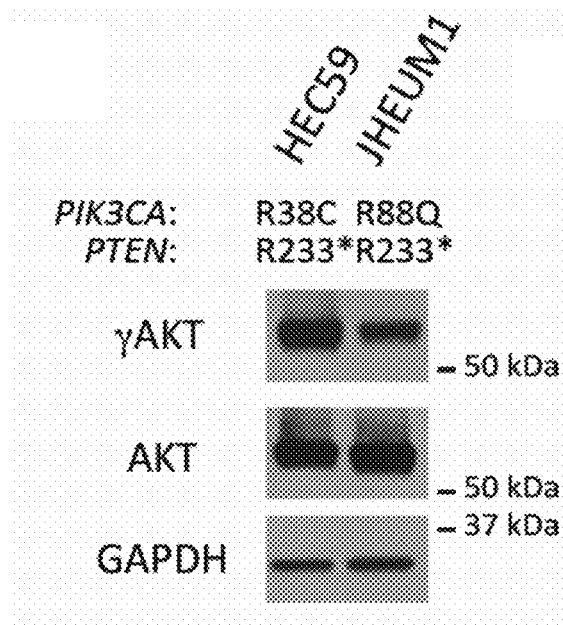
Figure 3E:
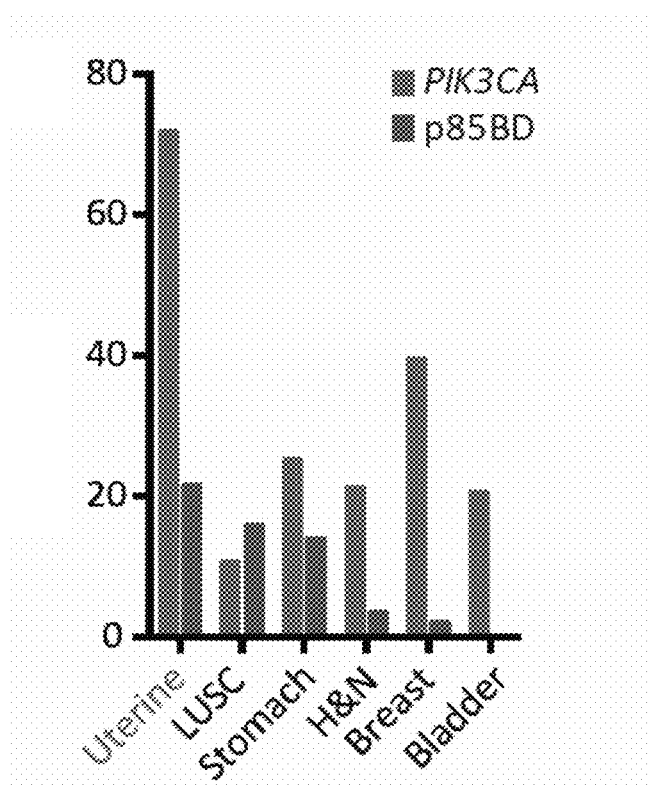

It was sought to determine whether identified genes were regulators of radiation response or merely associated with sensitivity. An example of the latter is PIK3CA. The phosphatidylinositol 3-kinase (PI3K)/protein kinase b (AKT) pathway is frequently deregulated in human cancer and is an important tumor cell survival pathway[25]. Mutations in PIK3CA, which typically result in activation of PI3K/AKT, were associated with radiation sensitivity in the dataset (FIG. 3a). However, activation of PI3K/AKT has previously been associated with radiation resistance[26, 27]. A closer look at the domains within PIK3CA and their role in radiation sensitivity indicates that cell lines with mutations in the p85 binding domain (p85 BD) are mostly sensitive to radiation, driving the overall association (FIG. 3b). Cell lines with mutations in the p85 BD of PIK3CA were largely from the uterine lineage (38% of the cell lines profiled in FIG. 3b), had a co-occurring mutation in PTEN (FIG. 3c), and two representative cell lines were γAKT replete (FIG. 3d), indicating p85 BD mutations retain PI3K enzymatic activity. Mutations in the PIK3CA p85 BD were also frequently identified (>20%) in uterine tumor samples profiled by the The Cancer Genome Atlas (TCGA) network (FIG. 3e), paralleling the cell line data[17]. These results indicate that PIK3CA p85 BD mutations reflect markers of a radiosensitive lineage (uterine carcinoma).

Figure 3F:
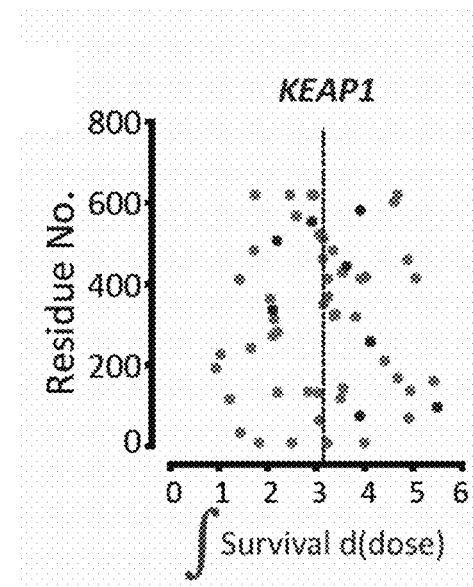
Figure 3G:
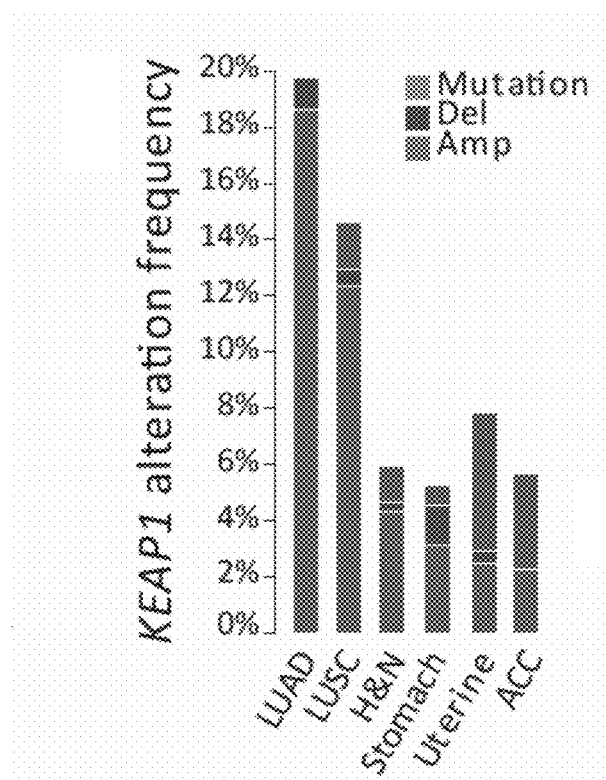
Figure 3H:
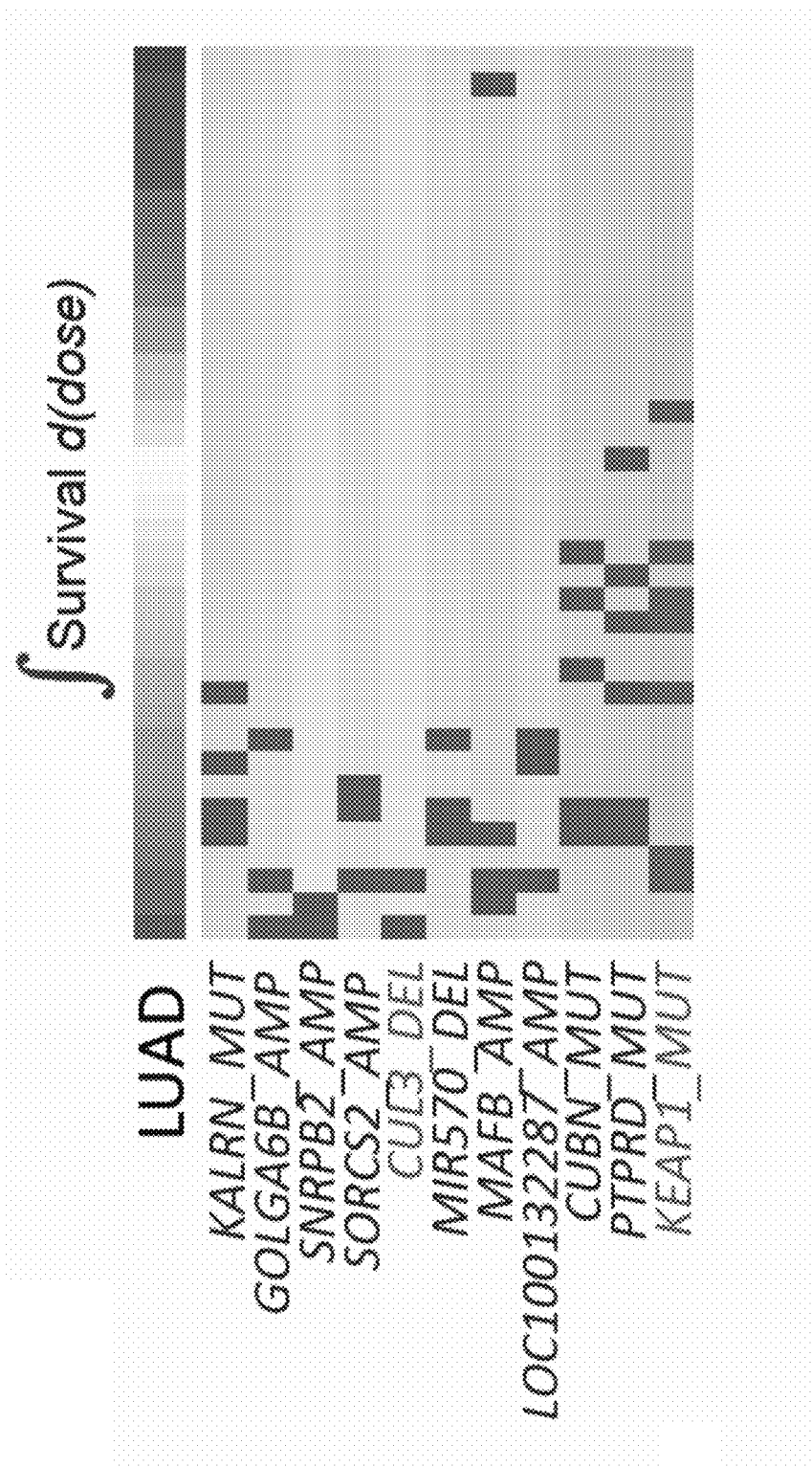

Mutations were analyzed that conferred radiation resistance and identified the key regulator of oxidative stress response, KEAP1, which ranked ninth (IC=0.112; P=0.0513, calculated using the empirical permutation test) from a list of >1600 genes (FIG. 3f). It has been shown that mutations in KEAP1 result in the stabilization and activity of the master transcriptional regulator of oxidative damage response, Nrf2 (encoded by NFE2L2), thereby conferring radiation resistance[8, 28, 29, 30]. Recently, the spectrum of KEAP1 mutations was analyzed, revealing distinct functional categories including passenger, loss-of-function, hypomorphic, or "super-binders"[31]. It was reasoned that the likelihood of passenger or hypomorphic mutations masking association is less likely to occur in a lineage with frequent KEAP1 mutations. To test this, the IC in adenocarcinoma of the lung was analyzed, which has the highest frequency of KEAP1 mutations of any lineage profiled by the TCGA network to date (FIG. 3g)[32]. Consistent with TCGA network data, the strongest association between KEAP1 mutation and radiation resistance was in adenocarcinoma of the lung (IC=0.352; P=0.0224, calculated using the empirical permutation test) (FIG. 3h). CUL3, encoding the ubiquitin ligase adapter that binds to Keap1 and degrades Nrf2, was also associated with radiation resistance in adenocarcinoma of the lung (FIG. 3h).

Figure 3I:
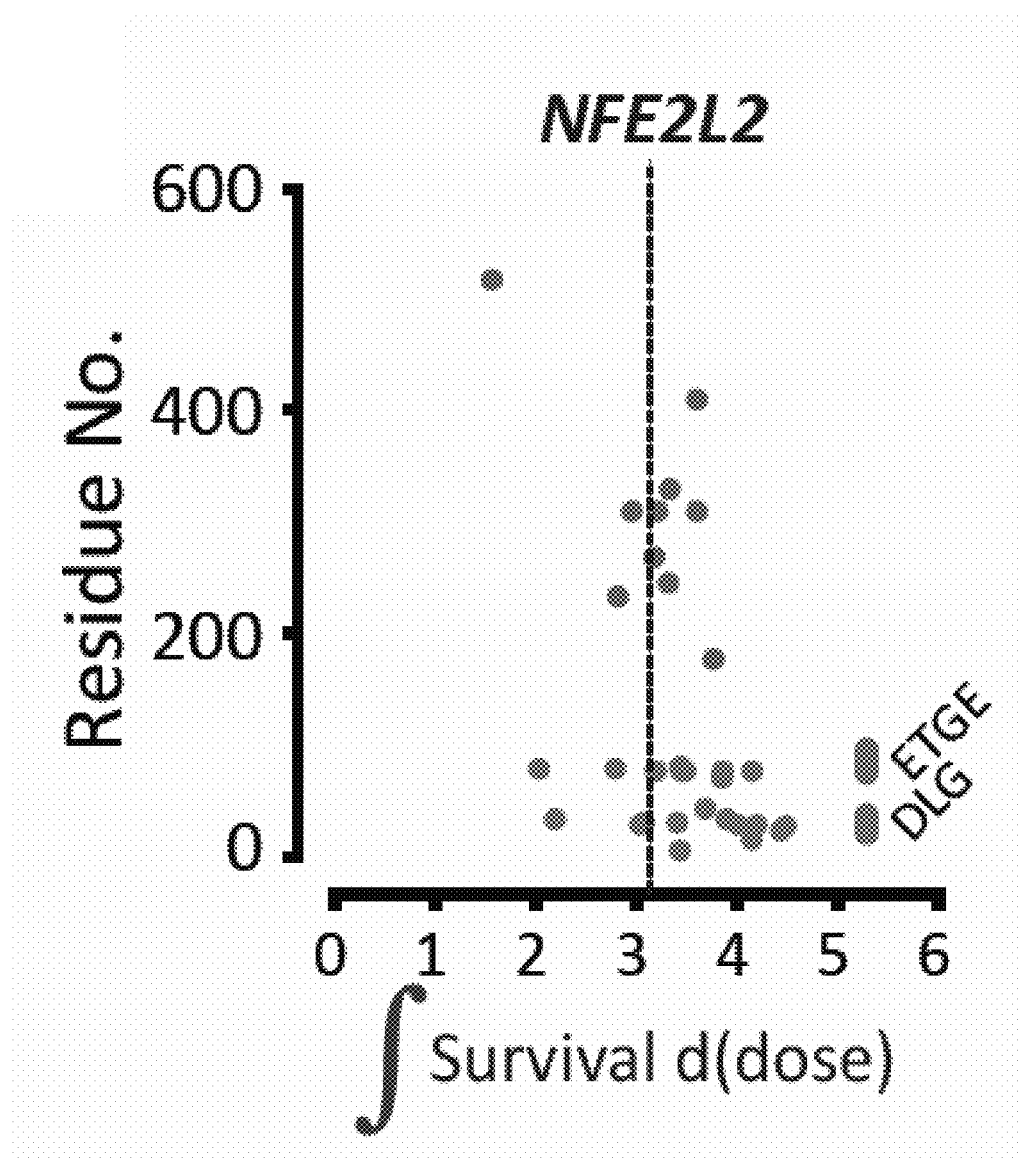

To assess the impact of mutation position on the IC, the relative importance of residue position on survival was assessed in the binding partner of Keap1, Nrf2 (FIG. 3i). In human cancer, somatic mutations in NFE2L2 frequently occur within the two KEAP1 binding sites ($D_{29}LG$ and $E_{79}TGE$)[33]. The IC value for NFE2L2 mutation across all lineages (IC=−0.0697; P=0.329, calculated using the empirical permutation test) was significantly higher when mutations restricted to the two KEAP1 binding sites were considered (IC=0.245; P=0.033, calculated using the empirical permutation test).

Taken together, these results describe gene mutation determinants of radiation-induced cellular damage response and reveal distinct functional consequences for categories of mutations within individual genes.

Figure 10A:
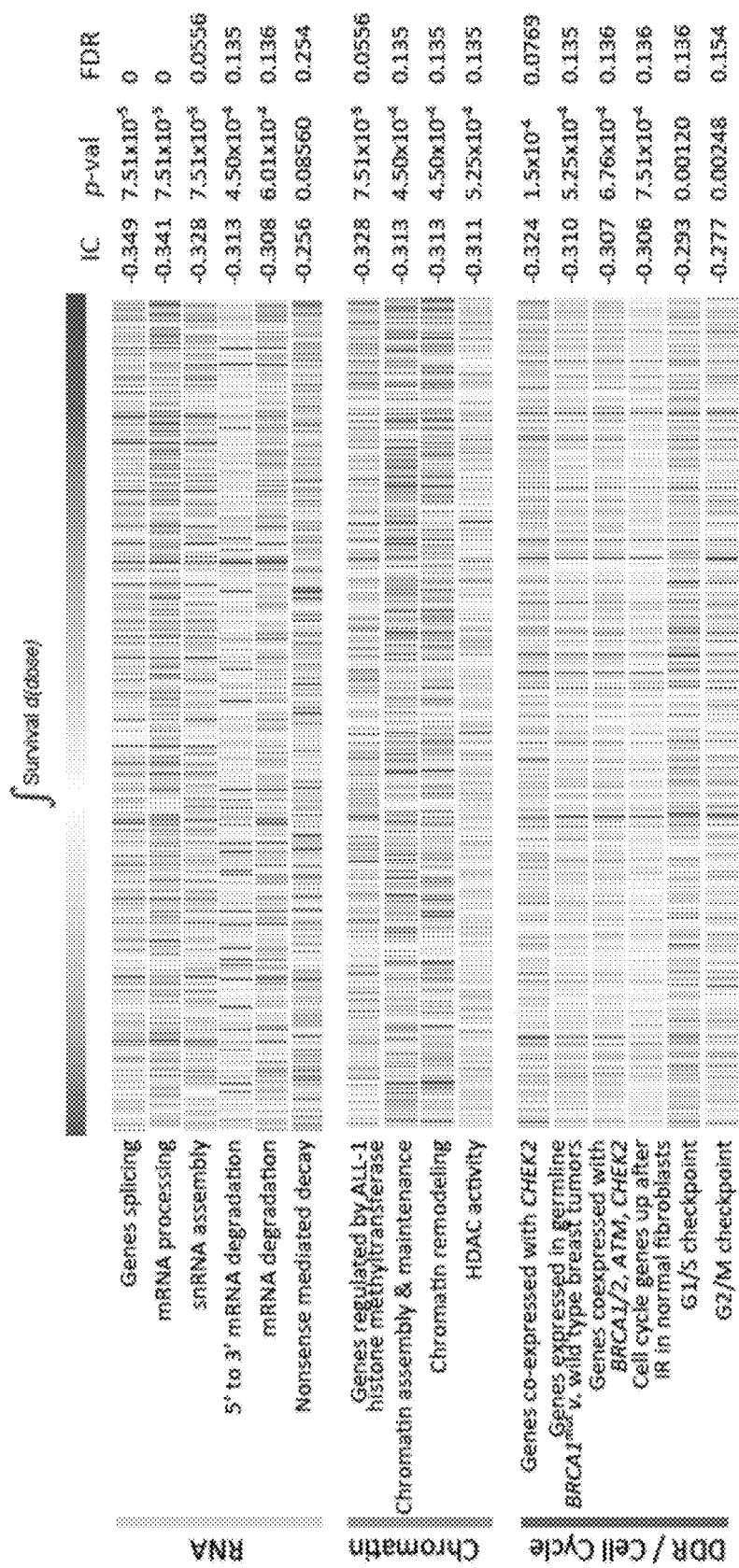
FIGS. 10A-10B. ssGSEA identifies gene sets that correlate with radiation sensitivity (a) and resistance (b). Heat map of ssGSEA scores. Top gene sets, organized by biological processes, are shown.
Figure 10B:
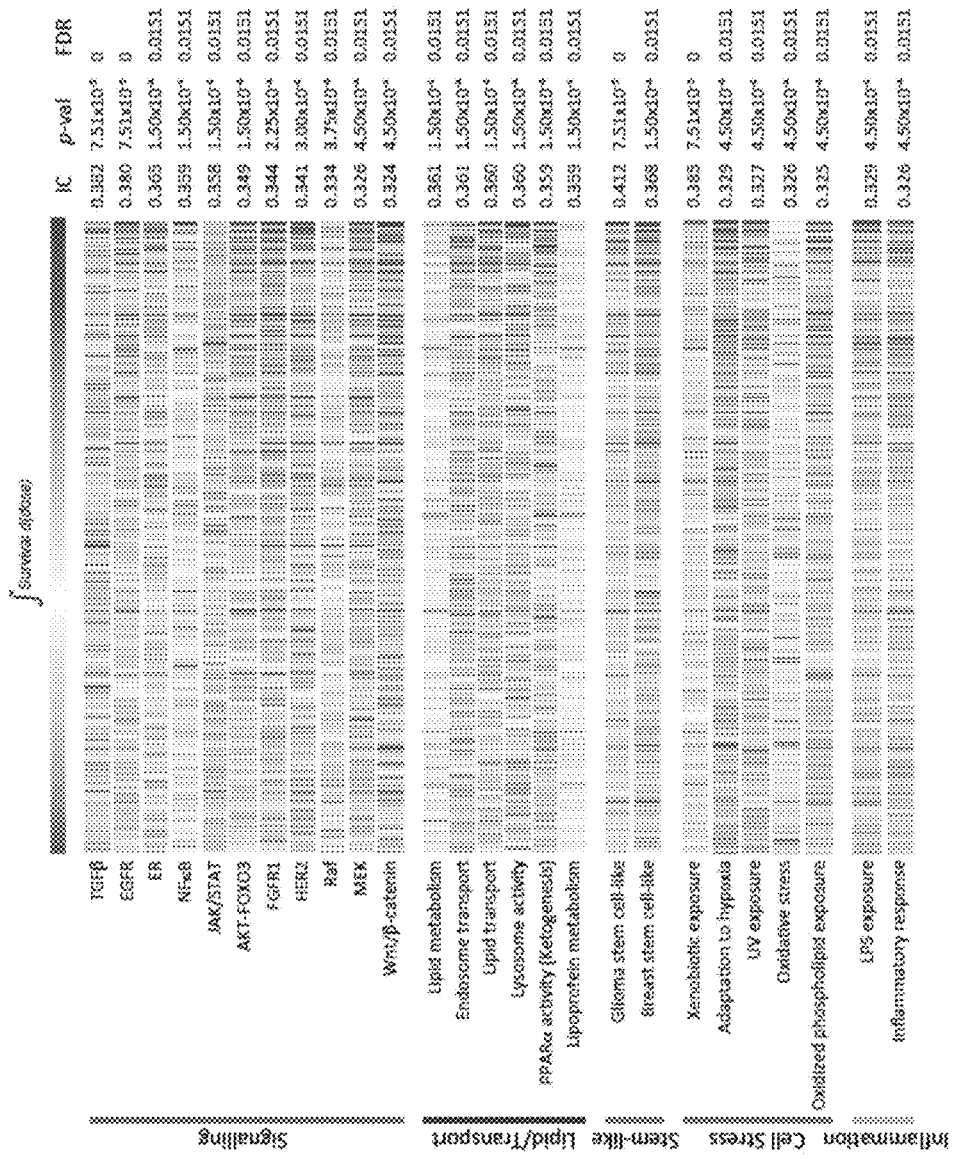

Gene Expression Profiles Regulate Survival after Irradiation ssGSEA (single-sample Gene Set Enrichment Analysis) projections[28, 34] was used as a gene set identification tool to find genetic pathways that are differentially correlated with radiation response. The profiles of each gene set/pathway were compared with the radiation response scores (integral survival) across cancer types. The ssGSEA scores are displayed in a heatmap with the top gene sets that correlate and anti-correlate with radiation survival organized by cellular pathways (FIG. 10). The top gene sets that correlated with radiation sensitivity revealed pathways including DNA damage response, cell cycle, chromatin organization, and RNA metabolism. The top gene set that correlated with radiation resistance revealed pathways including cellular signaling, lipid metabolism and transport, stem-cell state, cellular stress, and inflammation. The multitude of pathways associated with radiation response indicates that cellular processes well beyond DNA repair regulate cellular survival after radiation. A closer look at active signaling pathways that correlate with radiation resistance reveals several targetable cellular receptors including TGFβ, EGFR, Estrogen Receptor (ER), NFκB, JAK/STAT, AKT, FGFR, HER2, RAF, MEK, and Wntβ/-catenin. Some of these receptors have previously been shown to confer resistance to radiation in select cell lines[35]. These results indicate the broad role these signaling pathways serve in regulating radiation survival across several tumor lineages and implicate new targets for radiosensitization.

Figure 4A:
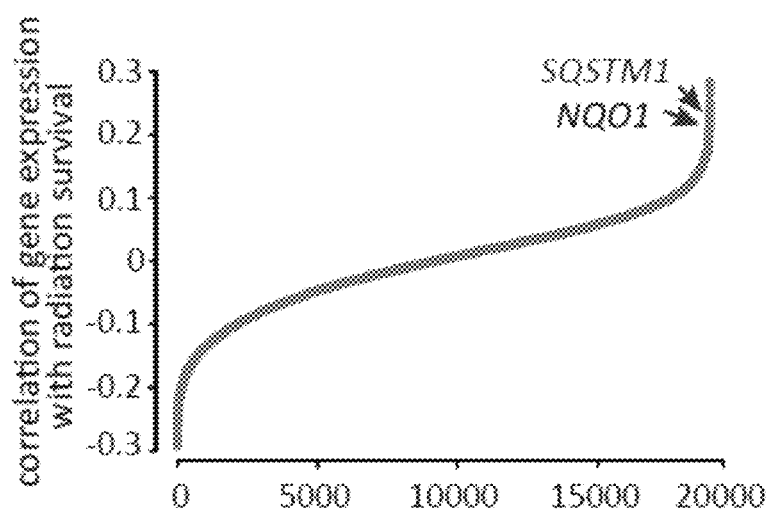
FIGS. 4A-4G. Gene expression changes regulating oxidative stress response are associated with radiation resistance in several cancer lineages. (a) Correlation of NQO1 and SQSTM1 expression with radiation resistance. Spearman correlation coefficient was calculated between gene expression and integral survival values. Correlation was then plotted relative to correlation rank. (b) Relationship between NQO1 and SQSTM1 mRNA expression in CCLE. (c) ssGSEA association between NFE2L2 signature score and integral survival. (d) NFE2L2 is frequently activated in hepatocellular (HCC) and biliary tumors. A column scatter plot of NFE2L2 signature score for 967 cell lines in the CCLE organized by disease site and histology where appropriate. Solid bars represent the mean in each category. Dashed line represents the median across all CCLE lines. (e) NFE2L2 activity scores and (f) SQSTM1 mRNA levels from HCC and biliary cancer cell lines were plotted as a function of radiation integral survival. (g) Kaplan-Meier survival analysis curve calculated from 122 hepatocellular cancer patients from TCGA; cut-off=z>1.5. z=+0.8 or greater demonstrated a statistically significant difference in overall survival by log-rank test.

To assess the importance of the expression of individual genes on radiation survival, correlation coefficients were calculated between 18,988 genes and integral survival values (FIG. 4a). NQO1 and SQSTM1, both transcriptionally activated by Nrf2[36], were the ninth and 11th genes identified as strongly associated with resistance, corroborating a role for oxidative stress response in radiation resistance already implicated by the gene mutation data. NQO1 encodes the NAD(P)H-quinone oxidoreductase, an enzyme that detoxifies cells from reactive oxygen species-induced quinone-containing compounds[37]. The ubiquitin binding protein, Sqstm1 (or p62) plays a role in oxidative stress, cellular signaling, and autophagy[38]. Sqstm1 has been previously shown to interact with Keap1 and accumulation of Sqstm1 can lead to an increase in Nrf2 activity[39].

Figure 4B:
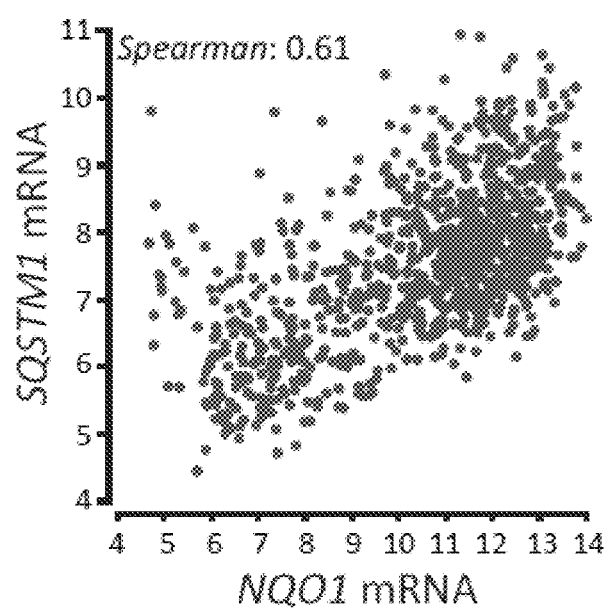
Figures 4C, 4D:
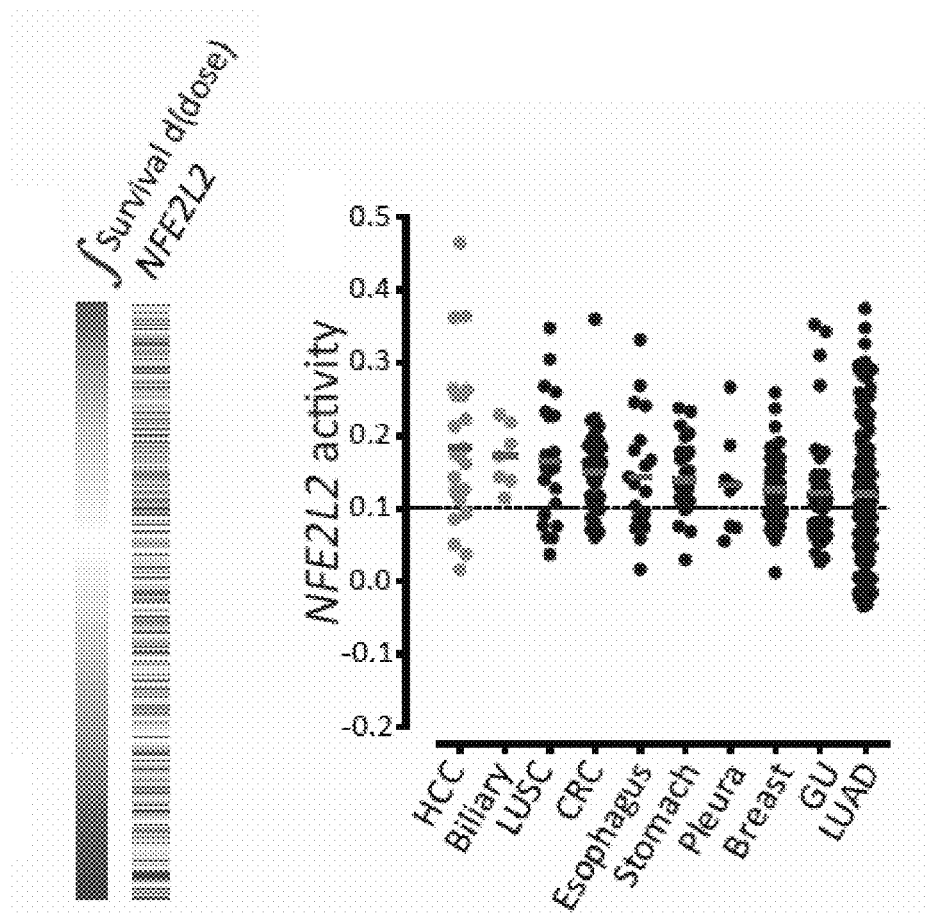
Figures 4E, 4F:
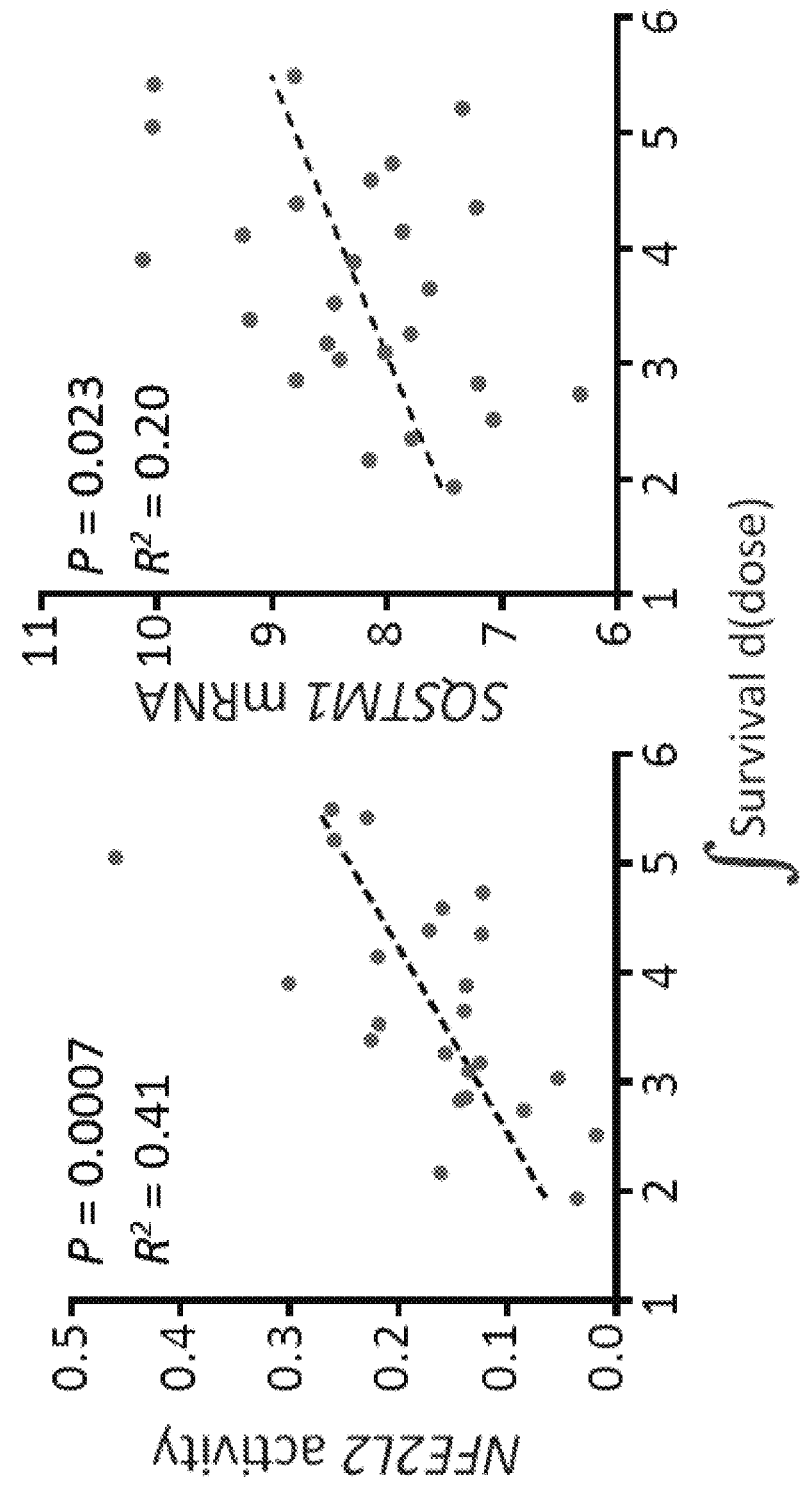
Figure 4G:
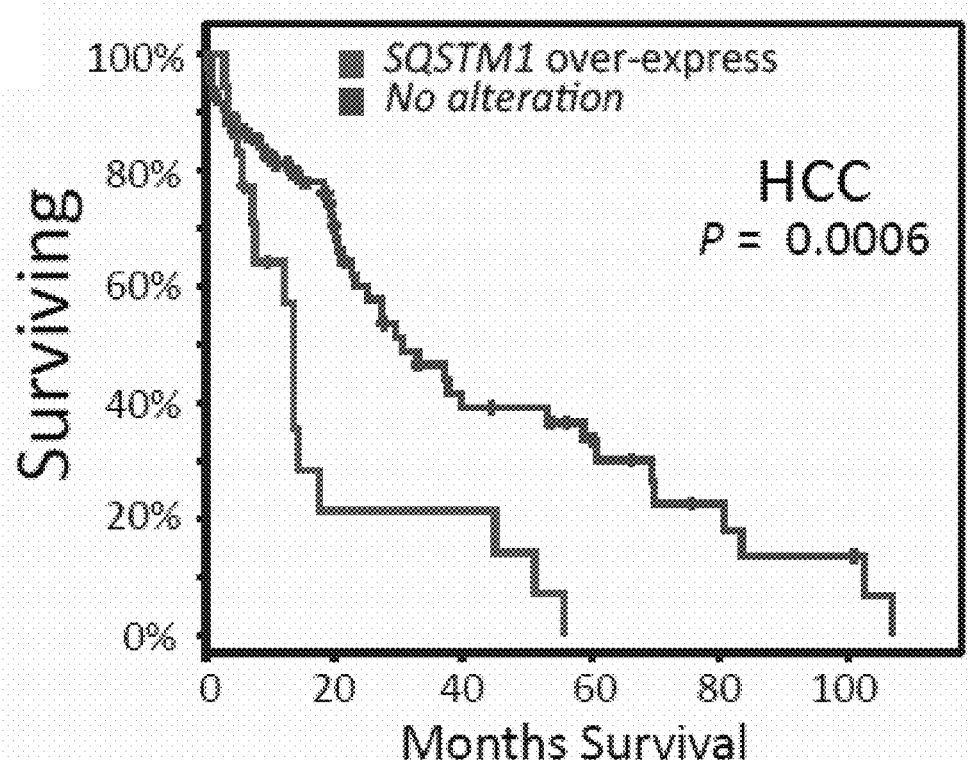
Figure 11:
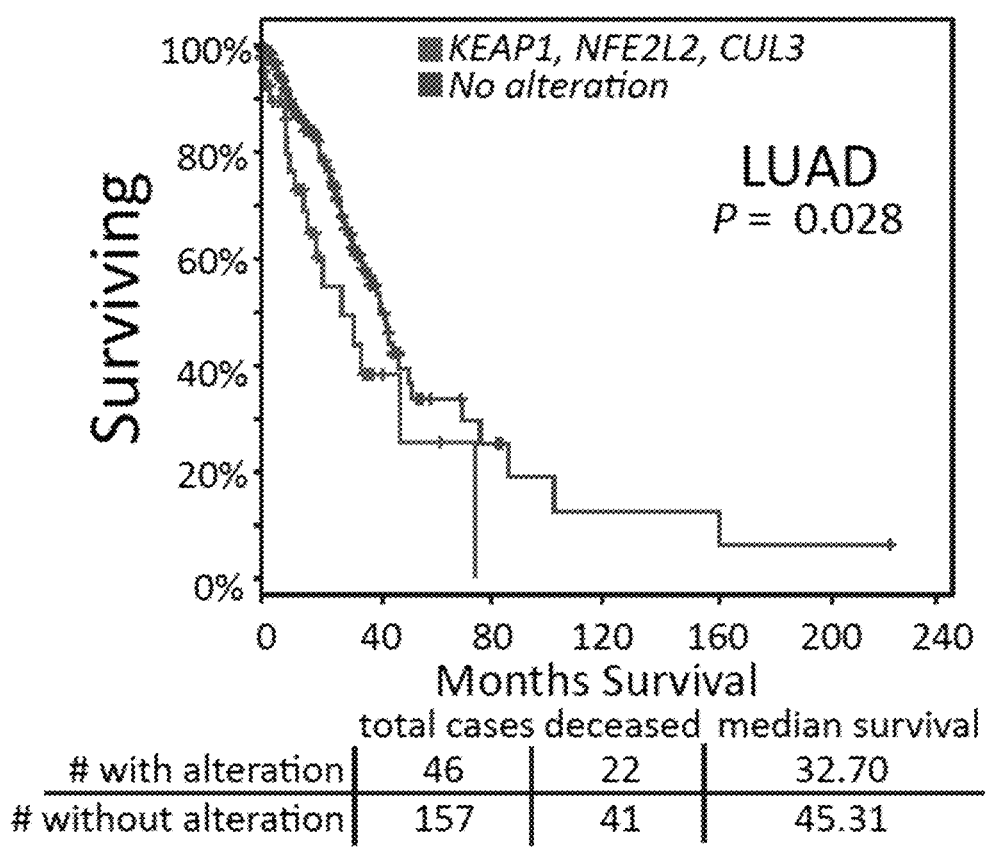
FIG. 11 Kaplan-Meier survival analysis curve calculated from lung adenocarcinoma patients from TCGA separated by NFE2L2 (mutation or CNA), KEAP1 (mutation or CNA), and CUL3 homozygous deletion versus none of these alterations. There was a statistically significant difference in overall survival by log-rank test (P=0.028).

Consistent with these results, NQO1 and SQSTM1 gene expressions are strongly correlated across 979 Cancer Cell Line Encyclopedia (CCLE) cell lines (FIG. 4b) and NFE2L2 transcriptional activity is associated with radiation survival across all lineages (FIG. 4c). NFE2L2 transcriptional activity plotted by lineage revealed the highest overall activity in hepatocellular carcinoma (HCC) and biliary cancer (FIG. 4d). It was shown that Nrf2 is mainly activated by mutations in NFE2L2 and/or KEAP1 and/or deletions in CUL3 in lung squamous cancers (LUSC)[28]. Similar gene alterations have not been identified in HCC or biliary cancer (TCGA network). Instead, recent reports suggest an important role for SQSTM1 in Nrf2 activation in HCC[39]. To test the association between Nrf2 and Sqstm1 activity and radiation survival in HCC, integral survival values were plotted with NFE2L2 activity (FIG. 4e) and SQSTM1 expression (FIG. 4f). It was found that HCC had the strongest association between radiation survival and Nrf2 activity in any lineage profiled ($R^2$=0.41 in HCC v. $R^2$=0.22 in LUSC). SQSTM1 expression was also correlated with radiation survival, albeit at a lower level than that obtained with the Nrf2 score. This was attributed to noise associated with single gene expression measurements, compared to a composite Nrf2 score that includes 565 genes. HCC is commonly managed by genotoxic therapies (chemo- and/or radio-embolization, external beam radiotherapy) and/or surgery, suggesting that patients who resist genotoxic stress may have poorer clinical outcomes. HCC patients with elevated SQSTM1 expression have a significantly lower overall survival, indicating a poor overall prognosis for patients with active Nrf2 in HCC (FIG. 4g) (TCGA network). This is analogous to the poor prognosis of NSCLC patients with active Nrf2 [[40] and FIG. 11].

Radiogenomic Profiling of Breast Cancer

For many women with breast cancer, breast-conserving surgery or mastectomy can result in the removal of detectable macroscopic disease. However, tumor foci might remain in local and regional tissue such as the intact breast or chest wall and/or regional lymph nodes. Tumor recurrence can cause considerable morbidity, dissemination of disease, and an increased probability of breast-cancer mortality[41, 42]. Radiotherapy significantly decreases the risk of local and regional recurrence and breast cancer mortality[43, 44]. Despite the demonstrated efficacy of breast radiotherapy, there remains an important need for identifying patients who are more likely to fail therapy and improving radiation treatments in those patients.

Figure 5A:
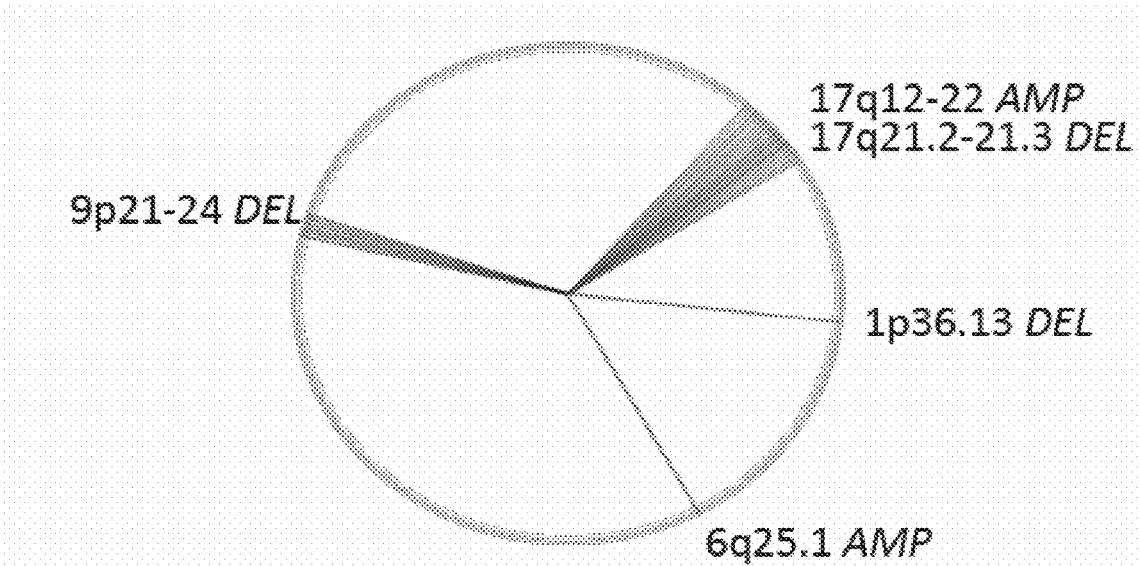
FIGS. 5A-5F. Genes associated with survival after radiation-induced damage in breast carcinoma. (a) The top 50 copy-number probes associated with radiation resistance in breast adenocarcinoma are shown. Radii (single probe) or sectors (multiple probes) correspond to chromosome positions. (b) ERBB2 amplification is associated with survival after radiation-induced damage. Three-dimensional scatter plot of integral survival, ERBB2 copy-number, and ERBB2 mRNA expression. (c) ssGSEA identifies gene sets that correlate with resistance to radiation. Heatmap of ssGSEA scores (left=positive, right=negative). A subset of the top 27 gene sets is shown. Genes sets depicted in red font are associated with androgen signaling. (d) Scatter plot and linear regression of AR mRNA levels and radiation integral survival in breast cancer. (e) AR is frequently expressed in multiple cancer lineages. A box and whiskers plot of AR expression for 967 cell lines in the CCLE organized by lineage. Whiskers represent minimum and maximum values. (f) (Left) Relative AR, ER, and HER2 protein levels in whole cell extracts from breast cancer cell lines and LNCaP, a prostate cancer cell line. (Right) Annotation of expression based on Western analysis include: − (no observable expression), + (expression), or −/+ (faint expression was observed with longer exposure to film).
Figure 5B:
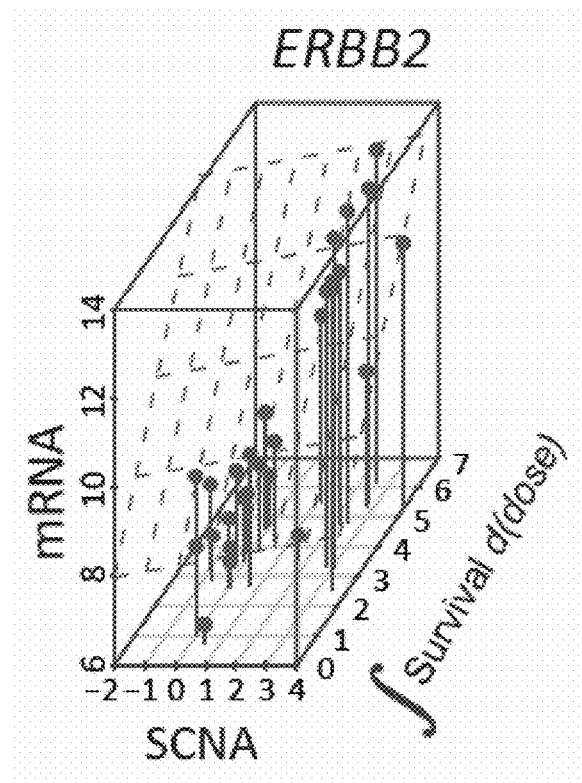

To identify genetic determinants of radiation survival in breast carcinomas, an unbiased query of gene mutations or copy number changes was begun that correlated with radiation survival in 28 breast cancer cell lines. The top 50 segments correlating with resistance were organized by chromosomal position and the results were depicted using a wheel-plot (FIG. 5a). Amplification of 17q12-22, which contains ERBB2, was associated with radiation resistance. Cell lines containing 17q12-22 amplification had elevated ERBB2 copy number and mRNA, and were generally derived from tumors clinically annotated as having ERBB2 amplifications. ERBB2 copy number (Pearson r=0.43) and gene expression (Pearson r=0.45) were correlated with radiation survival (FIG. 5b). These results suggest that ERBB2 is the likely mediator of radiation resistance in the 17q12-22 amplicon. Consistent with these results, overexpression of ERBB2 has previously been shown to confer therapeutic resistance in breast cancer cells and Trastuzumab, a monoclonal antibody that interferes with ErbB2, sensitizes ErbB2 expressing cells to radiation[45].

AR Regulates Survival after Irradiation in Breast Cancer

Figure 5C:
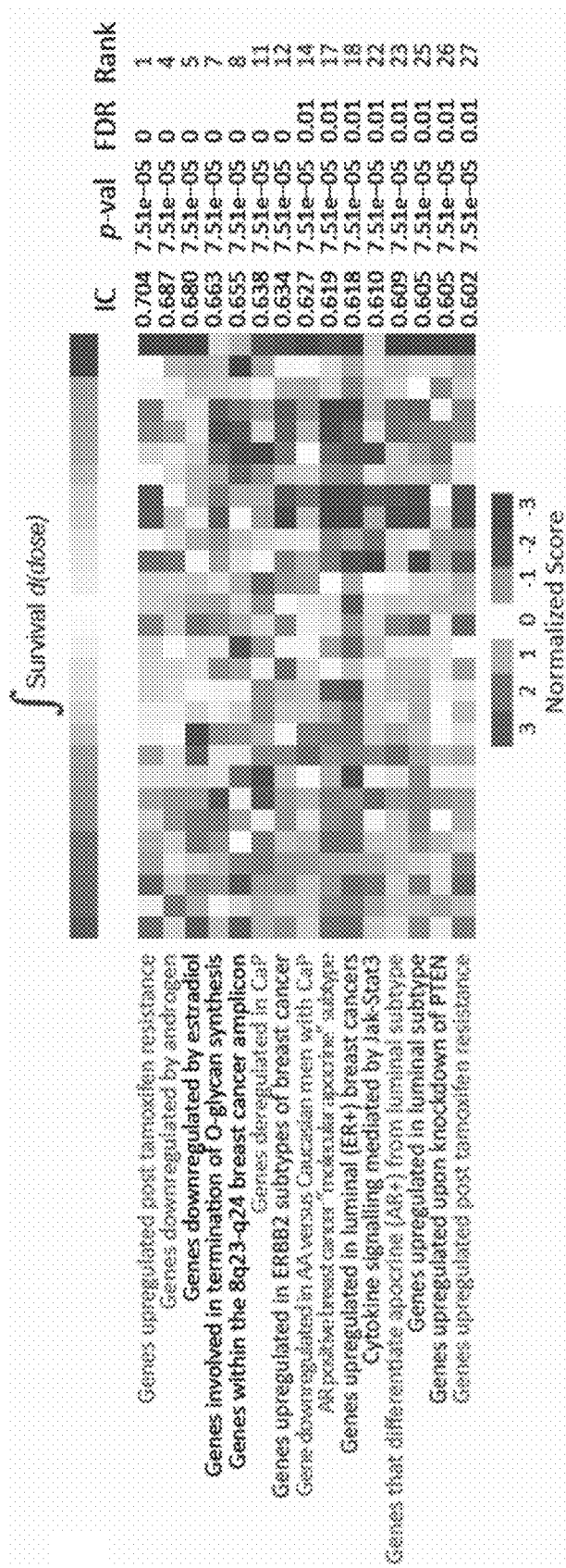

To find additional genetic pathways that are differentially correlated with radiation response, ssGSEA projections were applied (FIG. 5c). Multiple pathways were correlated with radiation resistance (ER, ERBB2, JAK/STAT3, and PI3K). However, one of the most correlated and intriguing gene sets identified was associated with androgen signaling. Androgen receptor (AR) expression is most frequently observed in prostate cancer, where it has been shown to promote resistance to radiation[46]. Several clinical studies have demonstrated a benefit in overall survival with the combination of androgen-deprivation therapy and radiation compared to radiation alone in patients with intermediate- and high-risk prostate cancer[47, 48, 49]. Although its role in breast oncogenesis remains poorly defined, AR is detected in a majority of breast carcinomas at levels greater than normal breast[50]. A subset of AR-positive, triple-negative breast carcinomas, which lack ER and progesterone receptor (PR) expression and ErbB2 overexpression, appear to be dependent on AR signaling for growth[51, 52]. A phase II study that explored bicalutamide in AR-positive, ER/PR-negative metastatic breast cancer showed a modest clinical benefit[53]. A single-arm phase II is currently assessing the more potent AR antagonist, enzalutamide (ENZ), in women with advanced, AR-positive, ER/PR-negative breast cancer. Therefore, the clinical effectiveness of anti-androgens as single agent therapy in the management of breast cancer patients remains unknown. Based on the initial results and these observations, it was sought to examine the role of AR and test the rationale for combining androgen blockade and radiation in breast cancer, as is the standard of care in locally advanced prostate cancer[47, 48].

Figure 5D:
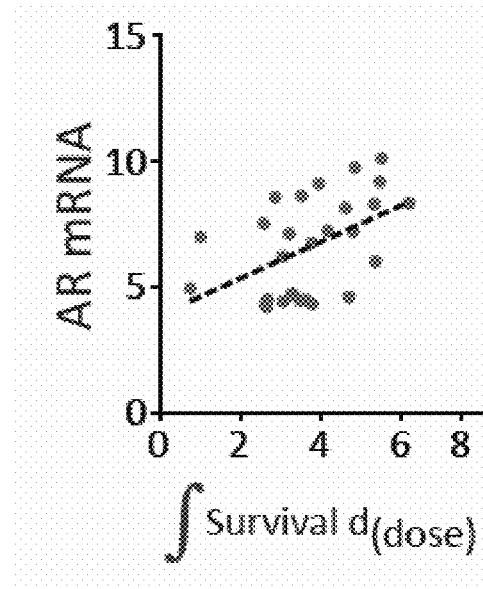
Figure 5E:
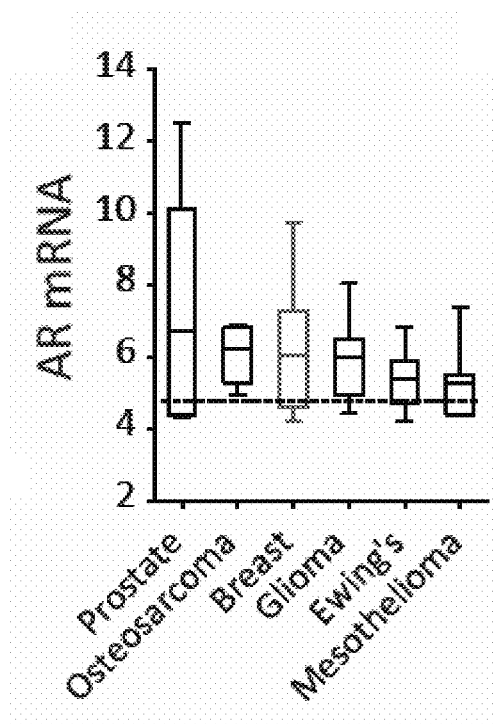
Figure 12:
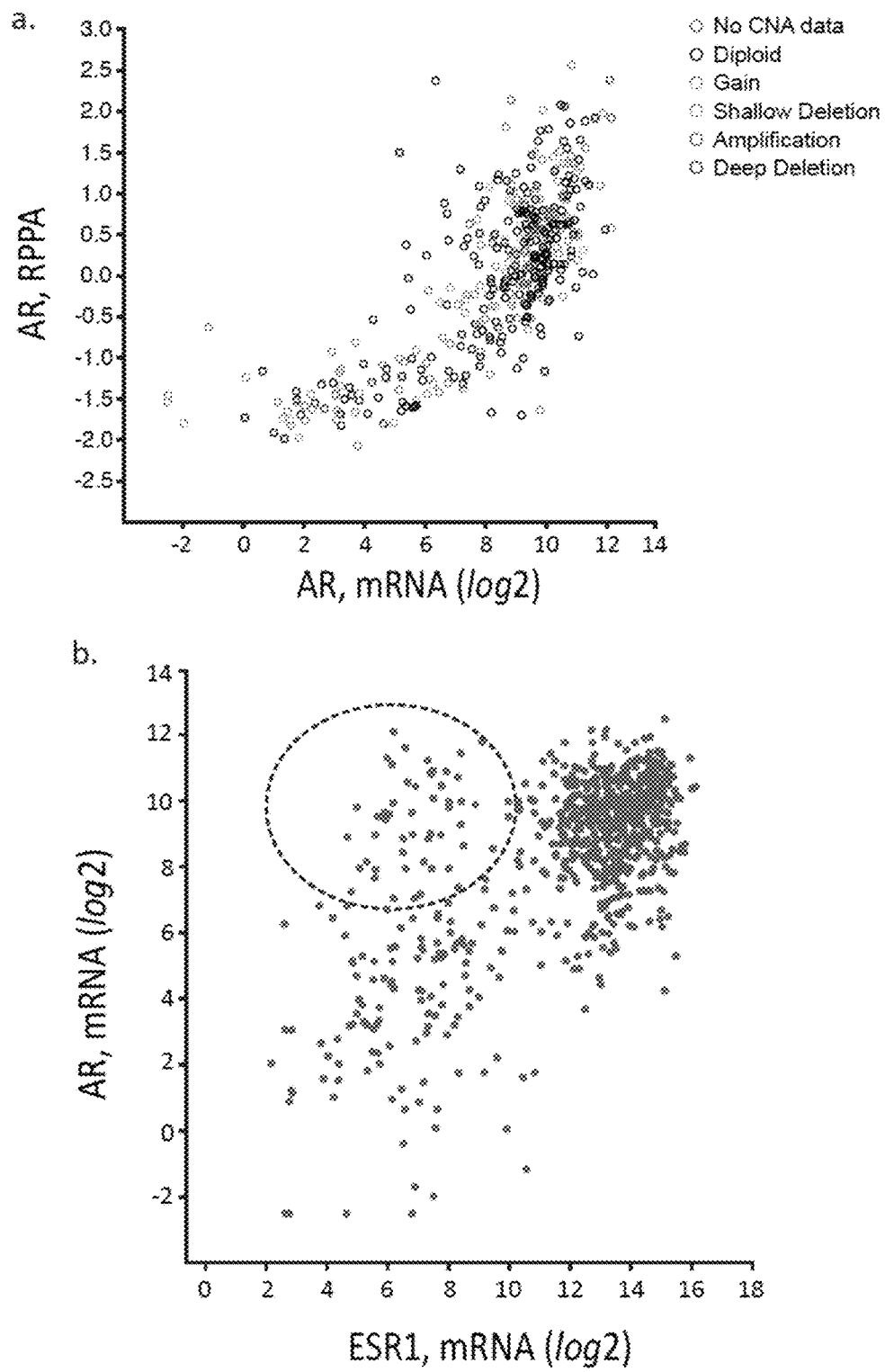
FIG. 12. Correlation of AR and ESR1 expression. (Panel a) AR protein levels correlate with mRNA levels (Pearson r=0.615). AR overexpression is mostly observed in diploid tumor samples, suggesting that increased AR expression is mainly regulated by increased gene transcription rather than gene amplification. AR protein was measured by reverse phase protein array (RPPA) and mRNA measured by RNA-Seq from 1098 breast cancer patient samples profiled by TCGA and analyzed by cbioportal. (Panel b) Scatter plot and regression of AR and ESR1 mRNA expression are shown (Spearman r=0.51). Breast tumors that express AR and not ESR1 were determined using a cut-off of the median for AR and ESR1 expression and delimited by a dashed circle. RNA-Seq expression values were calculated by expectation maximization (RSEM) and scaled by log 2 transformation.
Figure 13:
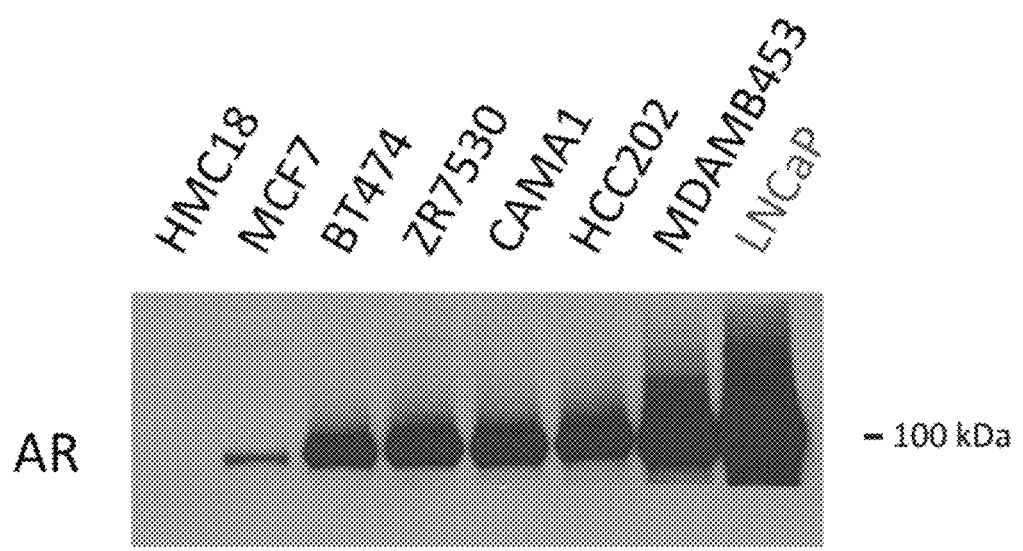
FIG. 13. Relative AR protein levels in whole cell extracts from breast cancer cell lines and LNCaP, a prostate cancer cell line. Increased time of film exposure reveals that MCF7 cells express low levels of AR (compare to FIG. 11). HMC18 cells do not express AR protein.

It was shown that AR mRNA levels correlated with radiation survival (Pearson r=0.48) (FIG. 5d). Data was analyzed from the CCLE to determine the relative mRNA levels of AR across lineages. Prostate cancers had the highest mean value among 28 tumor types followed by osteosarcoma and breast cancer (FIG. 5e). An association between AR mRNA and protein levels (Pearson r=0.615) was determined, and AR and ESR1 (or ERα) mRNA (Pearson r=0.34) in TCGA patient samples (FIG. 12). A subset of TCGA samples expressed AR and not ESR1. Consistent with this data, it was shown that some of the breast carcinoma cell lines that were profiled expressed AR with varying levels of ER (and ErbB2) (FIG. 5f and FIG. 13).

Figure 5F:
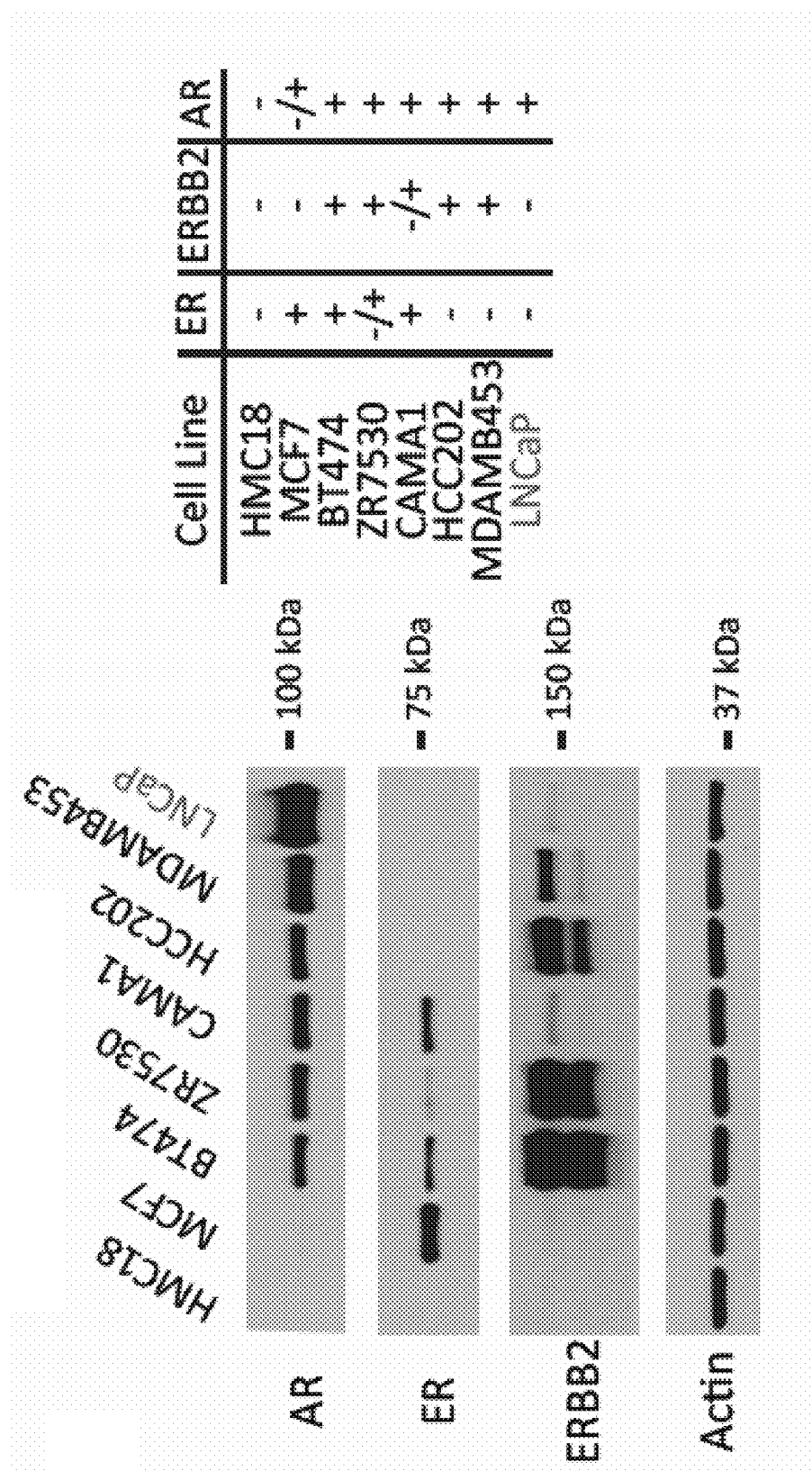
Figure 14:
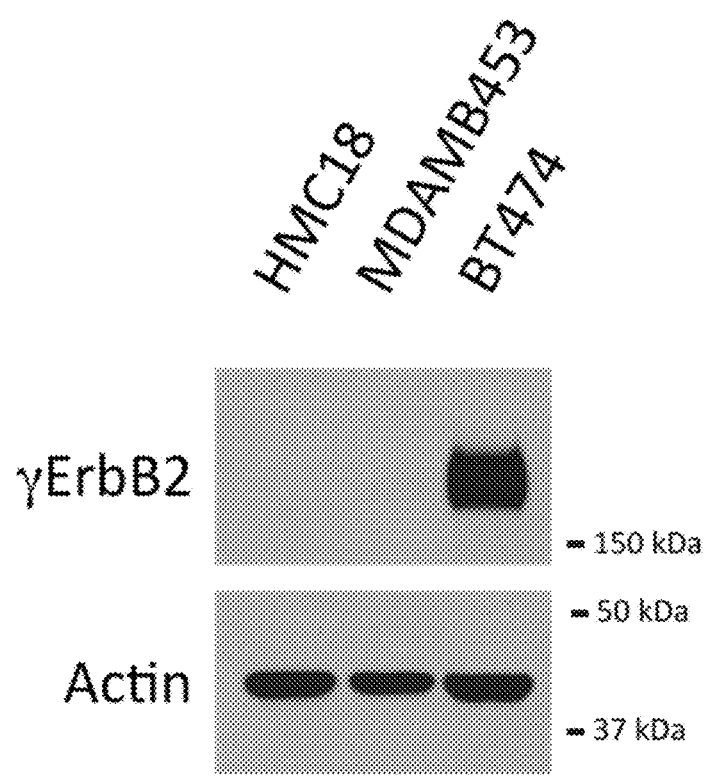
FIG. 14. ErbB2 is overexpressed but not activated in MDAMB453 cells. γErbB2 and actin levels were measured in whole cell extracts from HMC18, MDAMB453, and BT474 cells.

MDAMB453 cells expressed AR but not ER, and although ErbB2 was overexpressed in these cells, the level of expression was significantly lower than that observed in other AR positive cell lines (BT474, ZR7530, or HCC202) (FIG. 5f). To examine the activity of ErbB2 in this cell line, levels of γErbB2 levels at tyrosine 1248[54] were measured. γErbB2 was not elevated in MDAMB453 cells, indicating that ErbB2 is not activated in this cell line (FIG. 14). These results indicate that ERBB2 overexpression is not sufficient to activate ErbB2 in MDAMB453 cells. Taken together, MDAMB453 cells are AR-positive, ER-negative and ErbB2 inactive, consistent with its gene expression-based classification into the luminal AR expressing subtype of triple-negative breast cancer[55].

Figure 6A:
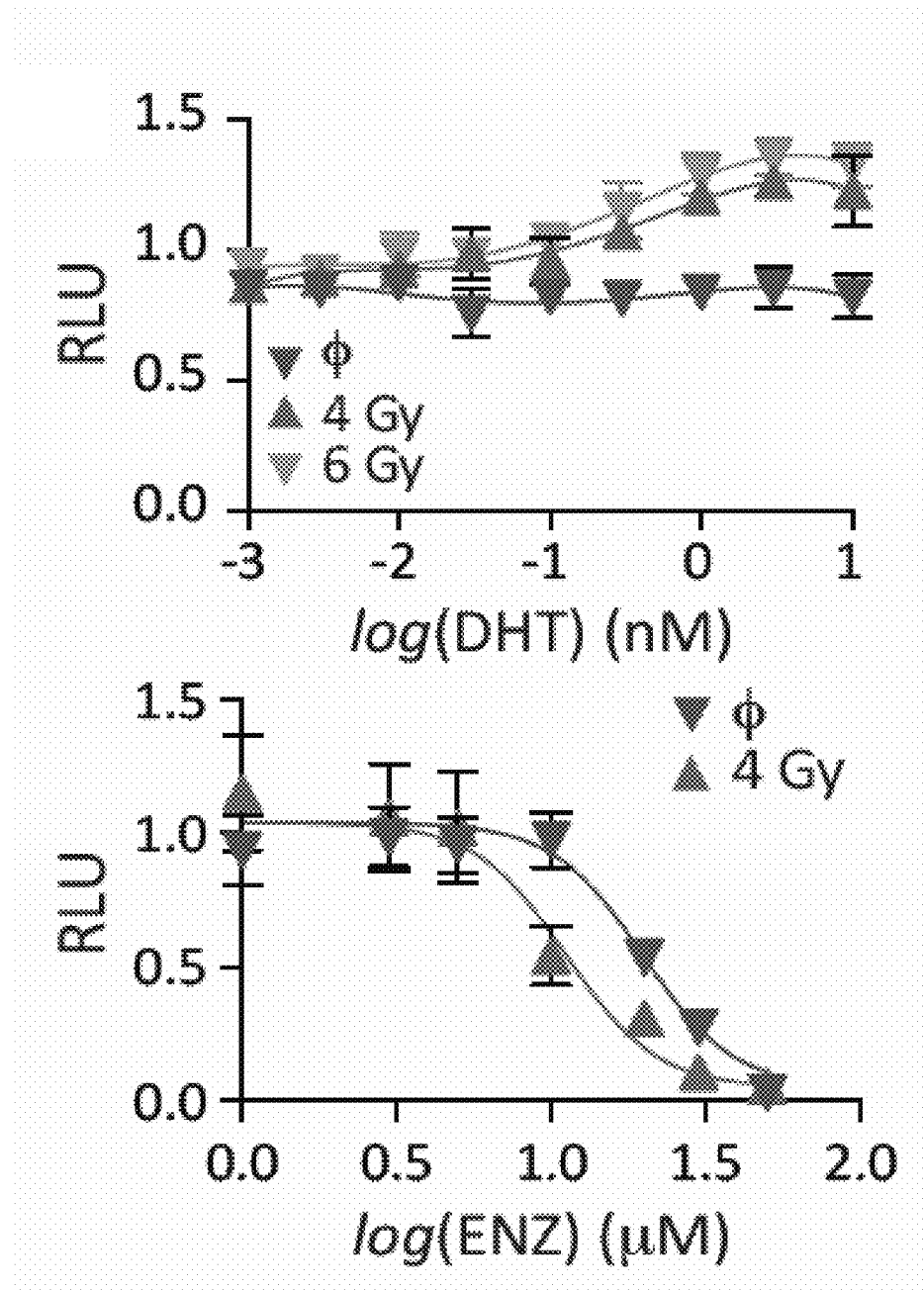
FIGS. 6A-6I. AR activity regulates the response to DNA damage in breast carcinoma. (a) (Top) Cells were cultured in steroid-deprived media −/+ DHT for 24 hours and then treated with IR: mock (ϕ), 4 Gy, or 6 Gy. Cells were then supplemented with hormone-proficient media at 48 hours post-IR. Cell number was determined on day 14-21. (Bottom) Cells were cultured in hormone-proficient media for 24 hours without or with enzalutamide (ENZ) and then treated with IR; mock (ϕ) or 4 Gy. Error bars represent normalized s.e.m of at least three experiments. (b) MCF7, BT474, CAMA1, HCC202, and MDAMB453 cells were treated with ENZ, ENZ+IR, DHT, or DHT+IR as in (a). HMC18 cells were treated similarly but were profiled by clonogenic survival assays. Error bars represent normalized s.e.m of at least three experiments and the Student's t-test was used for statistical analysis. *, P<0.05. (c) Neutral Comet assay of MDAMB453 cell line, showing increased double-strand breaks when cells were irradiated in steroid-deprived conditions (left) or after 24 hours of treatment with 20 µM of ENZ (right). Error bars represent s.e.m of at least three experiments and the Student's t-test was used for statistical analysis. *, P<0.05. (d) Cells were cultured in hormone-proficient (FBS) media for 24 hours −/+ ENZ and then treated with IR: mock (φ 3 Gy (HMC18 and MDAMB453), or 2 Gy (C4-2). Cells were cultured in steroid-deprived media for 48 hours, treated −/+ DHT for 24 hours, and then treated with IR: mock (φ), 3 Gy (HMC18 and MDAMB453), or 2 Gy (C4-2). γH2AX, HDAC1, and actin levels were measured at the indicated time points. Relative intensity of γH2AX was calculated by ImageJ64. (e) MDAMB453 cells were cultured in steroid-replete, steroid-deficient, or steroid-deficient with 1 nM DHT for 24 hours, then treated with irradiation. Cells were harvested and expression of γDNAPKcs was analyzed. Androgen deprivation therapy (ADT). (f) Schematic of treatment arms. (g) MDAMB453 cells were orthotopically injected into the mammary gland of NSG mice and block randomized into one of four treatment arms as shown. Tumor volume was measured daily. Error bars represent normalized s.e.m of at least seven mice in each treatment arm. *, P<0.05 compared with all other treatment conditions based on ANOVA and Tukey Contrasts. **, P<0.05 for interaction based on two-way ANOVA. (h) Pictorial depiction of representative mice from each arm of cohort 2 at the end of treatment. This cohort received ENZ at 25 mg kg$^{-1}$. (i) Average weight for each arm in both cohorts was measured weekly. Data are expressed as the means±s.e. of at least seven mice in each treatment arm.
Figure 6B:
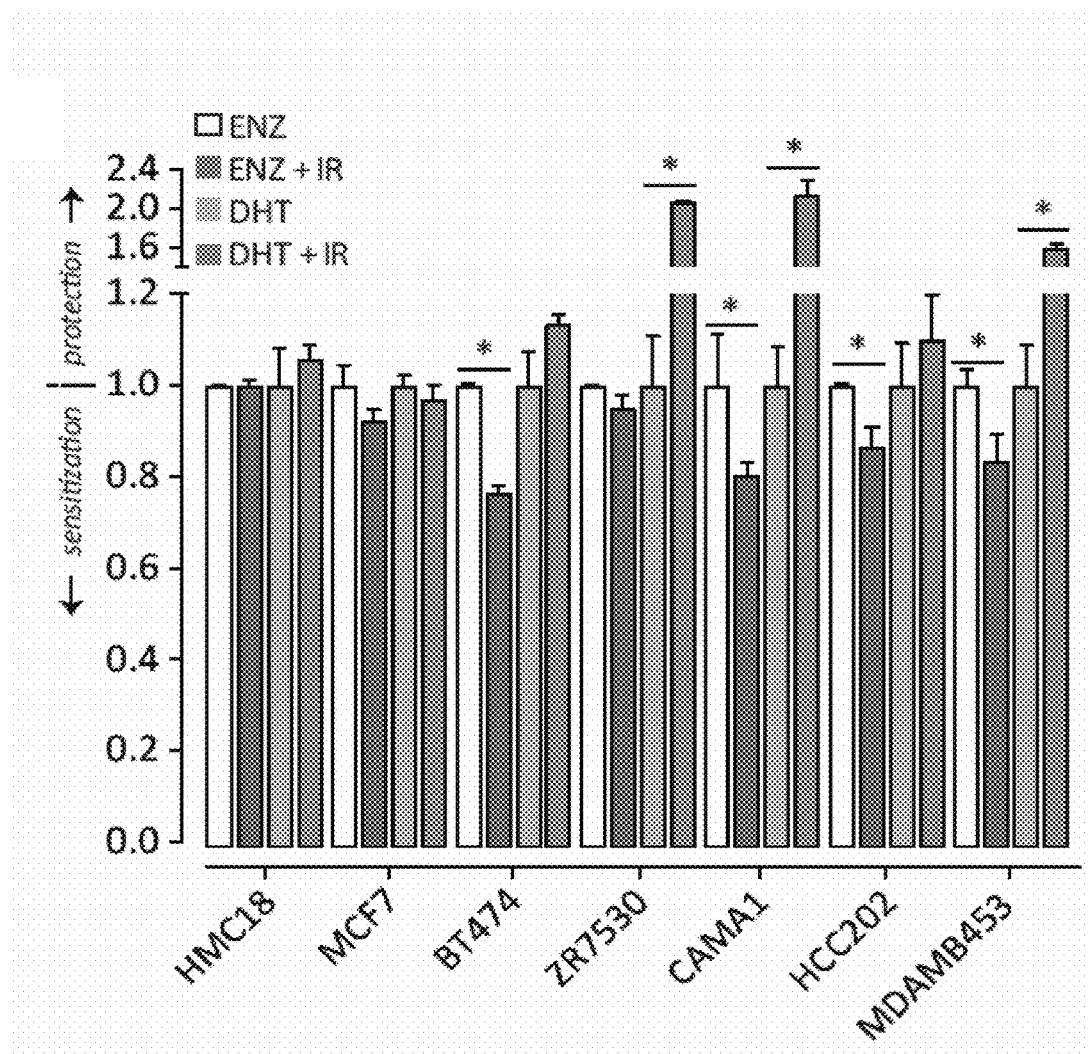
Figure 15A:
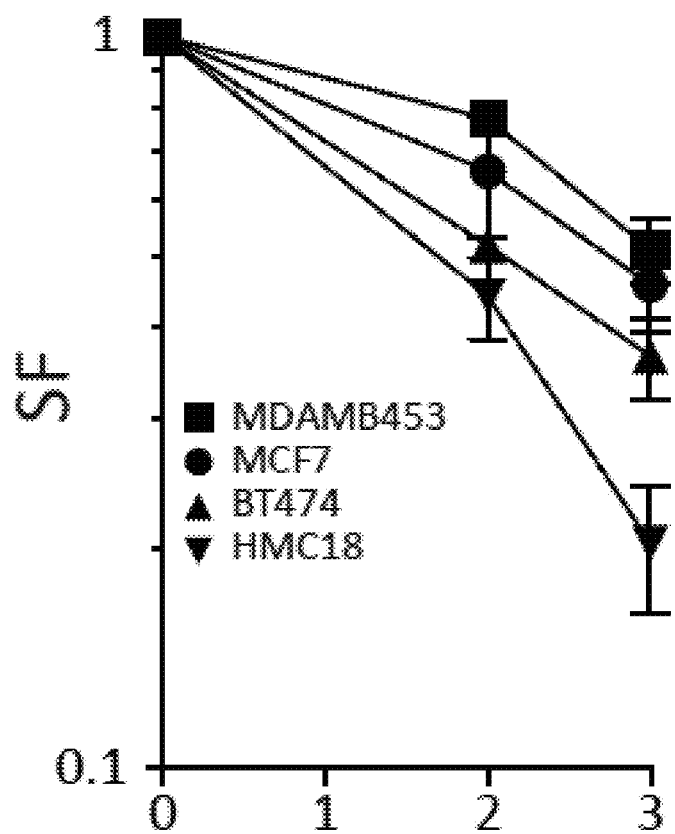
FIGS. 15A-15B: Clonogenic survival measurements in breast cancer cells. (a) Clonogenic survival measurements of breast cancer cells HMC18, MCF7, BT474, and MDAMB453. Colony number was determined on days 7-21. Data are expressed as the means±s.e.m of at least three experiments. (b) Clonogenic survival measurement of enzalutamide-mediated radiosensitization in cell lines HMC18, MCF7, BT474, and MDAMB453. Cells were cultured in hormone-proficient (FBS) media for 24 hours without or with enzalutamide (ENZ) and then treated with IR; mock (φ) or radiation. Colony number was determined on days 7-21. Data are expressed as the means±s.e.m of at least three experiments.
Figure 15B:
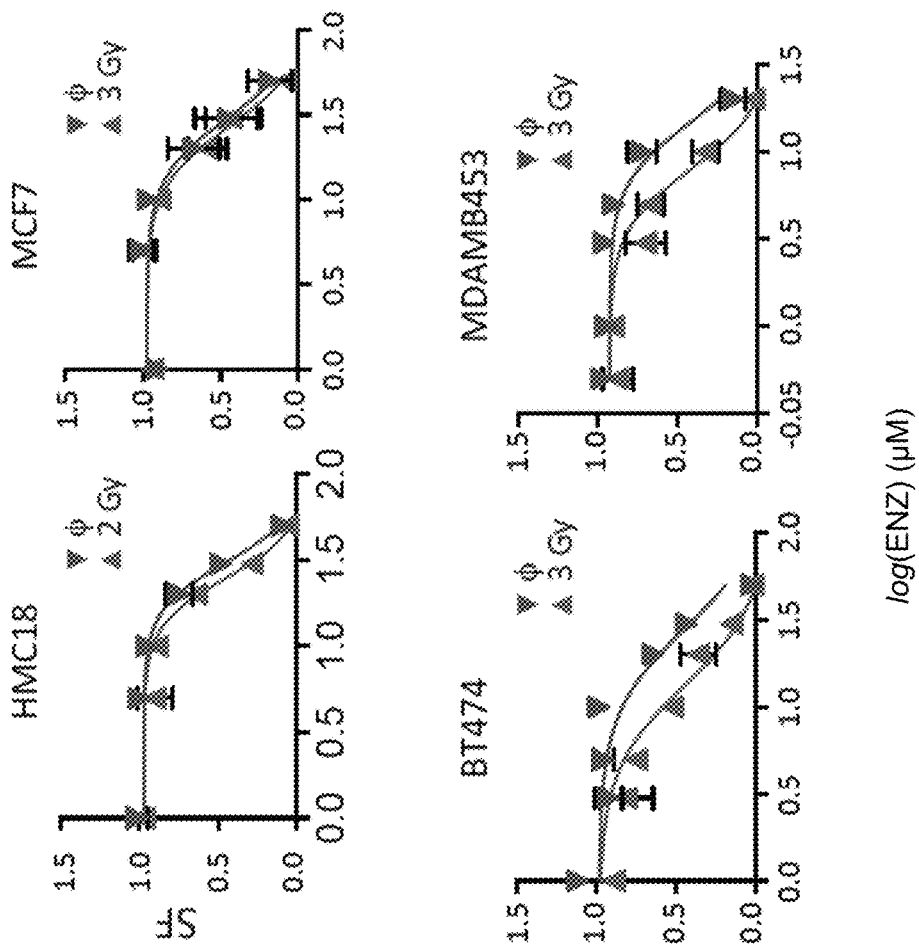

MDAMB453 cells were used to test the interaction between androgen signaling and survival after radiation. Dihydrotestosterone (DHT) re-supplementation of MDAMB453 cells cultured in steroid-deprived media before radiation showed dose dependent rescue of cell growth (FIG. 6a, top). Conversely, ENZ, which competes with DHT for binding to the receptor and prevents its nuclear translocation, decreased cell number compared to vehicle alone (FIG. 6a, bottom) Of note, this experimental system models single fraction radiation treatment. Patients typically receive 16-30 total fractions of treatment, which is predicted to compound the magnitude of the observed interaction between androgen signaling and radiation. The same growth survival assay was employed across several cell lines and showed protection and sensitization with DHT and ENZ, respectively, and only in cell lines that expressed AR and independent of ER and ErbB2 activity (FIG. 6b). For cells capable of forming colonies, these results were confirmed using a clonogenic survival assay (FIG. 15).

AR Protects Breast Cancer Cells from DNA Damage

Figure 6C:
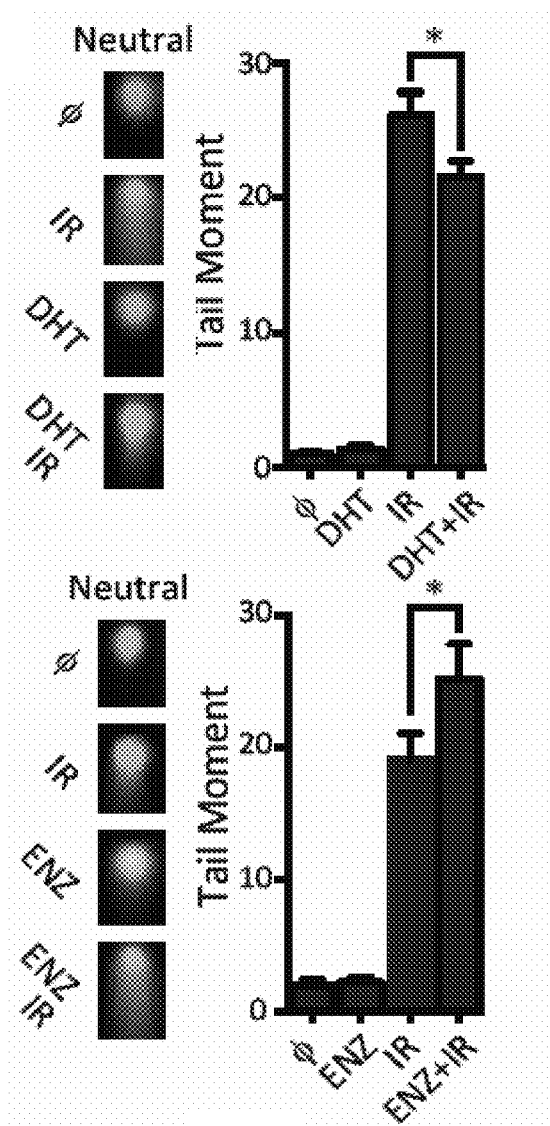
Figure 6D:
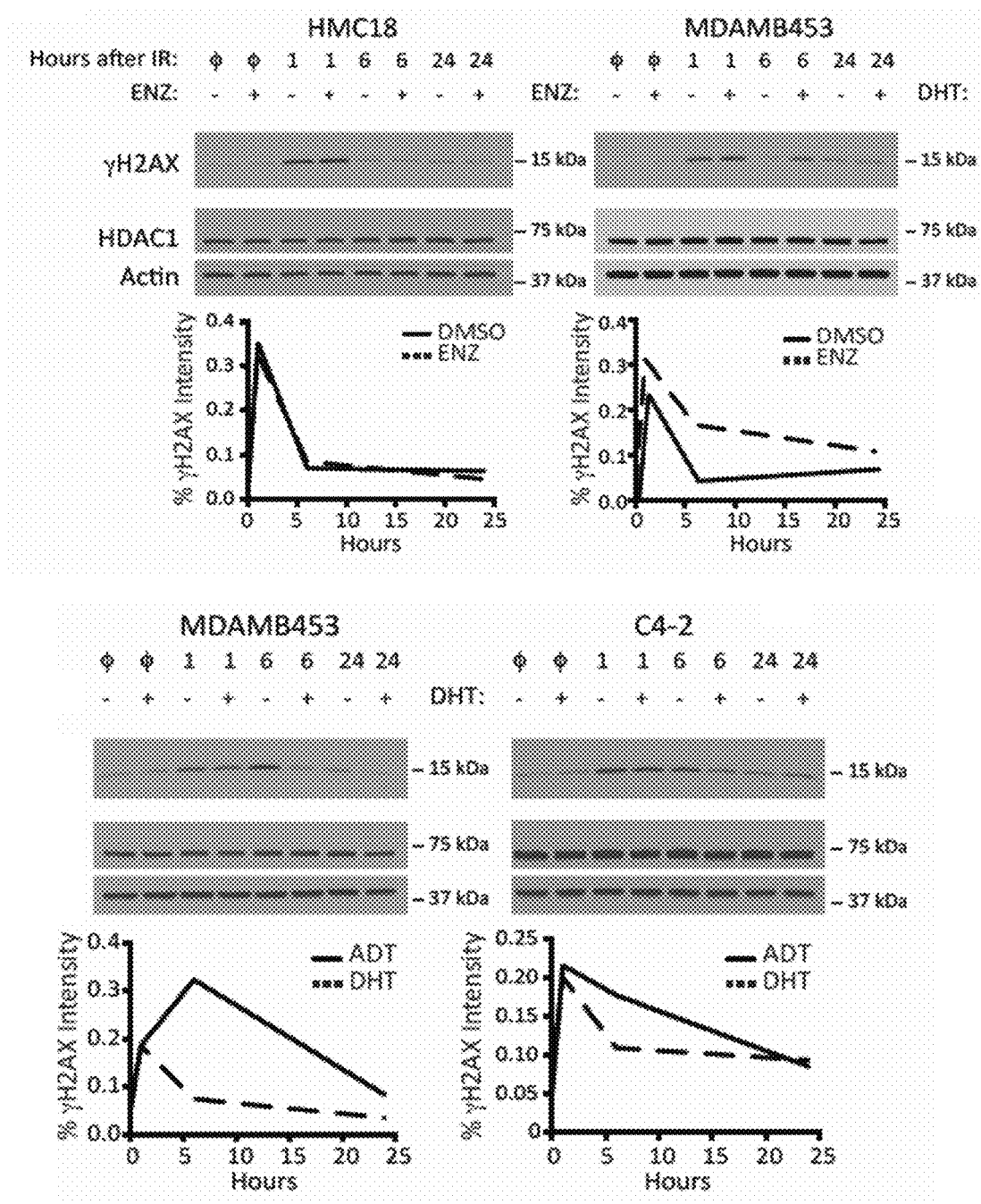
Figure 16:
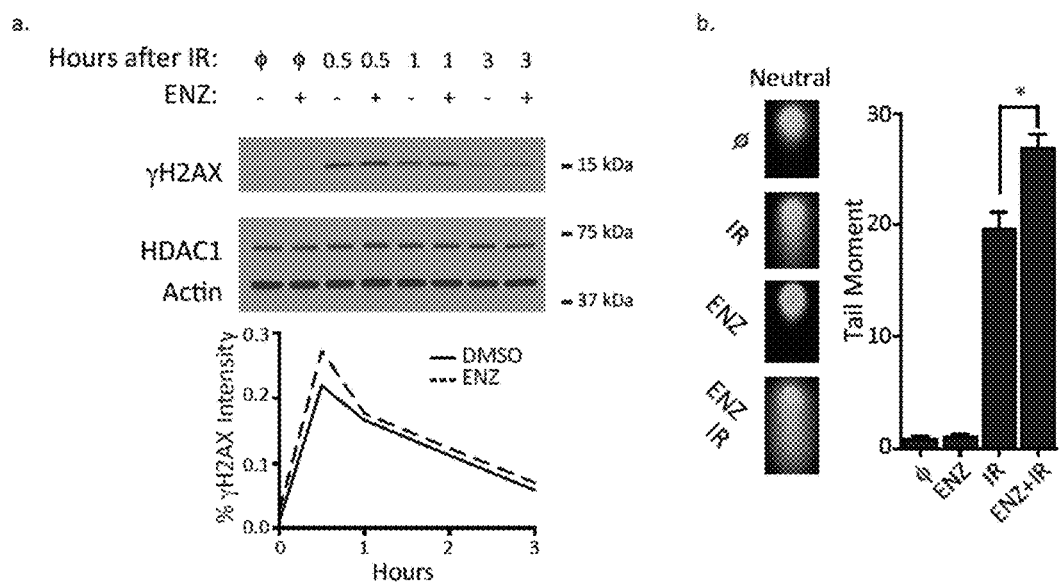
FIG. 16: AR regulates DNA damage and repair in AR, ER positive cells. (a) BT474 cells were cultured in hormone-proficient (FBS) media for 24 hours −/+ ENZ (20 µM) and then treated with IR: mock (φ) or 4 Gy. γH2AX, HDAC1, and Actin levels were measured at the indicated time points. Relative intensity of γH2AX was calculated by ImageJ64 as described (ref). (b) Neutral Comet assay of BT474 cells, showing increased double-strand breaks when cells were irradiated (10 Gy) after 24 hours of treatment with ENZ (20 µM). Data are expressed as the means±s.e.m of at least three experiments.
Figure 17:
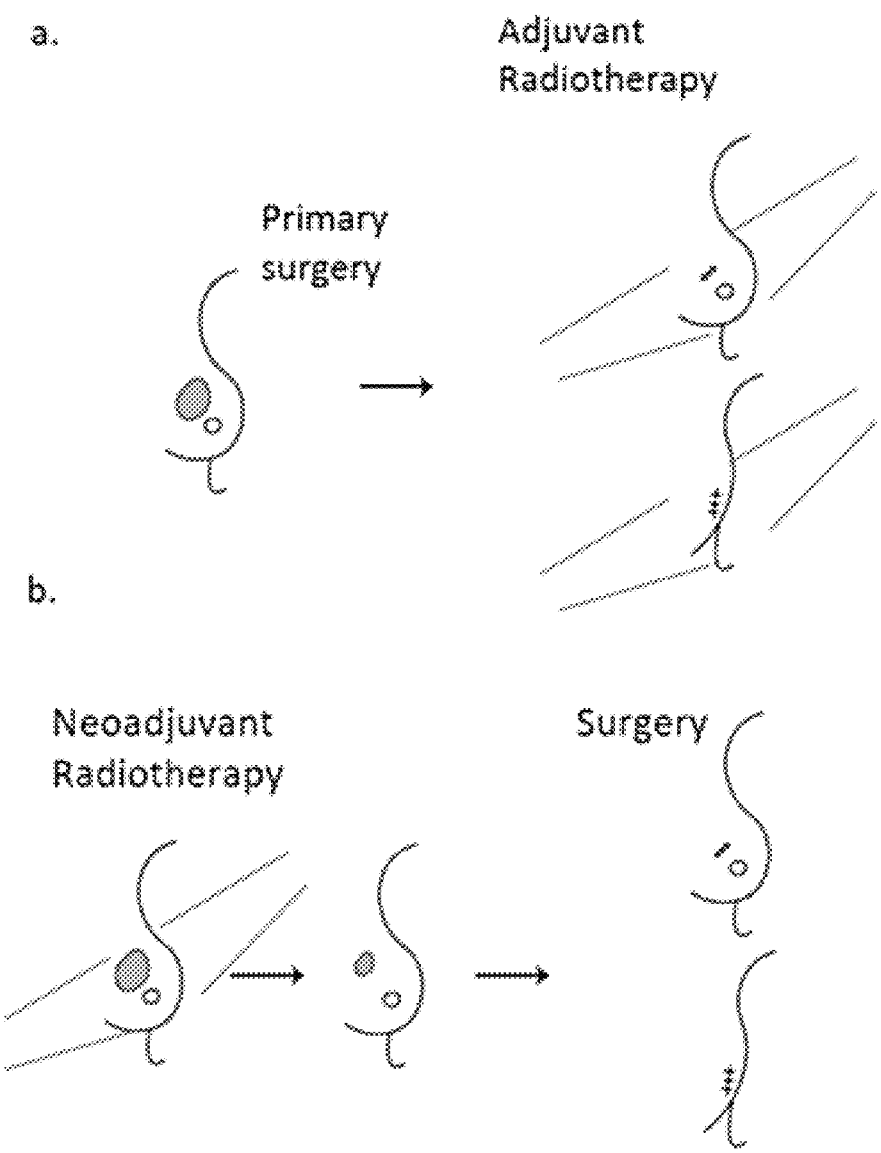
FIG. 17: Treatment schematic. Schematic representing embodiments for treatment delivering radiotherapy after surgery (Panel a), and embodiments for delivering radiotherapy with androgen blockade in the neoadjuvant or pre-operative setting (Panel b). The surgery may comprise, for example, breast conservation (keeping the breast intact (top schematic with nipple preserved)) or mastectomy (the removal of all or most breast tissue (bottom chest schematic).

Using the neutral comet assay, it was next determined whether the reduction in cellular survival was associated with increased DNA damage MDAMB453 cells were pre-treated for 24 hours with either DHT (FIG. 6c, left) or ENZ (FIG. 6c, right), prior to 15 Gy of irradiation. These results indicate that DHT decreased and ENZ increased DNA damage in MDAMB453 cells. To assess the role of DNA repair, the kinetics of γH2AX formation and resolution was measured, as surrogate marker of DNA DSBs and subsequent repair, under the same conditions. γH2AX kinetics were consistent with the results of the comet assay: levels of γH2AX in MDAMB453 cells were increased shortly after irradiation by ENZ increased and decreased by DHT (FIG. 6d), an effect that persisted at 24 hours. The kinetics of γH2AX formation and resolution in AR-negative HMC18 cells was unaffected by ENZ treatment, while DHT hastened γH2AX resolution in AR-positive C4-2 prostate cancer cells. These and similar results in the AR-positive, ER-positive, ErbB2 active cell line, BT474 (FIG. 16), suggest that suppression of androgen signaling results in increased DNA damage and/or decreased repair in breast cancer cells that express AR, independent of ER and ErbB2 activity.

Figure 6E:
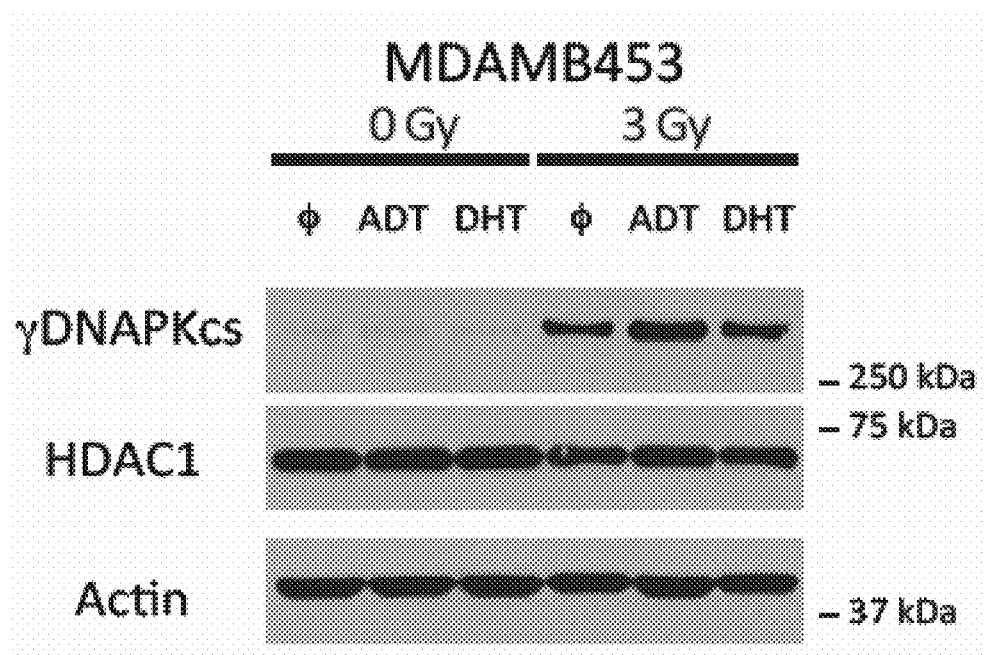
Figure 6F:
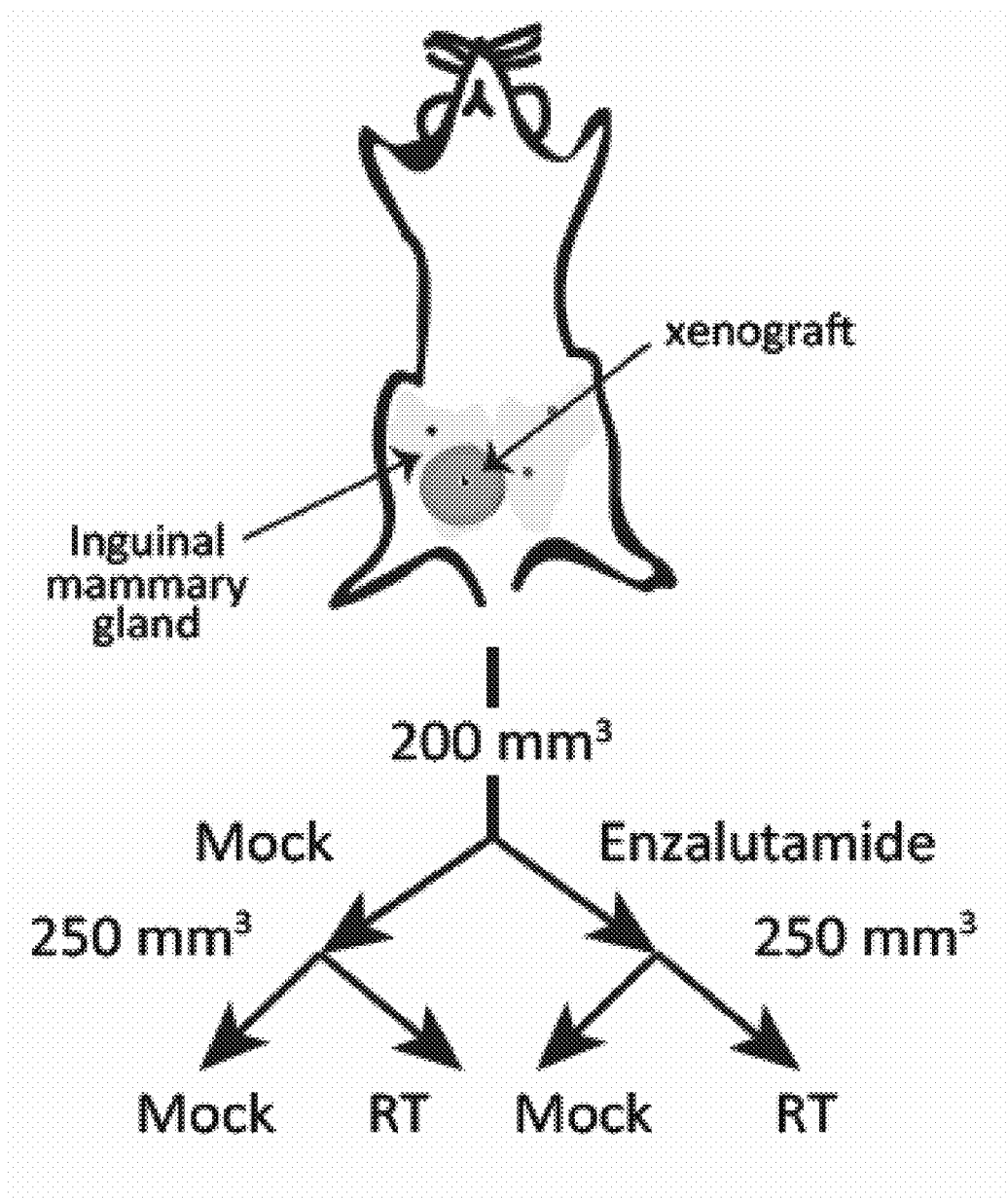
Figure 6G:
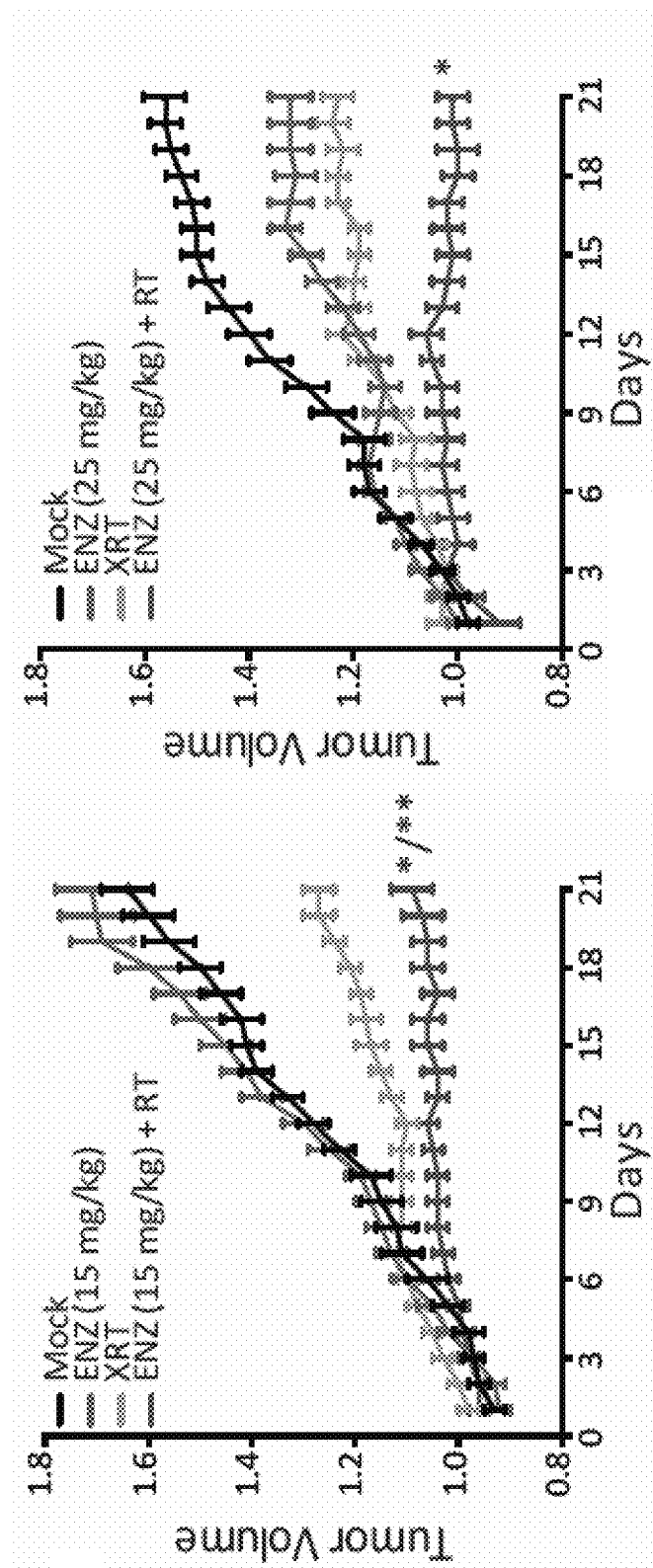
Figure 6H:
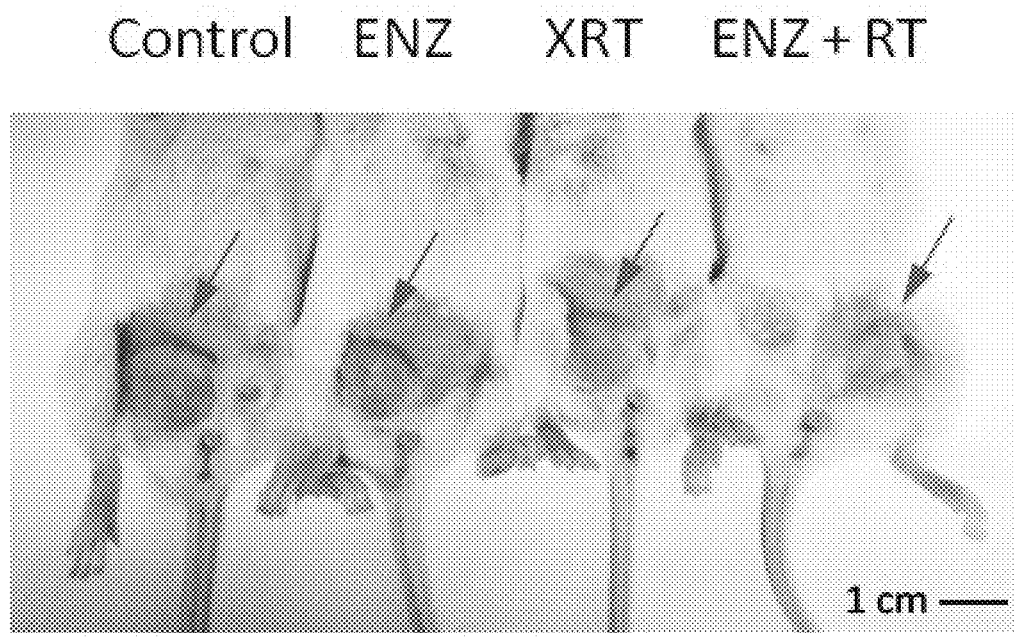
Figure 6I:
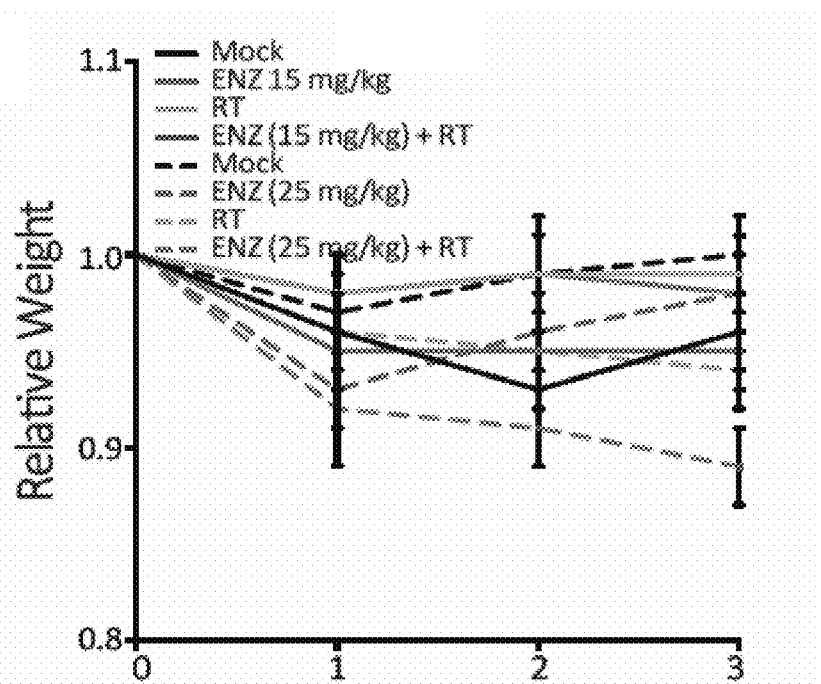

Previous work on AR regulated radiation resistance in prostate cancer suggested a decrease in the activity of PRKDC (or DNAPKcs), a key signaling molecule that initiates early stages of NHEJ, after androgen deprivation[56]. The phosphorylation of DNAPKcs on Ser2056 was examined, which is indicative of activated DNAPKcs, in MDAMB453 cells. Cells cultured in steroid-deprived media followed by irradiation had greater γDNAPKcs levels compared to steroid-replete media (FIG. 6e). Supplementation of steroid-deprived media with DHT maintained γDNAPKcs at similar levels to those cells grown in the steroid-replete media following irradiation. The greater level of γDNAPKcs are consistent with increased DNA damage after androgen deprivation in MDAMB453 cells and suggests cell-to-cell or lineage-to-lineage variability in the mechanism by which androgen signaling mediates survival after irradiation. These results demonstrate that androgen activity plays a pivotal role in the response of AR expressing breast cancer cells to ionizing radiation.

To assess this concept in vivo, MDAMB453 orthotopic xenografts were randomized into one of four treatment groups: mock, ENZ, ionizing radiation, or ENZ and ionizing radiation (FIG. 6f-i). The combination of ENZ (at 15 mg $kg^{-1}$ or 25 mg $kg^{-1}$) and ionizing radiation resulted in more effective suppression of tumor growth than either modality alone. However, despite no effects on tumor growth when used alone, ENZ at a dose 15 mg $kg^{-1}$ showed interactive tumor suppression with radiotherapy. Suppression of tumor growth was observed with ENZ at a dose of 25 mg $kg^{-1}$. However, mice that received both ENZ at a dose of 25 mg $kg^{-1}$ and radiation lost ~10% of their body weight during the course of treatment, suggesting that selection of ENZ dose is likely to be important in the optimization of the therapeutic index. Taken together, these data show that androgen ablation cooperates with ionizing radiation to decrease tumor cell growth and survival in AR-positive breast adenocarcinomas.

This example, which is exemplary, represents the largest analysis to date of cancer cell line survival after exposure to ionizing radiation. 533 genetically annotated tumor cell lines were profiled using a single, validated experimental platform and genetic determinants of tumor cellular response to radiation were identified. The distributions of survival after exposures to radiation across and within lineages were mostly Gaussian distributions, demonstrating significant underlying biological diversity. The clinical responses of some cancer types to radiotherapy vary in a manner not fully explained by clinical or histopathological features. These results suggest that intrinsic cellular determinants are likely to contribute to this variance.

Radiation sensitivity and genomic parameters were correlated using a statistical methodology that is sensitive to non-linear relationships and with better resolution at the high end of the matching range. It was shown that individual SCNA, gene mutations, and the basal expression of individual genes and gene sets correlate with radiation survival. In lineage-specific analysis of breast cancer cell lines it was demonstrated, for the first time, a role for AR expression in the response of breast cancer cells to ionizing radiation, mainly by preventing DNA damage. By studying a large number of cancer types, it was found that genetic correlates in any single cancer type can be found in other cancer types as well (e.g. Nrf2 activation in LUSC, LUAD, and hepatobiliary cancer and AR expression in prostate and breast adenocarcinomas). This supports the view that although diverse, cancer genomes reflect combinations of a limited number of functionally relevant events that can confer therapeutic resistance across cancer types. Importantly, the positive correlation between cellular response to ionizing radiation and genotoxic compounds suggests common genetic dependencies between the two most common cancer therapies in use, DNA-damaging chemotherapy and X-rays.

Several new genetic determinants of response to DNA damage were identified. These genetic alterations can have predictive capacity by identifying the likelihood of response to therapy and, consequently, prognosis. Diagnostics that measure genetic changes can assist in the selection of patients likely to respond to anti-cancer agents[4, 5, 6, 7, 57]. The potential for stratification of patients from heterogeneous populations to genetically similar subgroups can help guide the transition of DNA-damaging chemotherapy and X-rays from a generic population-based approach to one that is more personalized. A subset of the alterations that were identified can also guide combinatorial therapeutic strategies since these alterations conferred resistance and are targets of current FDA approved drugs, creating an opportunity for the precision targeting of therapeutic resistance (e.g. AR expression and anti-androgens in breast cancer and NFE2L2 activation and anti-PI3K therapies in NSCLC[28, 58, 59]).

Although several genetic determinants were identified that regulate the survival of cells after exposure to radiation, there are likely substantial additional parameters. Many of the cancer types that were profiled were represented by relatively few samples and others were not represented. Some SCNA were not measured due to the resolution limit of the array platform and although the input of >1600 cancer relevant genes profiled for mutations provides a powerful initial assessment of likely relevant genes, it is not comprehensive. Finally, levels of non-coding RNA, metabolites, and proteins and their post-translational modifications are also likely to impact the intrinsic cellular response to radiation. This data enables correlations of ionizing radiation sensitivity with levels of these important biomolecules as additional genomic and cellular datasets emerge.

In summary, the results reveal a genetic basis of the variation in the vulnerability of cancer to DNA damage. This information can help guide the transition of the use of X-rays and DNA-damaging drugs from the current generic approach to one in which these therapies are guided by genetic alterations in individual patient's tumor.

REFERENCES

1. Alhassani A, Chandra A, Chernew M E. The sources of the SGR "hole". *N Engl J Med* 366, 289-291 (2012).
2. Ree A H, Redalen K R. Personalized radiotherapy: concepts, biomarkers and trial design. *Br J Radiol* 88, 20150009 (2015).
3. Yard B, Chie E K, Adams D J, Peacock C, Abazeed M E. Radiotherapy in the Era of Precision Medicine. *Semin Radiat Oncol* 25, 227-236 (2015).
4. Chapman P B, et al. Improved survival with vemurafenib in melanoma with BRAF V600E mutation. *N Engl J Med* 364, 2507-2516 (2011).
5. Lynch T J, et al. Activating mutations in the epidermal growth factor receptor underlying responsiveness of non-small-cell lung cancer to gefitinib. *N Engl J Med* 350, 2129-2139 (2004).
6. Rosell R, et al. Erlotinib versus standard chemotherapy as first-line treatment for European patients with advanced EGFR mutation-positive non-small-cell lung cancer (EURTAC): a multicentre, open-label, randomised phase 3 trial. *Lancet Oncol* 13, 239-246 (2012).
7. Slamon D J, et al. Use of chemotherapy plus a monoclonal antibody against HER2 for metastatic breast cancer that overexpresses HER2. *N Engl J Med* 344, 783-792 (2001).
8. Abazeed M E, et al. Integrative radiogenomic profiling of squamous cell lung cancer. *Cancer Res* 73, 6289-6298 (2013).
9. Seashore-Ludlow B, et al. Harnessing Connectivity in a Large-Scale Small-Molecule Sensitivity Dataset. *Cancer Discov* 5, 1210-1223 (2015).
10. Harrington E A, et al. VX-680, a potent and selective small-molecule inhibitor of the Aurora kinases, suppresses tumor growth in vivo. *Nature medicine* 10, 262-267 (2004).
11. Beroukhim R, et al. The landscape of somatic copy-number alteration across human cancers. *Nature* 463, 899-905 (2010).
12. Zack T I, et al. Pan-cancer patterns of somatic copy number alteration. *Nat Genet* 45, 1134-1140 (2013).
13. Engelman J A, et al. MET amplification leads to gefitinib resistance in lung cancer by activating ERBB3 signaling. *Science* 316, 1039-1043 (2007).
14. Maris J M. Recent advances in neuroblastoma. *N Engl J Med* 362, 2202-2211 (2010).
15. Hastings P J, Lupski J R, Rosenberg S M, Ira G. Mechanisms of change in gene copy number. *Nature reviews Genetics* 10, 551-564 (2009).
16. Cancer Genome Atlas N. Comprehensive molecular characterization of human colon and rectal cancer. *Nature* 487, 330-337 (2012).
17. Cancer Genome Atlas Research N, et al. Integrated genomic characterization of endometrial carcinoma. *Nature* 497, 67-73 (2013).
18. Galy V, Olivo-Marin J C, Scherthan H, Doye V, Rascalou N, Nehrbass U. Nuclear pore complexes in the organization of silent telomeric chromatin. *Nature* 403, 108-112 (2000).
19. Velkova A, Carvalho M A, Johnson J O, Tavtigian S V, Monteiro A N. Identification of Filamin A as a BRCA1-interacting protein required for efficient DNA repair. *Cell cycle* 9, 1421-1433 (2010).
20. Schultz L B, Chehab N H, Malikzay A, Halazonetis T D. p53 binding protein 1 (53BP1) is an early participant in the cellular response to DNA double-strand breaks. *J Cell Biol* 151, 1381-1390 (2000).
21. Brumbaugh K M, et al. The mRNA surveillance protein hSMG-1 functions in genotoxic stress response pathways in mammalian cells. *Molecular cell* 14, 585-598 (2004).
22. Bao J, et al. RAN-binding protein 9 is involved in alternative splicing and is critical for male germ cell development and male fertility. *PLoS genetics* 10, e1004825 (2014).
23. Gong F, Fahy D, Liu H, Wang W, Smerdon M J. Role of the mammalian SWI/SNF chromatin remodeling complex in the cellular response to UV damage. *Cell cycle* 7, 1067-1074 (2008).
24. Lee J, Hirano T. RAD21L, a novel cohesin subunit implicated in linking homologous chromosomes in mammalian meiosis. *J Cell Biol* 192, 263-276 (2011).
25. Martini M, De Santis M C, Braccini L, Gulluni F, Hirsch E. PI3K/AKT signaling pathway and cancer: an updated review. *Annals of medicine* 46, 372-383 (2014).
26. Krasilnikov M, et al. Contribution of phosphatidylinositol 3-kinase to radiation resistance in human melanoma cells. *Molecular carcinogenesis* 24, 64-69 (1999).
27. Jiang Z, et al. Phosphatase and tensin homologue deficiency in glioblastoma confers resistance to radiation and temozolomide that is reversed by the protease inhibitor nelfinavir. *Cancer Res* 67, 4467-4473 (2007).
28. Abazeed M E, et al. Integrative radiogenomic profiling of squamous cell lung cancer. *Cancer Res*, (2013).
29. Taguchi K, Motohashi H, Yamamoto M. Molecular mechanisms of the Keap1-Nrf2 pathway in stress response and cancer evolution. *Genes Cells* 16, 123-140 (2011).
30. Zhang P, et al. Loss of Kelch-like ECH-associated protein 1 function in prostate cancer cells causes chemoresistance and radioresistance and promotes tumor growth. *Mol Cancer Ther* 9, 336-346 (2010).
31. Hast B E, et al. Cancer-derived mutations in KEAP1 impair NRF2 degradation but not ubiquitination. *Cancer Res* 74, 808-817 (2014).
32. Cancer Genome Atlas Research N. Comprehensive molecular profiling of lung adenocarcinoma. *Nature* 511, 543-550 (2014).
33. Shibata T, et al. Cancer related mutations in NRF2 impair its recognition by Keap1-Cul3 E3 ligase and promote malignancy. *Proceedings of the National Academy of Sciences of the United States of America* 105, 13568-13573 (2008).
34. Barbie D A, et al. Systematic RNA interference reveals that oncogenic KRAS-driven cancers require TBK1. *Nature* 462, 108-112 (2009).
35. Zaidi S H, Huddart R A, Harrington K J. Novel targeted radiosensitisers in cancer treatment. *Current drug discovery technologies* 6, 103-134 (2009).
36. Malhotra D, et al. Global mapping of binding sites for Nrf2 identifies novel targets in cell survival response through ChIP-Seq profiling and network analysis. *Nucleic Acids Res* 38, 5718-5734 (2010).
37. Dinkova-Kostova A T, Talalay P. NAD(P)H:quinone acceptor oxidoreductase 1 (NQO1), a multifunctional antioxidant enzyme and exceptionally versatile cytoprotector. *Arch Biochem Biophys* 501, 116-123 (2010).
38. Mathew R, et al. Autophagy suppresses tumorigenesis through elimination of p62. *Cell* 137, 1062-1075 (2009).

39. Komatsu M, et al. The selective autophagy substrate p62 activates the stress responsive transcription factor Nrf2 through inactivation of Keap1. *Nature cell biology* 12, 213-223 (2010).
40. Solis L M, et al. Nrf2 and Keap1 abnormalities in non-small cell lung carcinoma and association with clinicopathologic features. *Clin Cancer Res* 16, 3743-3753 (2010).
41. Buchanan C L, et al. Locoregional recurrence after mastectomy: incidence and outcomes. *Journal of the American College of Surgeons* 203, 469-474 (2006).
42. Huston T L, Simmons R M. Locally recurrent breast cancer after conservation therapy. *American journal of surgery* 189, 229-235 (2005).
43. Early Breast Cancer Trialists' Collaborative G, et al. Effect of radiotherapy after breast-conserving surgery on 10-year recurrence and 15-year breast cancer death: meta-analysis of individual patient data for 10,801 women in 17 randomised trials. *Lancet* 378, 1707-1716 (2011).
44. Ebctcg, et al. Effect of radiotherapy after mastectomy and axillary surgery on 10-year recurrence and 20-year breast cancer mortality: meta-analysis of individual patient data for 8135 women in 22 randomised trials. *Lancet* 383, 2127-2135 (2014).
45. Liang K, Lu Y, Jin W, Ang K K, Milas L, Fan Z. Sensitization of breast cancer cells to radiation by trastuzumab. *Mol Cancer Ther* 2, 1113-1120 (2003).
46. Joon D L, et al. Supraadditive apoptotic response of R3327-G rat prostate tumors to androgen ablation and radiation. *Int J Radiat Oncol Biol Phys* 38, 1071-1077 (1997).
47. Bolla M, et al. Long-term results with immediate androgen suppression and external irradiation in patients with locally advanced prostate cancer (an EORTC study): a phase III randomised trial. *Lancet* 360, 103-106 (2002).
48. D'Amico A V, Manola J, Loffredo M, Renshaw A A, DellaCroce A, Kantoff P W. 6-month androgen suppression plus radiation therapy vs radiation therapy alone for patients with clinically localized prostate cancer: a randomized controlled trial. *Jama* 292, 821-827 (2004).
49. Pilepich M V, et al. Phase III radiation therapy oncology group (RTOG) trial 86-10 of androgen deprivation adjuvant to definitive radiotherapy in locally advanced carcinoma of the prostate. *Int J Radiat Oncol Biol Phys* 50, 1243-1252 (2001).
50. Brys M, Wojcik M, Romanowicz-Makowska H, Krajewska W M. Androgen receptor status in female breast cancer: RT-PCR and Western blot studies. *Journal of cancer research and clinical oncology* 128, 85-90 (2002).
51. Barton V N, et al. Multiple molecular subtypes of triple-negative breast cancer critically rely on androgen receptor and respond to enzalutamide in vivo. *Mol Cancer Ther* 14, 769-778 (2015).
52. Cochrane D R, et al. Role of the androgen receptor in breast cancer and preclinical analysis of enzalutamide. *Breast cancer research: BCR* 16, R7 (2014).
53. Gucalp A, et al. Phase II trial of bicalutamide in patients with androgen receptor-positive, estrogen receptor-negative metastatic Breast Cancer. *Clin Cancer Res* 19, 5505-5512 (2013).
54. Akiyama T, Matsuda S, Namba Y, Saito T, Toyoshima K, Yamamoto T. The transforming potential of the c-erbB-2 protein is regulated by its autophosphorylation at the carboxyl-terminal domain. *Mol Cell Biol* 11, 833-842 (1991).
55. Lehmann B D, et al. Identification of human triple-negative breast cancer subtypes and preclinical models for selection of targeted therapies. *The Journal of clinical investigation* 121, 2750-2767 (2011).
56. Goodwin J F, et al. A hormone-DNA repair circuit governs the response to genotoxic insult. *Cancer Discov* 3, 1254-1271 (2013).
57. Druker B J, et al. Efficacy and safety of a specific inhibitor of the BCR-ABL tyrosine kinase in chronic myeloid leukemia. *N Engl J Med* 344, 1031-1037 (2001).
58. Lee J M, Hanson J M, Chu W A, Johnson J A. Phosphatidylinositol 3-kinase, not extracellular signal-regulated kinase, regulates activation of the antioxidant-responsive element in IMR-32 human neuroblastoma cells. *The Journal of biological chemistry* 276, 20011-20016 (2001).
59. Mitsuishi Y, et al. Nrf2 redirects glucose and glutamine into anabolic pathways in metabolic reprogramming. *Cancer Cell* 22, 66-79 (2012).
60. Cowley G S, et al. Parallel genome-scale loss of function screens in 216 cancer cell lines for the identification of context-specific genetic dependencies. *Scientific data* 1, 140035 (2014).
61. Franken N A, Rodermond H M, Stap J, Haveman J, van Bree C. Clonogenic assay of cells in vitro. *Nat Protoc* 1, 2315-2319 (2006).
62. Cai Z, Chattopadhyay N, Liu W J, Chan C, Pignol J P, Reilly R M. Optimized digital counting colonies of clonogenic assays using ImageJ software and customized macros: comparison with manual counting. *International journal of radiation biology* 87, 1135-1146 (2011).
63. Linfoot E H. An informational measure of correlation. *Information and Control* 1, 85-89 (1957).
64. Joe H. Relative Entropy Measures of Multivariate Dependence. *Journal of the American Statistical Association* 84, 157-164 (1989).
65. Barretina J, et al. The Cancer Cell Line Encyclopedia enables predictive modelling of anticancer drug sensitivity. *Nature* 483, 603-607 (2012).
66. Cancer Genome Atlas Research N. Comprehensive genomic characterization defines human glioblastoma genes and core pathways. *Nature* 455, 1061-1068 (2008).
67. Olshen A B, Venkatraman E S, Lucito R, Wigler M. Circular binary segmentation for the analysis of array-based DNA copy number data. *Biostatistics* 5, 557-572 (2004).
68. Korn J M, et al. Integrated genotype calling and association analysis of SNPs, common copy number polymorphisms and rare CNVs. *Nat Genet* 40, 1253-1260 (2008).
69. Mermel C H, Schumacher S E, Hill B, Meyerson M L, Beroukhim R, Getz G. GISTIC2.0 facilitates sensitive and confident localization of the targets of focal somatic copy-number alteration in human cancers. *Genome biology* 12, R41 (2011).
70. Li B, Dewey C N. RSEM: accurate transcript quantification from RNA-Seq data with or without a reference genome. *BMC Bioinformatics* 12, 323 (2011).
71. Cancer Genome Atlas Research N. Comprehensive genomic characterization of squamous cell lung cancers. *Nature* 489, 519-525 (2012).

All publications and patents mentioned in the specification and/or listed below are herein incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the relevant fields are intended to be within the scope described herein

I claim:

1. A method of treating cancer comprising:
   a) determining that a subject has androgen receptor positive breast cancer cells;
   b) treating said subject with an anti-androgen receptor agent under conditions such that at least some or most or all of said androgen receptor positive cancer cells are sensitized to radiation therapy; and
   c) treating said subject with radiation therapy, wherein said radiation therapy is performed at least 1 hour after said treating with said anti-androgen receptor agent, and wherein said treating causes at least a portion of said androgen receptor positive cancer cells to die.

2. The method of claim 1, wherein said anti-androgen receptor agent sensitizes said androgen receptor positive cancer cells to said radiation therapy, such that a higher proportion of said cancer cells are killed by said radiation therapy than without said anti-androgen receptor agent.

3. The method of claim 1, wherein said radiation therapy is performed at least 6 hours after said treating with said anti-androgen receptor agent.

4. The method of claim 1, wherein said radiation therapy is performed at least 1-24 hours after said treating with said anti-androgen receptor agent.

5. The method of claim 1, wherein said radiation therapy is performed at least 1-2 months after said treating with said anti-androgen receptor agent.

6. The method of claim 1, wherein said anti-androgen receptor agent is administered to said subject in a dosage between 1 mg/kg to 35 mg/kg.

7. The method of claim 1, wherein said anti-androgen receptor agent is administered to said subject in a dosage of about 10-15 mg/kg.

8. The method of claim 1, wherein said determining comprises receiving or reviewing a report that said subject has androgen positive cancer cells.

9. The method of claim 1, wherein said determining comprises performing an in vitro assay on a sample from said subject.

10. The method of claim 1, wherein said anti-androgen receptor agent is an androgen receptor antagonists selected from the group consisting of: flutamide, nilutamide, bicalutamide, enzalutamide, apalutamide, cyproterone acetate, megestrol acetate, chlormadinone acetate, spironolactone, canrenone, drospirenone, ketoconazole, topilutamide (fluridil), and cimetidine.

11. The method of claim 1, wherein said anti-androgen receptor agent is a selective androgen receptor modulator (SARM) selected from the group consisting of: Enobosarm (Ostarine, MK-2866, GTx-024), BMS-564,929; LGD-4033 (Ligandrol), SARM (5-3/5-6); AC-262,356; JNJ-28330835; LGD-2226; LGD-3303; S-40503; and S-23.

12. The method of claim 1, wherein said radiation therapy comprises subjecting said subject to X-rays, gamma rays, and or charged particles.

* * * * *